United States Patent [19]
Stylli et al.

[11] Patent Number: 5,985,214
[45] Date of Patent: Nov. 16, 1999

[54] SYSTEMS AND METHODS FOR RAPIDLY IDENTIFYING USEFUL CHEMICALS IN LIQUID SAMPLES

[75] Inventors: Chari Stylli; Samuel S. Beckey, both of San Diego; Christopher Bentley Shumate, La Jolla; Peter J. Coassin, Encinitas, all of Calif.

[73] Assignee: Aurora Biosciences Corporation, San Diego, Calif.

[21] Appl. No.: 08/858,016

[22] Filed: May 16, 1997

[51] Int. Cl.⁶ .............................. G01N 31/00; G06F 19/00
[52] U.S. Cl. .................................. 422/65; 422/66; 422/67; 422/63; 364/468.19; 364/478.02
[58] Field of Search ................................ 435/7.1, 287.1, 435/288.3, 288.7; 422/50, 63, 68.1, 82.05, 65, 66, 67, 100; 364/478.02, 468.19

[56] References Cited

U.S. PATENT DOCUMENTS

| | | |
|---|---|---|
| Re. 32,414 | 5/1987 | Hutchins et al. . |
| 4,000,976 | 1/1977 | Kramer et al. . |
| 4,058,146 | 11/1977 | Citrin . |
| 4,115,010 | 9/1978 | McAleer et al. . |
| 4,125,680 | 11/1978 | Shropshire et al. . |
| 4,135,561 | 1/1979 | Senelonge . |
| 4,256,153 | 3/1981 | Lamaziere . |
| 4,262,711 | 4/1981 | Anderson . |
| 4,276,048 | 6/1981 | Leaback . |
| 4,313,476 | 2/1982 | Bennett et al. . |
| 4,342,407 | 8/1982 | Citrin . |
| 4,446,104 | 5/1984 | Hammerling et al. . |
| 4,478,094 | 10/1984 | Salomaa et al. . |
| 4,488,241 | 12/1984 | Hutchins et al. . |
| 4,493,896 | 1/1985 | La Motte, III et al. . |
| 4,496,657 | 1/1985 | Coppersmith et al. . |
| 4,498,782 | 2/1985 | Proctor et al. . |
| 4,501,970 | 2/1985 | Nelson . |
| 4,507,044 | 3/1985 | Hutchins et al. . |
| 4,510,684 | 4/1985 | Hutchins et al. . |
| 4,562,871 | 1/1986 | Astle . |
| 4,565,100 | 1/1986 | Malinoff . |

(List continued on next page.)

FOREIGN PATENT DOCUMENTS

| | | |
|---|---|---|
| 0 251 441 B1 | 12/1993 | European Pat. Off. . |
| 0 635 713 A1 | 1/1995 | European Pat. Off. . |
| WO 88/00707 | 1/1988 | WIPO . |
| WO 91/04793 | 4/1991 | WIPO . |
| WO 91/16977 | 11/1991 | WIPO . |
| WO 91/17445 | 11/1991 | WIPO . |
| WO 92/14127 | 8/1992 | WIPO . |
| WO 93/13423 | 7/1993 | WIPO . |
| WO 93/25913 | 12/1993 | WIPO . |
| WO 95/11461 | 4/1995 | WIPO . |
| WO 95/25423 | 9/1995 | WIPO . |
| WO 95/31284 | 11/1995 | WIPO . |
| WO 96/05488 | 2/1996 | WIPO . |
| WO 97/26539 | 7/1997 | WIPO . |

OTHER PUBLICATIONS

France et al., Proceedings of the International Symposium on Laboratory Automation and Robotics, 1992, pp. 400–410.

(List continued on next page.)

Primary Examiner—Ponnathapura Achutamurthy
Assistant Examiner—Joseph W. Ricigliano
Attorney, Agent, or Firm—Fish & Richardson P.C.

[57] ABSTRACT

The present invention provides for systems and methods that utilize automated and integratable workstations for identifying chemicals having useful activity. The present invention is also directed to chemical entities and information (e.g., chemical or biological activities of chemicals) generated or discovered by operation of workstations of the present invention. The present invention includes automated workstations that are programmably controlled to minimize processing times at each workstation and that can be integrated to minimize the processing time of the liquid samples from the start to finish of the process.

30 Claims, 29 Drawing Sheets

U.S. PATENT DOCUMENTS

| | | |
|---|---|---|
| 4,580,895 | 4/1986 | Patel . |
| 4,586,151 | 4/1986 | Boute . |
| 4,607,196 | 8/1986 | Abrahams et al. . |
| 4,632,631 | 12/1986 | Dunlap . |
| 4,677,195 | 6/1987 | Hewick et al. . |
| 4,692,308 | 9/1987 | Riley et al. . |
| 4,701,412 | 10/1987 | Naylor . |
| 4,701,754 | 10/1987 | Provonchee . |
| 4,703,008 | 10/1987 | Lin . |
| 4,710,031 | 12/1987 | Kelly et al. . |
| 4,753,775 | 6/1988 | Ebersole et al. . |
| 4,803,050 | 2/1989 | Mack . |
| 4,824,230 | 4/1989 | Litt . |
| 4,835,711 | 5/1989 | Hutchins et al. . |
| 4,968,148 | 11/1990 | Chow et al. . |
| 5,021,217 | 6/1991 | Oshikubo . |
| 5,035,270 | 7/1991 | Herzog . |
| 5,055,263 | 10/1991 | Meltzer . |
| 5,073,029 | 12/1991 | Eberly et al. . |
| 5,082,628 | 1/1992 | Andreotti et al. . |
| 5,104,621 | 4/1992 | Pfost et al. . |
| 5,104,808 | 4/1992 | Laska et al. . |
| 5,108,703 | 4/1992 | Pfost et al. . |
| 5,112,134 | 5/1992 | Chow et al. . |
| 5,125,748 | 6/1992 | Bjornson et al. . |
| 5,139,744 | 8/1992 | Kowalski . |
| 5,206,568 | 4/1993 | Bjornson et al. . |
| 5,213,766 | 5/1993 | Flesher et al. . |
| 5,219,528 | 6/1993 | Clark . |
| 5,226,462 | 7/1993 | Carl . |
| 5,243,540 | 9/1993 | Van Albert et al. . |
| 5,250,263 | 10/1993 | Manz . |
| 5,326,648 | 7/1994 | Koryasu et al. ............................ 436/48 |
| 5,332,549 | 7/1994 | MacIndoe, Jr. . |
| 5,350,564 | 9/1994 | Mazza et al. . |
| 5,355,215 | 10/1994 | Schroeder et al. . |
| 5,355,439 | 10/1994 | Bernstein et al. . |
| 5,366,896 | 11/1994 | Margrey et al. . |
| 5,455,008 | 10/1995 | Earley et al. . |
| 5,468,110 | 11/1995 | McDonald et al. . |
| 5,497,670 | 3/1996 | Carl . |
| 5,512,247 | 4/1996 | Bonacina et al. . |
| 5,518,688 | 5/1996 | Gianino . |
| 5,525,302 | 6/1996 | Astle . |
| 5,527,684 | 6/1996 | Mabile et al. . |
| 5,540,889 | 7/1996 | Gordon et al. . |
| 5,542,012 | 7/1996 | Fernandes et al. . |
| 5,544,535 | 8/1996 | Thomas . |
| 5,547,849 | 8/1996 | Baer et al. . |
| 5,567,294 | 10/1996 | Dovichi et al. . |
| 5,578,832 | 11/1996 | Trulson et al. . |
| 5,580,722 | 12/1996 | Foulkes et al. . |
| 5,581,691 | 12/1996 | Hsu et al. . |
| 5,581,758 | 12/1996 | Burnett et al. . |
| 5,589,351 | 12/1996 | Harootunian . |
| 5,593,267 | 1/1997 | McDonald et al. . |
| 5,623,415 | 4/1997 | O'Bryan et al. ................... 364/478.13 |
| 5,665,543 | 9/1997 | Foulkes et al. . |
| 5,670,113 | 9/1997 | Akong et al. . |
| 5,675,715 | 10/1997 | Bernstein et al. . |
| 5,691,188 | 11/1997 | Pausch et al. . |
| 5,696,887 | 12/1997 | Bernstein et al. . |
| 5,776,502 | 7/1998 | Foulkes et al. . |

OTHER PUBLICATIONS

Goddard et al., Proceedings of the International Symposium on Laboratory Automation and Robotics, 1992, pp. 392–399.

Schroede and Neagle, J. Biolmolecular Screening, 1:75–80 (1996).

Shuttleworth, Inc., "Flexible, Low–Line Pressure Accumulatoing Slip–Torque Conveyor Systems" (ca. 1993).

Shuttleworth, Inc., "Flat Panel Display News," Feb. 1996.

Ultra High Throughput Screenign System (The Allegro TM). Zymark Corporation homepage and specifically URL http://www.zymark.com/MARKETING/drugd/allegr.htm, Jul.17, 1997.

Dispensing into 96 well plate, 6.5mm diam.. wells

Dispensing into 384 well plate, 3.4mm diam. wells

Dispensing into 864 well plate, 2mm diam. wells

SYSTEMS AND METHODS FOR RAPIDLY IDENTIFYING USEFUL CHEMICALS IN LIQUID SAMPLES

TECHNICAL FIELD

The present invention generally relates to automated and integrated systems and methods for rapidly identifying chemicals with biological activity in liquid samples, particularly automated screening of low volume samples for new medicines, agrochemicals, or cosmetics.

BACKGROUND

Systems and methods for rapidly identifying chemicals with biological activity in samples, especially small liquid samples, can benefit a number of different fields. For instance, the agrochemical, pharmaceutical, and cosmetic fields all have applications where large numbers of liquid samples containing chemicals are processed. Currently, many such fields use various strategies to reduce processing times, such as simplified chemistry, semi-automation and robotics. While such strategies may improve the processing time for a particular type of liquid sample, process step or chemical reaction, such methods or apparatuses can seldom integrate the entire process, especially the generation or detection of chemical events in small volumes. Such apparatuses are also often limited in their application, since many of them are designed for, and dedicated to, a particular type of liquid sample or chemical reaction.

In most processes involving liquid samples, as the complexity of the liquid sample processing increases the process time per sample increases. Although, some very simple chemical reactions or liquid processing methods can achieve extremely high throughput rates, such as in the manufacturing of containerized liquids, complicated processing of liquids is typically several orders of magnitude slower. In some instances, the processing of liquid samples, such as in pharmaceutical arts, which usually demands complicated liquid processing for drug discovery, can obtain throughput rates of approximately 3,000 samples per day. This type of processing in general, however, uses liquid sample volumes on the order of 100 to 200 microliters, which often requires relatively large amounts of exotic and expensive reagents, and does not typically incorporate automated access to large stores of liquid reagents.

Consequently, there is a need to provide components, systems and methods for rapidly processing liquid samples at high throughput rates, particularly liquid samples of microliter volumes, one to ten microliters, to identify chemicals with useful activity.

SUMMARY

Figure 1:
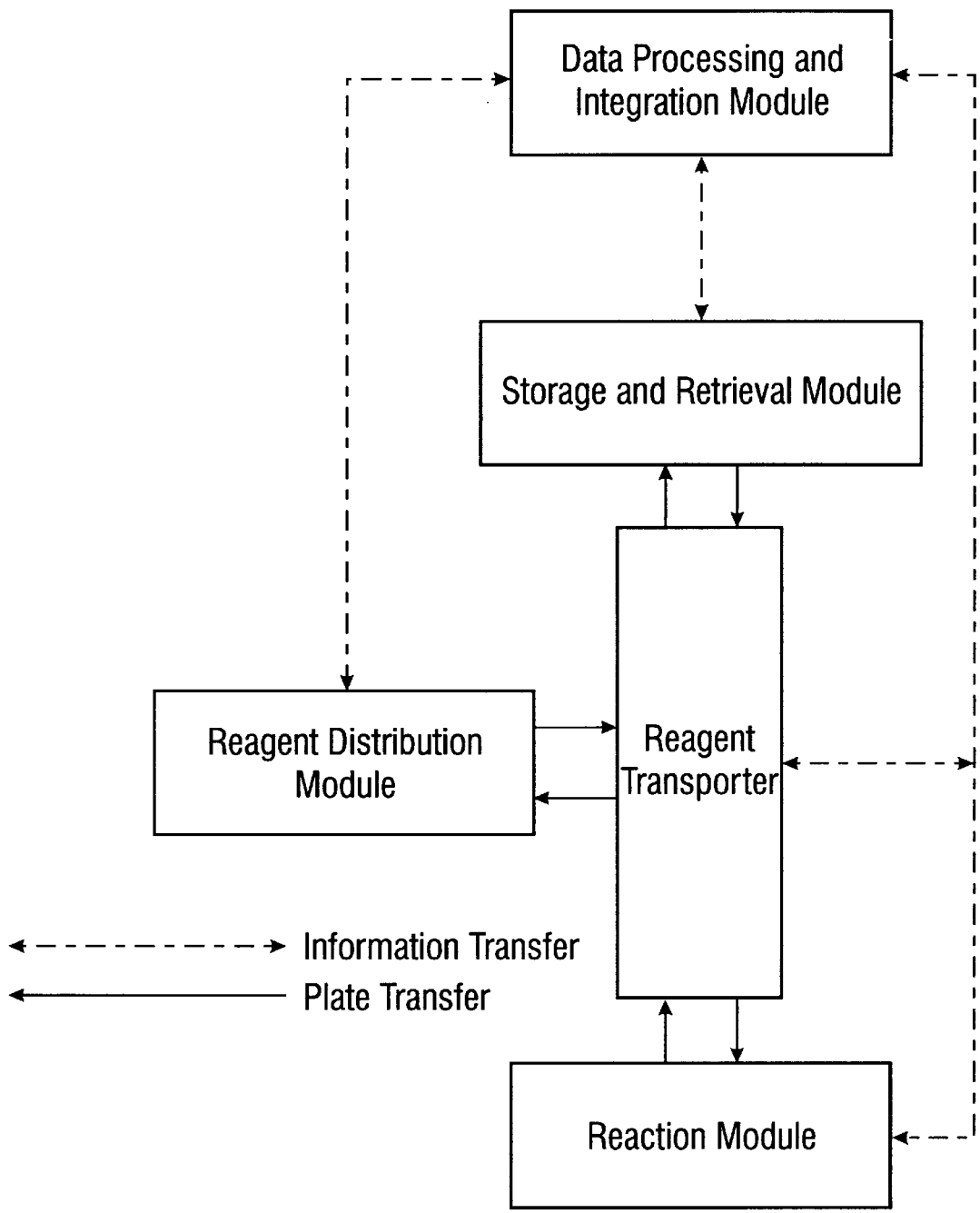
FIG. 1 shows one embodiment of a liquid sample processing system and exemplary routes of information and plate transfer within.

The present invention is directed to systems and methods that utilize automated and integratable workstations for identifying chemicals having useful activity. The present invention is also directed to chemical entities and information (e.g., chemical or biological activities of chemicals) generated or discovered by operation of workstations of the present invention.

The present invention includes automated workstations that are programmably controlled to minimize processing times at each workstation and that can be integrated to minimize the processing time of the liquid samples from the start to finish of the process. Typically, a system of the present invention would include:

A. a storage and retrieval module comprising storage locations for storing a plurality of chemicals in solution in addressable chemical wells, a chemical well retriever and having programmable selection and retrieval of the addressable chemical wells and having a storage capacity for at least 100,000 the addressable wells.

B. a sample distribution module comprising a liquid handler to aspirate or dispense solutions from selected the addressable chemical wells, the chemical distribution module having programmable selection of, and aspiration from, the selected addressable chemical wells and programmable dispensation into selected addressable sample wells (including dispensation into arrays of addressable wells with different densities of addressable wells per centimeter squared), C. a sample transporter to transport the selected addressable chemical wells to the sample distribution module and optionally having programmable control of transport of the selected addressable chemical wells (including adaptive routing and parallel processing), D. a reaction module comprising either a reagent dispenser to dispense reagents into the selected addressable sample wells or a fluorescent detector to detect chemical reactions in the selected addressable sample wells, and E. a data processing and integration module.

The storage and retrieval module, the sample distribution module, and the reaction module are integrated and programmably controlled by the data processing and integration module. The storage and retrieval module, the sample distribution module, the sample transporter, the reaction module and the data processing and integration module are operably linked to facilitate rapid processing of the addressable sample wells. Typically, devices of the invention can process at least 100,000 addressable wells in 24 hours.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and many of the automation, computer, detection, chemistry and laboratory procedures described below are those well known and commonly employed in the art. Standard techniques are usually used for engineering, robotics, informatics, optics, molecular biology, computer software and integration. Generally, chemical reactions, cell assays and enzymatic reactions are performed according to the manufacturer's specifications where appropriate. The techniques and procedures are generally performed according to conventional methods in the art and various general references (see generally, Knuth, Donald E., *The Art of Computer Programming*, Volume 1, *Fundamental Algorithms*, Third Edition (Reading, Mass.: Addison-Wesley, 1997); Volume 2, *Seminumerical Algorithms*, Second Edition (Reading, Mass.: Addison-Wesley, 1981) ;Volume 3, *Sorting and Searching*, (Reading, Mass.: Addison-Wesley, 1973); for computational methods, Lakowicz, J. R. *Principles of Fluorescence Spectroscopy*, New York: Plenum Press (1983) for fluorescence techniques and Sambrook et al. Molecular Cloning: A Laboratory Manual, 2d ed. (1989) Cold Spring Harbor Laboratory Press, Cold Spring Harbor, N.Y. for molecular biology methods, which are incorporated herein by reference which are provided throughout this document). The nomenclature used herein and the laboratory procedures in chemistry, molecular biology, automation, computer sciences, and drug discovery described below are those well known and commonly employed in the art. Standard techniques are often used for chemical syntheses, chemical analyses, drug screening, and diagnosis. As employed throughout the disclosure, the following terms, unless otherwise indicated, shall be understood to have the following meanings:

"Adaptive routing" refers to a change in the path to be followed by a work unit as a result of conditions encountered during a stage or stages of processing. Conditions could include results of previous processing steps, equipment out of order, processing priorities, or other factors. The path is the sequence of steps called for to process a work unit. For example, the path is the sequence of steps called for in the assay definition, which may be independent of specific processing equipment. System processing is typically performed at workstations, so adaptive routing allows alternative workstations to be substituted by computerized instruction.

"Daughter plate" refers to a plate containing a portion of the liquid of the wells of a master plate of the same or different well density. A master plate refers to a plate with wells containing a stock solution.

"Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may manifest only in particular cell types.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. For instance, two components are mechanically linked by a conveyor means.

"Parallel processing" refers to the routing of material flow to facilitate the simultaneous handling of multiple work units at or within multiple workstations. Parallel processing between workstations is accomplished by maintaining individual work queues within a transport system for each workstation, and allowing for many liquid handling operations to be performed simultaneously. For example, work units can be delivered in parallel to each of the workstations disposed on a transport system, while other units are queuing for subsequent operation at those workstations. Transfers from the workstations are also to be accomplished in this manner. Within workstations, many parallel instruments can perform work on a number of units simultaneously. For instance, four parallel aspirate/dispense devices can simultaneously operate on four plates in a workstation. When the term parallel processing is used, unless explicitly stated, it does not preclude other types of processing, such as serial processing.

"Polynucleotide" refers to a polymeric form of nucleotides of at least 10 bases in length, either ribonucleotides or deoxynucleotides or a modified form of either type of nucleotide. The term includes single and double stranded forms of DNA.

"Chemical plate" refers to a plate containing chemcials, such as a master plate with stock solutions or a daughter plate with stock solutions or dilutions thereof. A well of a chemical plate will usually have only one chemical in solution.

"Sample plate" refers to a plate containing a sample to be processed, such as a sample for testing or synthesis. Sample plates are usually used in a reaction module, to permit a chemical reaction, or detection of a physical property of the sample.

"Test chemical" refers to a chemical to be tested by one or more screening devices or method(s) of the invention as a putative modulator.

"Fluorescent label" refers to incorporation of a detectable marker, e.g., by incorporation of a fluorescent moiety to a chemical entity that binds to a target or attachment to a polypeptide of biotinyl moieties that can be detected by avidin (e.g., streptavidin containing a fluorescent label or enzymatic activity that can be detected by fluorescence detection methods). Various methods of labeling polypeptides and glycoproteins are known in the art and may be used. Examples of labels for polypeptides include, but are not limited to dyes (e.g., FITC and rhodamine), intrinsically fluorescent proteins, and lanthanide phosphors. In some embodiments, labels are attached by spacer arms of various lengths to reduce potential steric hindrance.

"Reporter gene" refers to a nucleotide sequence encoding a protein that is readily detectable either by its presence or activity, including, but not limited to, luciferase, green fluorescent protein, chloramphenicol acetyl transferase, p-galactosidase, secreted placental alkaline phosphatase, P-lactamase, human growth hormone, and other secreted enzyme reporters. Generally, reporter genes encode a polypeptide not otherwise produced by the host cell which is detectable by analysis of the cell(s), e.g., by the direct fluorometric, radioisotopic or spectrophotometric analysis of the cell(s) and preferably without the need to remove the cells for signal analysis of a well. Preferably, the gene encodes an enzyme which produces a change in fluorometric properties of the host cell which is detectable by qualitative, quantitative or semi-quantitative function of transcriptional activation. Exemplary enzymes include esterases, phosphatases, proteases (tissue plasminogen activator or urokinase) and other enzymes whose function can be detected by appropriate chromogenic or fluorogenic substrates known to those skilled in the art. Proteins, particularly enzymes, of reporter genes can also be used as probes in biochemical assays, for instance after proper conjugation to either the target or a chemical entity that binds to the target.

"Pharmaceutical agent or drug" refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (ed. Parker, S., 1985, McGraw-Hill, San Francisco, incorporated herein by reference).

Introduction

The present invention is directed to systems and methods that utilize automated and integratable workstations for identifying chemicals having useful activity. The present invention is also directed to chemical entities and information (e.g., chemical or biological activities of chemicals) generated or discovered by operation of workstations of the present invention.

The present invention typically includes automated workstations that are programmably controlled to minimize processing times at each workstation and can be integrated to minimize the processing time of the liquid samples from the start to finish of the process. Typically, a system of the present invention would include most or all of components used in processing liquid samples to identify a useful chemical, starting with a large store of different reagents (usually liquid) through the later stage processing steps, such as chemical reactions, or detection of an analyte or measurement of a physical property of a sample, as well as a component to collect information resulting from such a process. Such a system, as shown in FIG. 1, usually includes the following components:

a) a storage and retrieval module for storing and retrieving very large numbers (at least about 100,000) of different reagents in containers, b) a sample distribution module to handle (e.g., aspirate samples from containers and dispense samples into sample containers) small volumes of liquids at a high rate of speed, c) a sample transporter to transport reagents from a selected component to another at a compatible throughput rate, d) a reaction module (e.g., a reagent dispenser or a detector) for chemical reactions or physical measurements at high throughput rates, and e) a data processing and integration module that can control module operation.

If desired, each separate module is integrated and programmably controlled to facilitate the rapid processing of liquid samples, as well as being operably linked to facilitate the rapid processing of liquid samples.

As a non-limiting introduction to the breadth of the invention, the invention includes several general and useful aspects, including:

1) ensembles of integrated components to form a system (e.g., a system that includes a storage and retrieval module, sample distribution module, sample transporter, reaction module and data processing and integration module), 2) individual components (e.g., storage and retrieval module, sample distribution module, sample transporter, reaction module or data processing and integration module), 3) methods of identifying useful chemicals, 4) chemicals discovered by the operation of such components or systems, 5) methods and compositions for modulating biological processes with a chemical having modulating activity discovered by the operation of such components or systems, and 6) computer program products, computational methods and storage devices related to either the operation of, or information generated by, components or systems of the invention.

These aspects of the invention, as well as others described herein, can be achieved by using the devices, compositions and methods described herein. To gain a full appreciation of the scope of the invention, it will be further recognized that various aspects of the invention can be combined to make desirable embodiments of the invention. For example, the invention includes a storage and retrieval module programmably integrated with a computer device to a sample transporter and a sample distribution module, and operably linked to the sample transporter and the sample distribution module. Such combinations result in particularly useful and robust embodiments of the invention.

FIG. 1 shows one embodiment of a liquid processing system that comprises a storage and retrieval module, sample distribution module, sample transporter, reaction module and data processing and integration module. As described in further detail herein, the data processing and integration module can integrate the various modules and provide for computer control of the modules and sample transporter, as well as routing (e.g., adaptive routing), and parallel processing of work to be performed by each workstation. Information transfer can occur from the data processing and integration module to a workstation and from a workstation to a data processing and integration module. Material transfer, in this case plates, can occur between modules and is facilitated by operably linking the modules together with the sample transporter. Because the invention permits tremendous flexibility for integrating liquid processing workstation, many embodiments of the invention are contemplated, such as in FIG. 2, which shows a liquid processing system comprised of an additional workstation that could be used for identifying useful chemicals, as described in more detail.

The present invention is described more fully herein first as a system and then on a component-by-component basis. Specific examples of systems and methods suited to particular applications, chemicals discovered by the present invention and methods relating to modulating biological processes with such chemicals are then described. The Examples are preceded by a description of computer program products, computational methods and storage devices related to either the operation of, or information generated by, components or systems of the invention.

System for Rapidly Processing Liquid Samples

The invention provides for a system for rapidly processing liquid samples, comprising workstations that are programmably integrated and operably linked to facilitate processing of liquid samples and to minimize processing time. The system can include a storage and retrieval module that can house a plurality of chemicals in solution in addressable chemical wells. A chemical well retriever is disposed to store and retrieve addressable chemical wells that can be stored in the storage and retrieval module. The storage and retrieval module can be computer-controlled to offer programmable selection and retrieval of the addressable chemical wells. The storage and retrieval module can optionally include an addressable well sorter that acts as a buffer for temporary addressable well storage.

A sample transporter is operably linked to the storage and retrieval module to transport the selected addressable chemical wells to a sample distribution module. The sample transporter is optionally programmably controlled to direct transport of the selected addressable chemical wells to the sample distribution module.

The sample distribution module comprises a liquid handler to aspirate or dispense solutions from selected addressable chemical wells. The sample distribution module can provide for a programmable selection of and aspiration from the selected addressable chemical wells and programmable dispensation into addressable sample wells. The addressable sample wells can contain other chemicals required for processing, synthesis or analyte detection.

To accomplish further processing, a reaction module is provided comprising either a reagent dispenser to dispense reagents (e.g. chemicals) into the addressable sample wells for a reaction or a detector to detect chemical reactions in the addressable sample wells.

The modules can be separately controlled or programmably controlled and integrated using a data processing and integration module. The data processing and integration module permits orchestrated processing to deliver addressable chemical wells or addressable sample wells to workstations so as to reduce processing time and permit, if so desired, parallel processing of addressable chemical wells or addressable sample wells. Typically, the storage and retrieval module, sample distribution module, sample transporter, reaction module and data processing and integration module are operably linked to facilitate rapid processing of the addressable sample wells or the addressable chemical wells.

The invention's system permits high-throughout processing of liquid samples, and storage and retrieval from vast stores of chemicals stored in solution. Typically, the storage and retrieval module has storage locations for at least 200,000 addressable chemical wells. To facilitate storage and retrieval, such wells are often organized or integrated into a plurality of addressable chemical plates that can hold multiple addressable chemical wells (or any other type of addressable well). The storage and retrieval module is operably linked to at least one plate buffer that loads and unloads the addressable chemical plates in a predetermined order that is either dependent or independent of the order of selection of the addressable chemical plates. This feature has the advantage of retrieving chemicals plates from the buffer in a manner that minimizes processing time at workstations downstream of the plate buffer, while minimizing retrieval time from the storage and retrieval module. The chemical well retriever is adapted to retrieve and replace selected addressable chemical plates and can be controlled by a program to reduce retrieval and replacement time of the chemical well retriever.

The storage and retrieval module can also provide storage locations for addressable sample wells. Usually addressable sample wells will be organized or integrated into a plurality of sample plates. It is desirable to design each sample plate with a standard footprint and preferably to match the sample plate footprint with the footprint of the chemical plate. The chemical well retriever can be adapted to store and retrieve selected addressable sample plates, as well as being adapted to retrieve addressable sample plates of a different thickness than the addressable chemical plates. Typically, a storage and retrieval module can house at least 20,000 addressable sample wells. This feature offers the advantage of reducing the types of retrievers required for storing and retrieving plates while permitting storage and retrieval of plates having wells of a different depth (hence the difference in plate thickness) and well volume.

According to the invention, it will be advantageous to reduce the volume of the chemical or sample processed. Liquid sample processing times benefit from volume reduction because liquid dispensing times are reduced, liquid aspiration times are reduced, diffusion times after addition of a reagent or sample are decreased and temperature control of a smaller volume is more uniform and consumable costs are greatly reduced. To reduce reagent (or chemical) volumes and permit dilution into smaller samples, the sample distribution module can include a liquid handler that comprises a plurality of nanoliter dispensers that can individually dispense a predetermined volume of less than approximately 2,000 nanoliters of liquid from a predetermined selection of addressable chemical wells into a predetermined selection of addressable sample wells. Preferably, a liquid handler comprises a plurality of nanoliter dispensers that can individually dispense a predetermined volume of liquid from a predetermined selection of said addressable chemical wells into a predetermined selection of said addressable sample wells. The nanoliter dispensers will typically have a center-to-center distance between each nanoliter dispenser of less than 9.0 mm. This feature permits liquid handling in conjunction with a variety of plate formats, as described herein. Different types of nanoliter and picoliter dispensers can be used as described herein and known in the art, as well as such dispensers developed in the future.

In many processing applications it is desirable to include a reaction module. The reaction module can be a reagent dispenser to permit chemical reactions, or addition of assay components (e.g., chemicals or cells), or a detector to detect chemical reactions, or changes in the physical properties of a sample in an addressable sample well. As described in greater detail herein, optical detection methods are often cost effective and permit high-throughput of samples. Preferably, the detector is optically disposed to launch light into selected addressable sample wells as part of an optical based detection module.

To facilitate the routing of addressable chemical or sample wells, the data processing and integration module can be programmed to route work to various workstations to minimize transport time or processing time associated with traveling to multiple workstations. The data processing and integration module can control the retrieval of selected addressable chemical wells, aspiration of selected chemicals from addressable chemical wells, transport along predefined routes, transport of addressable sample wells to the sample distribution module, dispensing into selected sample wells, routing the sample wells to a detector and collecting and storing data output from the detector. The data processing and integration module can also include an adaptive processing program to route the addressable sample wells and addressable chemical wells to workstations.

According to the present invention, ultra high-throughputs of liquid samples can be achieved using an integrated and operably linked system. Typically, an integrated system will integrate the modules of the system (e.g., the storage and retrieval module, sample distribution module, and data processing and integration module) and operably link such modules together with a sample transporter to process addressable sample wells at a rate of about 100,000 per day. Such ultra high-throughput rates are easier to achieve when the sample distribution module, sample transporter and reaction module are adapted to process miniaturized addressable sample wells having sample volumes of less than about 5 to 10 microliters in a well.

Storage and Retrieval Module

Figure 5:
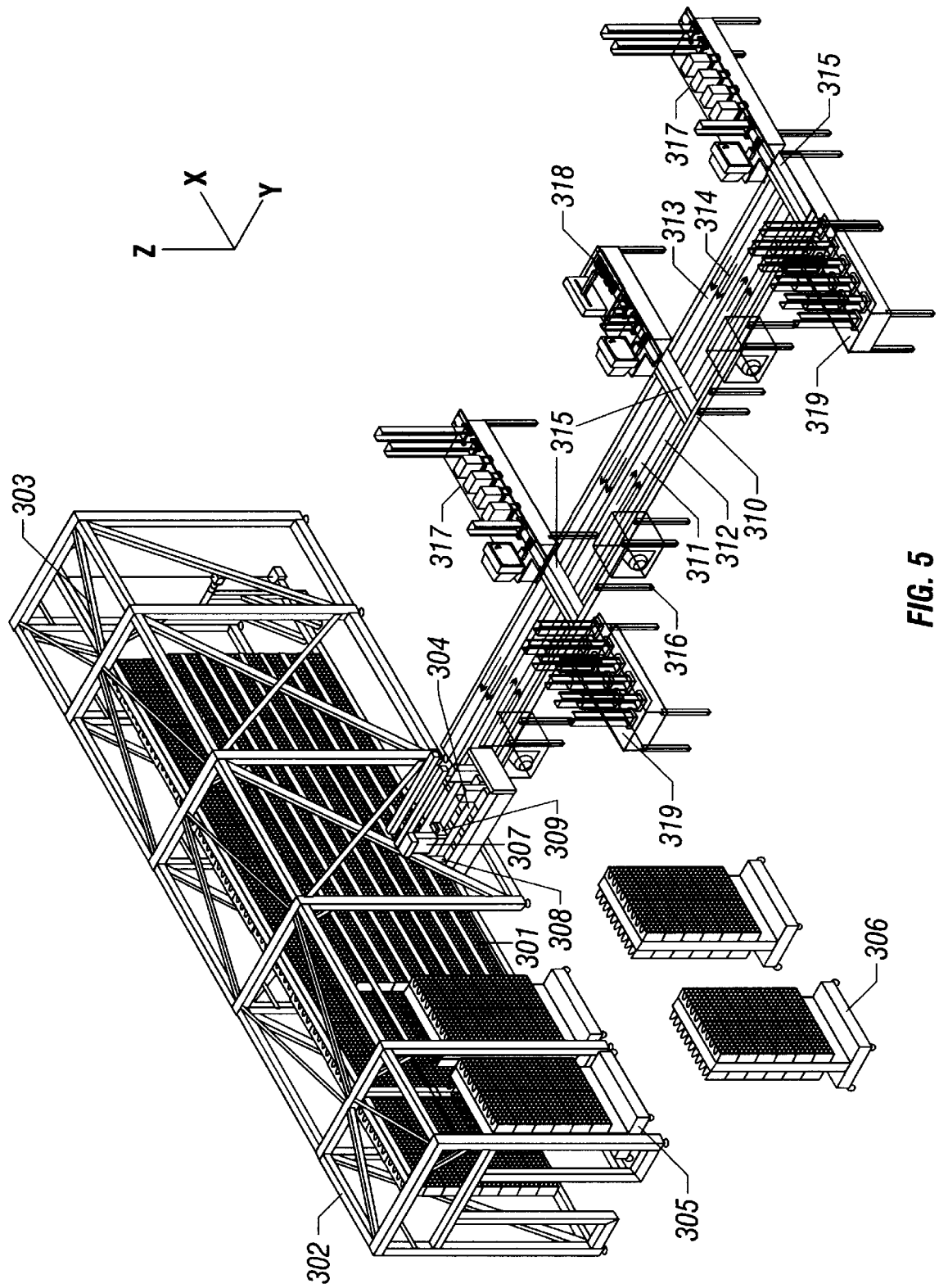
FIG. 5 shows one embodiment of a screening system.

The invention provides for a storage and retrieval module that can individually store a plurality of chemicals in solution. Typically, each chemical(s) is individually stored in a well. Typically, the wells can be addressed (addressable wells) by a computer, e.g., a means to instruct the storage or retrieval of a particular well. The computer instructions can be for an isolated single well(s) or for an array of wells on a plate. Plates and wells can be identified with an identification system such as a bar code. Well storage and retrieval can offer programmable selection of addressable chemical wells. One embodiment of the storage and retrieval module is shown in FIG. 5 that is operably linked to a sample transporter.

The storage and retrieval module also comprises a chemical well retriever that is computer-controlled to store and retrieve addressable wells in the storage and retrieval module. The chemical well retriever typically retrieves or stores addressable wells in a predetermined location with specified X and Z coordinates. Preferably, the chemical well retriever comprises a movable buffer that permits the chemical well retriever to load and unload multiple addressable wells without having to re-position the chemical well retriever. This allows the chemical well retriever to reduce its travel time and distance in the storage and retrieval module by carrying addressable wells (e.g., multiple arrays of wells as plates) during its travel in the storage and retrieval module rather than individually storing and retrieving each plate from a storage location and back to an unload location. Often the chemical well retriever will be able to handle plates with lids. Preferably, the chemical well retriever can handle any type of plate with a predetermined footprint. Preferably, the chemical well retriever will not use a robotic hand that grips the plate from the plate's side. Instead, it preferably retrieves a plate from the bottom, for example, with a platen. The chemical well retriever is usually not used as a sample transporter, as described herein. By providing a universal plate handler, the chemical well retriever provides for a flexible storage and retrieval system. One such example of a universal plate handler is described herein in the section describing screening applications of the invention.

Typically, the storage and retrieval module will handle plates with a standard footprint, either a predetermined standard or an industry standard. "Standard footprint" refers to the X,Y dimensions of a plate (length and width). Changes in storage and retrieval density can be achieved by varying the well-to-well distance. Preferably, the standard footprint is about 12.8 cm by about 8.5 cm. The plates can be housed in plate hotels that have dimensions that allow the plate to be stored and will provide sufficient space to permit a chemical well retriever to access a particular plate. Preferably, the chemical well retriever engages the plate from a bottom portion of the plate to reduce the dimensions of the plate hotel and eliminate dependency on a particular plate geometry. A chemical well retriever may be used as described herein for screening applications, as well as other devices capable of handling addressable wells as known in the art or developed in the future. The storage and retrieval module can have storage locations for at least about 25,000 to 50,000 addressable wells, about 500,000 addressable wells, or about 1,000,000 addressable wells, or about 10,000,000 addressable wells. The storage retrieval module can also include hotels on vertical movable members to access and sort the hotels.

In most embodiments it will be advantageous to integrate and operably link the storage and retrieval module with at least one other workstation, usually a sample transporter. The integration can be accomplished with a computer and associated control programs to instruct the chemical well retriever. For implementation with a liquid processing system, a data processing and integration module type device may be used as described herein, as well as other computing devices capable of integrating instrumentation as known in the art or developed in the future. Alternatively, the storage and retrieval module may be used without directly integrating it with another workstation by tracking addressable wells in groups and either mechanically or manually transporting the addressable wells to another work station where the addressable wells are identified. While this approach is feasible, especially for lower throughputs, it is not desirable for higher throughputs as it lacks direct integration that can lead to faster throughput times and can rely on manual operations that are more frequently subject to error, especially when processing large numbers of samples. Preferably, the storage and retrieval module can be integrated with other workstations and operate in a mode with minimal or substantially no manual operations related to transferring addressable wells to other work stations.

In some embodiments, especially storage and retrieval modules for temperature or atmosphere sensitive chemicals, it will be desirable to include an environmental control unit to modulate the environment of the storage and retrieval module (e.g., temperature, inert gases, and humidity of the storage and retrieval module). This can be accomplished by housing the storage and retrieval module, including the addressable well retriever, in an insulated casing with a suitable control unit(s). Preferably, a suitable control unit can maintain temperatures of either about 20 to 25 degrees Celsius, 0 to 5 degrees Celsius or -20 to -25 degrees Celsius. If desired, a dehumidifier can be included to remove moisture when either the chemicals or solvent have a tendency to absorb water. The storage and retrieval module is usually designed for semi-permanent storage (at least about 30 days to 120 days) and can accommodate retesting of chemicals.

Figure 3:
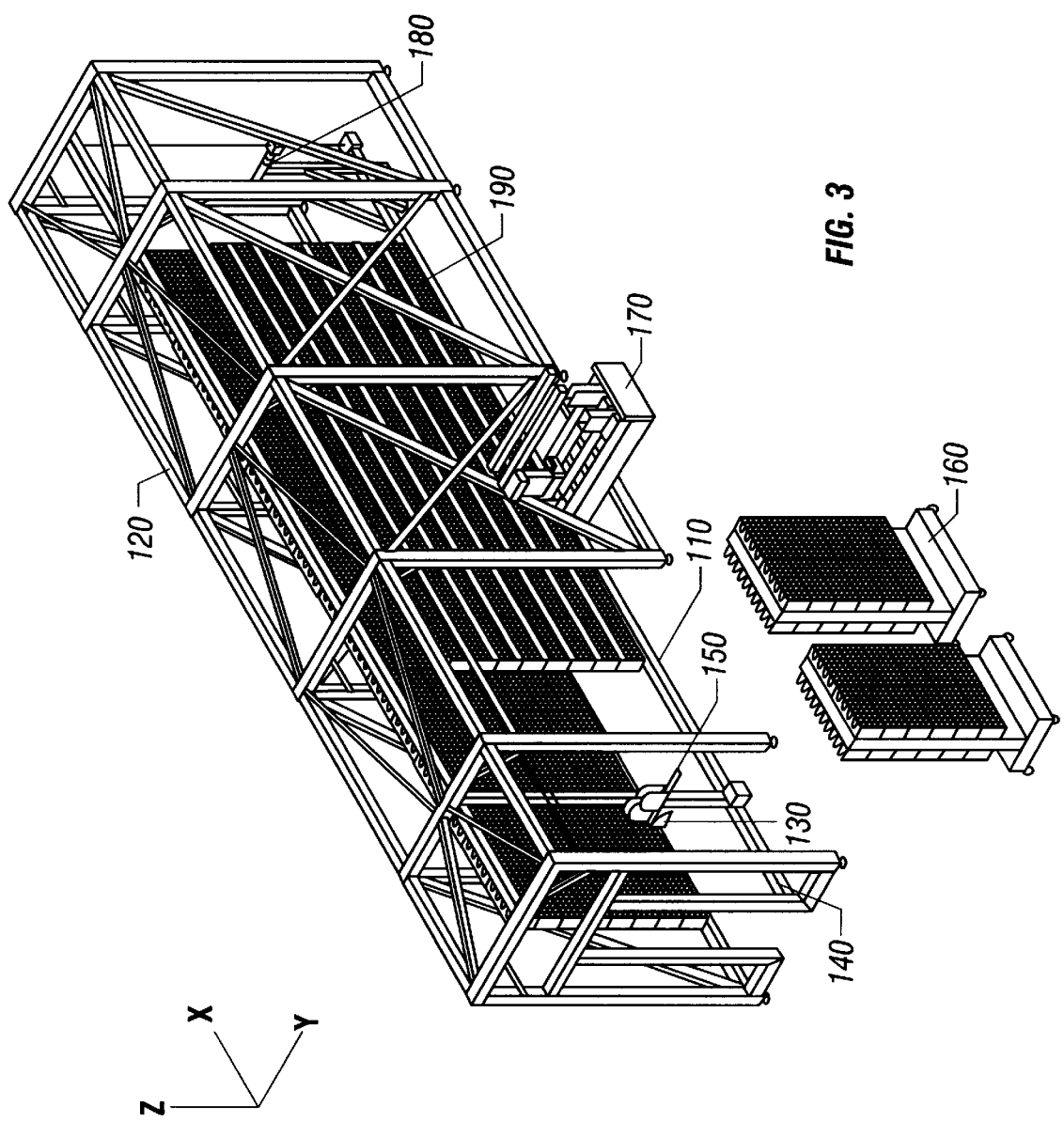
FIG. 3 shows one embodiment of a storage and retrieval module.

FIG. 3 shows one embodiment of a storage and retrieval module with hotels 110 and racks 120 for plates. A chemical well retriever 130 stores and retrieves addressable wells in plates from racks in hotels and is disposed on horizontal and vertical track 140 that can position the retriever. A chemical well retriever arm 150 that engages plates from the bottom to place plates on, and remove plates from, a rack. A removable store 160 that can be manually removed is also shown. The storage and retrieval module can be operably linked to a sample transporter at an ingress/egress junction 170.

Sample Distribution Module

The invention provides for a sample distribution module that can dispense or aspirate large numbers of solutions, usually small volume solutions. When the sample distribution module is integrated with a storage and retrieval module, it will be advantageous for the sample distribution module to both aspirate and dispense solutions with a liquid handler. In many instances, the sample distribution module will hold large numbers of different stock solutions of chemicals dissolved in aqueous or non-aqueous solvents (e.g., water or dimethylsulfoxide (DMSO)) in addressable chemical wells. To facilitate the rapid transfer of these stock solutions, it is desirable for the sample distribution module to aspirate a stock solution from an addressable well and dispense all or a portion of that solution into an addressable sample well or another addressable well. This sequence of events can be progammably controlled to ensure that the stock solution is aspirated from a pre-selected addressable chemical well and is dispensed into a pre-selected addressable sample well. This type of sample distribution module and process is useful for generating daughter plates from master plates or for transferring and diluting a chemical solution from a chemical plate to a sample plate. Typically, a sample transporter can be used to mechanically link the sample distribution module to a storage and retrieval module for the preparation of daughter plates. The sample distribution module can also be integrated to other components, for instance a conveyor transport system can link a sample distribution module to a reaction module.

It is particularly advantageous for the sample distribution module to handle plates of different well densities. This is usually accomplished by a sample distribution module that can recognize plates with a standard footprint. Plates having different well densities but similar standard footprints can then be processed. When handling plates of different densities, it is desirable to track the plate density with a database linked to a plate bar code (or some other plate identification system, e.g., radio frequency) and to provide a sample distribution module that can register the bar code. When used with a data processing and integration module controller, the bar code can easily reference a plurality of plate and well information from the data store, such that no encoded data is necessary on the bar code itself. The sample distribution module can then be properly instructed to aspirate or dispense in a manner that corresponds to the well density of the plate. This permits aspiration at one well density and dispensation at a second well density. Thus, compression of low density plates can occur by the transfer of liquids to a higher density plate and expansion of high density plates can occur by transfer of liquids to a lower density plate. This feature advantageously allows a sample distribution module to functionally interface with other workstations that may individually utilize plates of different well density.

For example, traditional 96-well plates can be used to store chemical solutions in master plates in a storage and retrieval module. The sample distribution module aspirates a predetermined volume of chemical solution from all the addressable chemical wells of a master plate. The sample distribution module then dispenses a predetermined volume of chemical solution into a pre-selected portion of the addressable wells of a 384 daughter plate (i.e. compression). This process can be repeated to construct replicate arrays on the same or different daughter plate.

Aspiration or dispensation into plates of different densities can be accomplished by automated orthogonal positioning of a plate. Typically, the plates are securely disposed on an orthogonal positioner that moves the wells of a plate with a first density in an X,Y position with respect to the X,Y position of the liquid handler. Usually, the liquid handler will have an array of aspiration and/or dispensation heads, or both. Many aspiration/dispensation heads can operate simultaneously. The orthogonal positioner will align each well with the appropriate dispensing head. Preferably, a predetermined location (e.g., center) of a pre-selected addressable well will be aligned with the center of a dispensing head's fluid trajectory. Other alignments can be used, such as those described in the examples. With a head substantially smaller than a well diameter, orthogonal positioning permits aspiration or dispensation into plates of different densities and well diameters.

An orthogonal positioner can typically match an array of dispensing heads with an array of wells in X,Y using a mechanical means to move the wells into position or the liquid handler (e.g., dispensing heads) into position. Preferably, arrays of wells on a plate are moved rather than the liquid handler. This design often improves reliability, since plates are usually not as heavy or cumbersome as liquid handlers, which results in less mechanical stress on the orthogonal positioner and greater movement precision. It also promotes faster liquid processing times because the relatively lighter and smaller plates can be moved more quickly and precisely than a large component. The mechanical means can be a first computer-controlled servo motor that drives a base disposed on a X track and a second computer-controlled servo motor that drives a Y track disposed on the X track. The base can securely dispose a plate and either a feedback mechanism or an accurate Cartesian mapping system, or both that can be used to properly align wells with heads. Other such devices, as described herein, known in the art or developed in the future to accomplish such tasks can be used. Usually, such devices will have an X,Y location accuracy and precision of at least ±0.3 mm in X and ±0.3 mm in Y, preferably of at least ±0.09 mm in X and ±0.09 mm in Y, and more preferably of at least ±0.01 mm in X and ±0.01 mm in Y. It is desirable that such devices comprise detectors to identify the wells or plates being orthogonally positioned. Such, positioners for predetermined X, Y coordinates, can be made using lead screws having an accurate and fine pitch with stepper motors (e.g., Compumotor Stages from Parker, Rohnert Park, Calif., USA). Such motors can be computer-controlled with the appropriate electrical inputs to the stepper motor. Orthogonal positioners can be used with other components of the invention, such as the reagent dispenser or detector to position sample plates. Alternatively, the liquid handler can be disposed on a Z-positioner, having an X,Y positioner for the liquid handler in order to enable precise X,Y and Z positioning of the liquid handler (e.g., Linear Drives of United Kingdom).

A reference point or points (e.g., fiducials) can be included in the set up to ensure that a desired addressable well is properly matched with a desired addressable head. For instance, either the plate, the orthogonal positioner or the liquid handler can include a reference point(s) to guide the X,Y alignment of a plate, and its addressable wells, with respect to the liquid handler. For example, the liquid handler has a detector that corresponds in X,Y to each corner of a plate. The plate has orifices (or marks) that correspond in X,Y to the liquid handler's position detectors. The plate's orifices allow light to pass or reflect from a computer-controlled identification light source located on the orthogonal positioner in the corresponding X,Y position. Optical locators known in the art can also be used in some embodiments (PCT patent application WO91/17445 (Kureshy)). Detection of light by the liquid handler emitted by the orthogonal positioner verifies the alignment of the plates. Once plate alignment is verified, aspiration or dispensation can be triggered to begin. Stepper motors can be controlled for some applications as described in U.S. Pat. No. 5,206,568 (Bjornson).

The liquid handler will also typically be disposed on a Z-dimensional positioner to permit adjustments in liquid transfer height. This feature allows for a large range of plate heights and aspirate and dispense tips, if desired, to be used in the sample distribution module. It also permits the dispense distance between a well surface, or liquid surface in a well, and a liquid handler to be adjusted to minimize the affects of static electricity, gravity, air currents and to improve the X,Y precision of dispensation in applications where dispensation of a liquid to a particular location in a well is desired. Alternatively, plates can be positioned on a Z-dimensional positioner to permit adjustments in liquid transfer height. Static neutralizing devices can also be used to minimize static electricity. Generally, the liquid transfer height will be less than about 2 cm. Preferably, small volumes will be dispensed at a liquid transfer height of less than about 10 mm, and more preferably less than about 2 mm. Occasionally, it may be desirable to contact the tips with a solution in a controllable fashion, as described herein or known in the art The sample distribution module can be structured to minimize contamination. The liquid handler can be constructed to offer minimum tip exposure to liquids using a sensor (e.g., acoustic, and refractive index). For instance, probe contact with a liquid surface can be reduced by providing a liquid sensor on the dispensing tip, such as a conductivity or capacitance sensor, that forms a feedback system to control the entrance of a tip into a liquid. Carry-over from one plate to another plate can be kept to acceptable level with a blow-out of the tip and minimizing tip penetration into a liquid with a sensor. Preferably, a sample distribution module will include a means for volume control, and washing the liquid handler. Alternatively, the data processing and integration module can calculate the remaining levels in the wells based on usage and predicted evaporation, in order to deploy the tips to suitable measured distance and can be adjusted for plated of different heights.

The sample distribution module will often include a plate buffer (e.g., a stacker). The buffer acts as a temporary storage depot for addressable wells or plates. Preferably, plate retrieval from a plate buffer will be predetermined. Plate retrieval can be either dependent or independent of the order of selection and can be computer-controlled. Preferably, the data processing and integration module will include a routine to reduce storage and retrieval time, as described herein. It is also desirable to provide for a routine to reduce transport time of any well retriever used in astorage and retrieval module. By allowing a plate buffer to acquire addressable wells as they are retrieved by an storage and retrieval module, the transport routine of the storage and retrieval module can be designed to minimize retrieval time rather than to retrieve addressable wells in a sequential order.

A stacker can be used as a plate buffer. Typically, a plate stacker will up/down stack plates of a standard footprint and with different densities (e.g., deep well (e.g., 5 cm) or shallow well microplates of 96 (e.g., 1 cm), 384, 864, and 3,456 (e.g., 1 to 3 mm) well format or greater (e.g., 6,912 or 13,024)). A computer control system will track stacker contents. The stacker can optionally include a delidder to remove lids on lidded plates.

The operation of the sample distribution module will usually be highly flexible to satisfy the needs of different liquid processing applications. Predefined operations can be made available for selection by an end user, or end users may create an entirely new method. Operations can be performed on a wide variety of plates and batch sizes of plates can vary. Sample plates and chemical plates may be selected with a different format from distribution plates (e.g., daughter plates). The sample distribution module will usually have the ability to pool samples. The report of success, failure and errors can be sent back to a control processor or to a display for the end user. The sample distribution module will typically provide for a stand alone mode and can be preferably integrated with a data processing and integration module.

In one embodiment, the liquid handler can comprise a plurality of nanoliter dispensers that can individually dispense a predetermined volume. Typically, dispensers are arranged in two-dimension array to handle plates of different well densities (e.g., 96, 384, 864 and 3,456).

Usually, the dispensed volume will be less than approximately 2,000 nanoliters of liquid that has been aspirated from a predetermined selection of addressable chemical wells and dispensed into a predetermined selection of addressable sample wells. Preferably, nanoliter dispensers can dispense less than approximately 500 nanoliters, more preferably less than approximately 100 nanoliters, and most preferably less than approximately 25 nanoliters. Dispensing below 25 nanoliters can be accomplished by dispensers described herein. Preferred, minimal volumes dispensed are 5 nanoliters, 500 picoliters, 100 picoliters, 10 picoliters. It is understood that dispensers capable of dispensing such minimal volumes are also capable of dispensing greater volumes. The maximal volume dispensed will be largely dependent on the dispense time, reservoir size, tip diameter and dispenser type. Maximum volumes dispensed are about 10.0 microliters, 1.0 microliters, and 200 nanoliters. Preferably, such liquid handlers will be capable of both dispensing and aspirating. Usually, a nanoliter dispenser (or smaller volume dispenser) comprises a fluid channel to aspirate liquid from a predetermined selection of addressable wells (e.g., chemical wells). Liquid handlers are further described herein, and for some volumes, typically in the microliter range, suitable liquid dispensers known in the art or developed in the future can be used. It will be particularly useful to use liquid handlers capable of handling about 1 to 20 microliter volumes when it is desired to make daughter plates from master plates. Preferably, in such instances a liquid handler has a dispensing nozzle that is adapted for dispensing small volumes and can secure a tip having a fluid reservoir.

In one embodiment nanoliter dispensers comprise solenoid valves fluidly connected to a reservoir for liquid from an addressable chemical well. The fluid reservoir can be a region of a dispenser tip that can hold fluid aspirated by the nanoliter dispenser. Usually, a tip reservoir will hold at least about 100 times the minimal dispensation volume to about 10,000 times the dispensation volume and more preferably about 250,000 times the dispensation volume. The solenoid valves control a positive hydraulic pressure in the reservoir and allow the release of liquid when actuated. A positive pressure for dispensation can be generated by a hydraulic or pneumatic means, e.g., a piston driven by a motor or gas bottle. A negative pressure for aspiration can be created by a vacuum means (e.g., withdrawal of a piston by a motor). For greater dispensing control, two solenoid valves or more can be used where the valves are in series and fluid communication.

In another embodiment, nanoliter dispensers comprise an electrically sensitive volume displacement unit in fluid communication to a fluid reservoir. Typically, the fluid reservoir holds liquid aspirated from an addressable chemical well. Electrically sensitive volume displacement units are comprised of materials that respond to an electrical current by changing volume. Typically, such materials can be piezo materials suitably configured to respond to an electric current. The electrically sensitive volume displacement unit is in vibrational communication with a dispensing nozzle so that vibration ejects a predetermined volume from the nozzle. Preferably, piezo materials are used in dispensers for volumes less than about 10 to 1 nanoliter, and are capable of dispensing minimal volumes of 500 to 1 picoliter. Piezo dispensers can be obtained from Packard Instrument Company, Connecticut, USA (e.g., an accessory for the MultiProbe 104). Such devices can also be used in other liquid handling components described herein depending on the application. Such small dispensation volumes permit greater dilution, conserve and reduce liquid handling times.

In some embodiments, the liquid handler can accommodate bulk dispensation (e.g., for washing). By connecting a bulk dispensation means to the liquid handler, a large volume of a particular solution to be dispensed many times. Such bulk dispensation means are known in the art and can be developed in the future.

In most embodiments, it will be advantageous to integrate and operably link the sample distribution module with at least one other workstation, usually a sample transporter. The integration can be accomplished with a computer and associated control programs to instruct the liquid handler. For implementation with a liquid processing system, a data processing and integration module type device may be used as described herein, as well as other computing devices capable of integrating instrumentation as known in the art or developed in the future. Alternatively, the reaction module may be used without directly integrating to another workstation by tracking addressable wells in groups and either mechanically or manually transporting addressable wells to another work station where the addressable wells are identified. For instance, the reaction module may be directly integrated and operably linked to a storage and retrieval module and sample transporter, and indirectly linked to a separate detector through manual operations. While this approach is feasible, especially for lower throughputs, it is not desirable for higher throughputs as it lacks direct integration that can lead to faster throughput times. Manual operations also are more frequently subject to error especially when processing large numbers of samples. Preferably, the reaction module can be integrated with other workstations and operate in a mode with minimal or substantially no manual intervention related to transferring addressable wells to other work stations.

Figure 4:
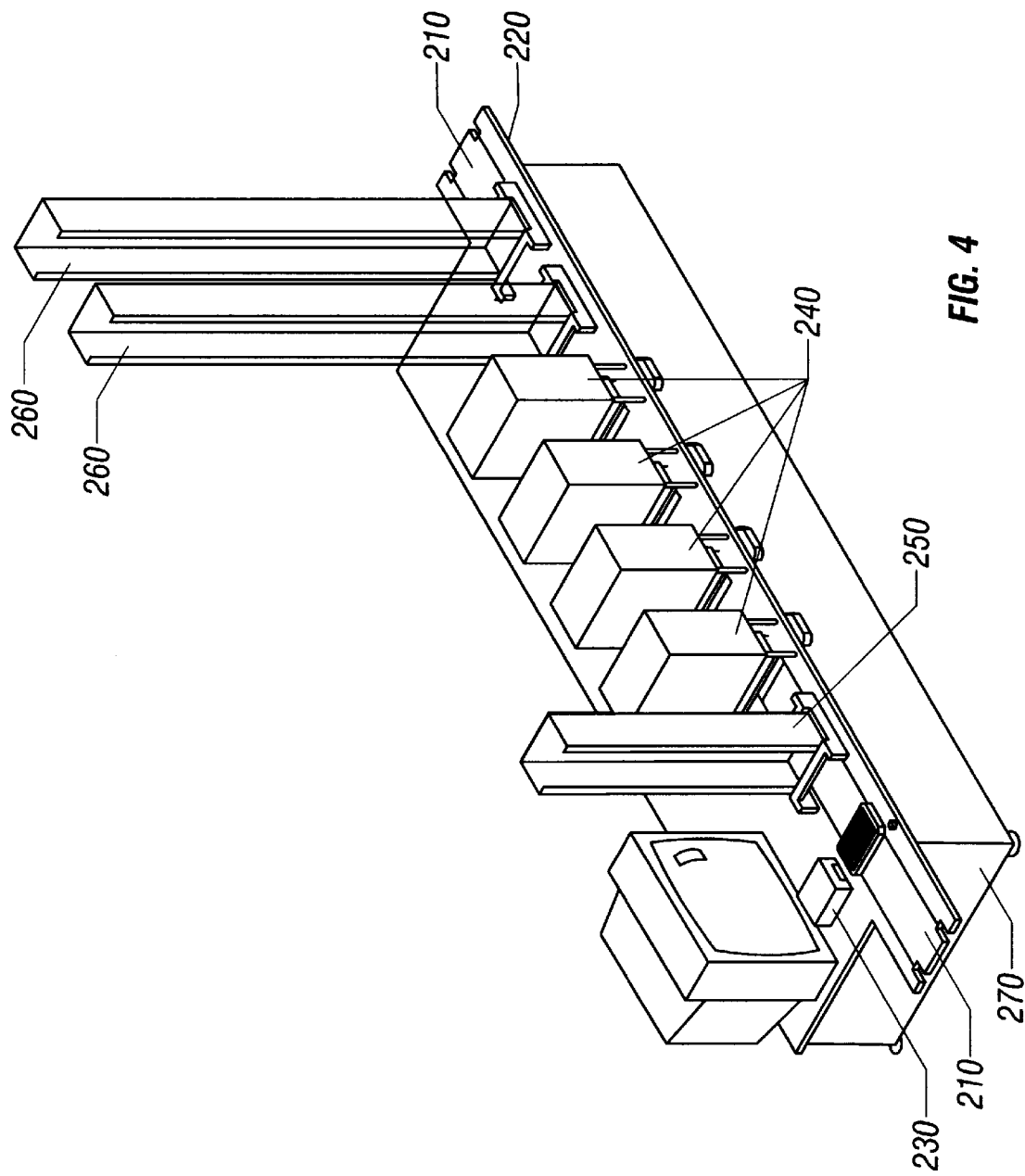
FIG. 4 shows one embodiment of a sample distribution module.

FIG. 4 shows one embodiment of a sample distribution module with a conveyor means 210 comprising a rotating band that runs the length of the sample distribution module platform 220 and can transport plates. A bar code reader 230 registers plates on the conveyor means. A series of liquid handlers 240 are disposed along the conveyor means. Addressable wells in four chemical plates can be simultaneously aspirated from the liquid held in the liquid handlers, and then dispensed in additional plates. Lids can be removed or replaced by the delidder/lidder 250. Proximal plate stacker 260 and distal plate stackers 260 can be used temporarily to store plates, such as chemical and sample plates, which can facilitate plate selection. The sample distribution module can be operably linked to a sample transporter at an ingress/egress junction 270.

Sample Transporter

The present invention provides for a sample transporter that can transport addressable wells on plates, or units of work to work stations. A sample transporter can use series or parallel routing, as well as combination routing that uses a combination of series and parallel processing. Such combinations can reduce transport times by offering programmed, flexible routing to minimize transport times between work stations. This also permits enhanced processing time at workstations to reduce overall processing times. Multiple parallel pathways can also enhance flexible processing. Typically, the sample transporter will comprise at least two parallel lanes and preferably at least four parallel lanes. Typically, a sample transporter lane can transport addressable wells (e.g., addressable chemical or sample wells) in both directions, bi-directional transport (e.g., north and south movement in the same lane but at different times) by changing the transport direction. It will, however, be desirable in some instances to dedicate one or more lanes, to unidirectional transport to reduce transition times associated with changing transport direction. Each lane can be disposed, with one or more intersections that permits transport of addressable well(s) in and out of each lane. Such intersection can be used to route addressable wells to workstations. Typically, at least one or two workstations will be operably linked to the sample transporter, however, more workstations (e.g., 3 to 6 or more) can be operably linked to obtain maximum benefit from flexible routing with intersections and parallel processing of complex processes.

In one embodiment, the sample transporter is a reduced friction, ortho-multilane conduit. In this embodiment, the sample transporter uses multiple lanes to transport addressable wells straight to a destination point, preferably not in a rotary fashion. Such lanes can be used to create processing grids comprised of intersections and highways to direct the trafficking of addressable wells. Preferably, such grids are located in the same plane but multi-plane grids can be used. Although transport in each lane can be stopped to permit passage of a plate through an intersection, each lane is a continuous conduit that allows plates to flow. The plates can rest on a moving surface of the conduit or can be secured either on the conduit's surface or side, so long as the conduit's surface allows for transport. For ease of overall operation, the flow of the wells can be computer-controlled. In some limited, simple applications a lane may be simply activated or deactivated by the presence of an object as a plate without utilizing a computer. Preferably, the conduit uses a surface material to reduce friction to minimize the force required for movement and to increase the smoothness of transport to reduce spills, contamination, and to allow for settling of well contents if so desired. Such materials include Teflon™ and Delrin™. The materials can be used as rollers or moveable bases connected to a track that forms a lane. Often the reduced friction, ortho-multilane conduit will be operably linked to a plate buffer disposed in a workstation to facilitate transport and allow for flexible routing of plates, such as chemical or sample plates or might form a buffer or queue itself.

The transport capacity of the sample transporter should be commensurate with the intended throughput of the system to which it is operably linked. For instance, the rate of plate transport for standard plates is typically at least about 6 meters per minute, and preferably at least about 15 meters per minute. Lanes are typically about 15 to 25 cm in width and preferably about 1 to 5 meters based in length that may be based on queuing requirements. The sample transporter will typically support overall throughput rates of about 40,000 to 60,000 wells per day, preferably about 80,000 to 120,000 wells per day and more preferably about 250,000 to 500,000 wells per day. Larger transport throughputs can also be achieved between about 1 million and 10 million addressable wells, depending on well density. By using multiple lanes in conjunction with fast plate transport rates such throughputs can be achieved.

As an example of the design and operation of the sample transporter, the sample transporter can be configured in a continuous parallel processing drug screening system to process samples more efficiently, particularly liquid samples. This type of configuration can improve transport of plates in a system with multiple work stations to more conveniently achieve ultra high-throughput rates. A continuous parallel processing drug screening system can provide for one or more of these features: fixed work unit, flexible routing, adaptive routing, queues, access to workstations, and parallel or series processing. The overall design of the continuous parallel processing drug screening system offers flexible delivery and presentation of work, especially for screening for useful chemicals, chemical synthesis, analysis of environmental samples or analysis of biological samples (e.g., medical diagnostics).

Work in the system is divided in two types of elements: 1) work that is directed to a plurality of workstations and 2) work that is organized into specific "work units," which have a common physical form (e.g., plates). Some plates are used for storage, while other plates that are generally similar are used for screening. All operations are commanded by a supervisory control computer(s), such as a data processing and integration module. The computers receive their work schedule from a data store which gives detailed instructions for workstations and for each work unit. The structure of the data store can be of the type provided herein or those suitable data stores known in the art.

Workflow can be divided according to the major physical organization of the system. The system can comprise a chemical storage and retrieval module, a sample transporter, and various other workstations. FIG. 5 shows an isometric view of a processing system.

Storage of work unit, such as plates, is accomplished with a rack system. A plurality of individual storage shelves is contained in a modular hotel 301. Modular hotels are mounted on an adjustable track system and attached to the store framework 302. The capacity of each hotel is typically about 20 to 40 shelves. The hotels are arrayed in the store in two dimensions, referred to as X and Z. Two opposing arrays of shelves are provided, with their entries on opposite sides of a central aisle 303.

Traveling along the 'X' axis in the central aisle is a robotic means to store and retrieve work units. The robotic means can pick and place work units in any location in the storage and retrieval module. The robotic means comprises an integrated buffer to optimize the X axis travel. This can allow for the most efficient pick or place order via a programmed sequence of retrieval commands. The robotic means can operate on a plurality of plates without returning to the center input/output location except when the integrated buffer is fully loaded. The robotic end actuator also travels in the vertical or 'Y' direction. A platen device moves in the 'Y' axis to obtain units of work from the shelves, as described herein and can be used as a plate retrieval means as known in the art or developed in the future.

Some sections of a storage and retrieval module can optionally contain removable capacity (e.g., hotels) 306. The removable hotels are the same as fixed hotels, but are mounted to carts, which physically lock into place 305. Movable, but securable, carts are used to transfer large quantities of work into and out of the store. They can be used to replenish the contents, or can provide blank media and collect finished work in a particular application, such as a drug screening applications.

At the ingress and egress location 304 in the center of the conveyor, there is a stacking or sorting means that can stack or sort work units. For instance, at the ingress, an upstacker creates a stack, which is transferred as a group to the robotic means. These units of work are then individually placed in the shelves of the storage and retrieval module. At the egress position, a down stacker 308 to separate units of work, and a sorting means 309 reorders the work units, so that units of work are presented to a sample transporter in the exact order required.

The sample transporter 310 preferably connects to the storage and retrieval module near the center at the ingress and egress location 304 to reduce travel time. The sample transporter can comprise a conveyor to transfer work units to workstations, and unload and offload means to assist the transfer of work units from devices, via photocells, a work unit inventory system (e.g., bar codes or other system). The sample transporter is capable of moving a unit at a rapid speed from any workstation to any other random workstation. It offers flexible parallel routing, unlike robotic means that only offer serial routing. This is a distinct advantage in drug discovery applications, and it can improve the reliability and flexibility of rapid liquid processing.

The work unit transport can be divided into four lanes as FIG. 5. The queuing lane 311 prevents work unit build up by providing for a queuing lane for a workstation. The passing lane 312 permits rapid transport of work units to a distant workstation. Similarly, returning lanes provide a passing lane 313 and a queuing lane 314.

At predetermined locations along a conveyor are lift and transfer mechanisms (LAT) 315. Each LAT can move a unit from one lane to another under program control. A LAT is able to transfer a work unit from the conveyor and to present it to a workstation or another conveyor. It can transfer plates from the workstation to the conveyor in a similar manner. Typically, LATs are belt driven conveyors that intersect with a lane. The belts are located below the plane of a lane when the LAT is not in operation. Upon activation a LAT is raised to provide contact of the belts with the bottom of the plate to be transferred. The belts then transfer the plate to a predetermined location. The LAT is then lowered thereby releasing the plate to a workstation or conveyor.

Based on the result obtained at one workstation, conditions, or loading, the supervisory control system can order the transport system to move units to different workstations. In this manner, a busy or malfunctioning workstation can be avoided. This adaptive routing capability is particularly advantageous in an automated process, especially liquid processing, and can be implemented using a supervisory control system for its operation, as described herein.

The supervisory control system can be implemented as a portion of the data processing and integration module and contains computer devices for control and data store for information storage and retrieval. The supervisory control system in the preferred embodiment includes specialized computers for real-time control. These are typically programmable logic controllers, which are connected by network or serial interface to a supervisor computer. The supervisor computer in the supervisory control system interfaces with the programmable logic controllers to provide commands which direct the electromechanical devices in the sample transporter to move and divert plates. It also receives information from the programmable logic controllers on the current state of the sample transporter. The supervisor computer determines its actions based on information in the data processing and integration module data store, and directly connected bar code readers. Each unit of work (plate) has a unique identifier which is referenced by the data processing and integration module database. The sample transporter contains a number of decision points, or locations where the supervisory control system must determine the plates next routing. A reader at each decision point allows the supervisory computer to give optimal commands to the programmable logic controller. Some decision points can omit the reader, if information is available elsewhere, i.e. stack and queue data in the supervisory control system itself.

The chemical transporter itself is preferably constructed in a integratible sections. For example, in FIG. 5, there are three sections shown. Within these three sections, there are six workstations defined and five shown. The ingress/egress junction where the screening sample transporter connects to the storage and retrieval module is also shown. Larger configurations can include additional transport sections to support additional workstations. Each transport section is usually individually powered and controlled. Drive motors and control wiring are located on the bottom of each section 316.

The chemical transporter can accommodate a large number of work units simultaneously. Typically, the inventors have had as many as 36 plates queued or moving on each transport section. Usually the screening sample transporter will accommodate at least 10 work units on a moving surface(s), preferably at least 25 work units, more preferably at least 50, or at least 100 work units. Work that is waiting for processing at a workstation can be queued on the screening sample transporter, such that a complete batch of work units is available as soon as the workstation machine becomes available. The length of each conveyor section 310 is directly related to the maximum number of queued units expected at each workstation. In the present embodiment, the sections are approximately nine feet in length, which allows the queuing of sixteen work units the size of standard footprint (e.g., 8.5 cm by 12 cm) plates. Conveyors known in the art can be used in some embodiments (e.g. slip-torque conveyor system by Shuttleworth, IN, USA).

The chemical transporter is designed to reduce bottlenecks in the simultaneous processing at the various workstations. Work units can usually be transferred on or off the screening sample transporter at a rate of approximately one, every two to four seconds, at each workstation, although faster times of preferably one every 500 to 1,000 milliseconds are contemplated. Since the transport is parallel in nature, each of the six shown workstations can operate asynchronously.

The workstations shown in FIG. 5 represent typical devices that can be used in liquid processing and served by workflow instructions. The workstation shown in the bottom right corner is a work unit replication device or sample distribution robot 317. The sample distribution robot is one form of sample distribution module as described herein. The sample distribution robot represents a typical workflow within the workstation. The sample distribution robot is herein operably linked to the transport through a LAT 315 and can be integrated via a computerized control. It can include a number of operations, such as delidding, four aspirate/dispense stations, and two stacker/destackers. The work flow in the workstation provides for a processing of units. First in, last out processing has numerous advantages in the processing of units, including the ability to match lids to the appropriate work unit (if lids are desired), and the ability to retain master work units when replicated work units are returned to the screening sample transporter.

With reference to FIG. 5, the workstation at 318 is a hit profiling robot 318. The hit profiling robot is another form of a sample distribution module, as described herein. The hit profiling robot adds a single well access device for aspiration/dispense of a work unit. Also shown is a workstation that provides high capacity stacking 319. Additional units, such as a manual workstation, screening workstations, and other devices can also be included as part of this invention. Their work flow is similar to the devices already described.

Figure 6A:
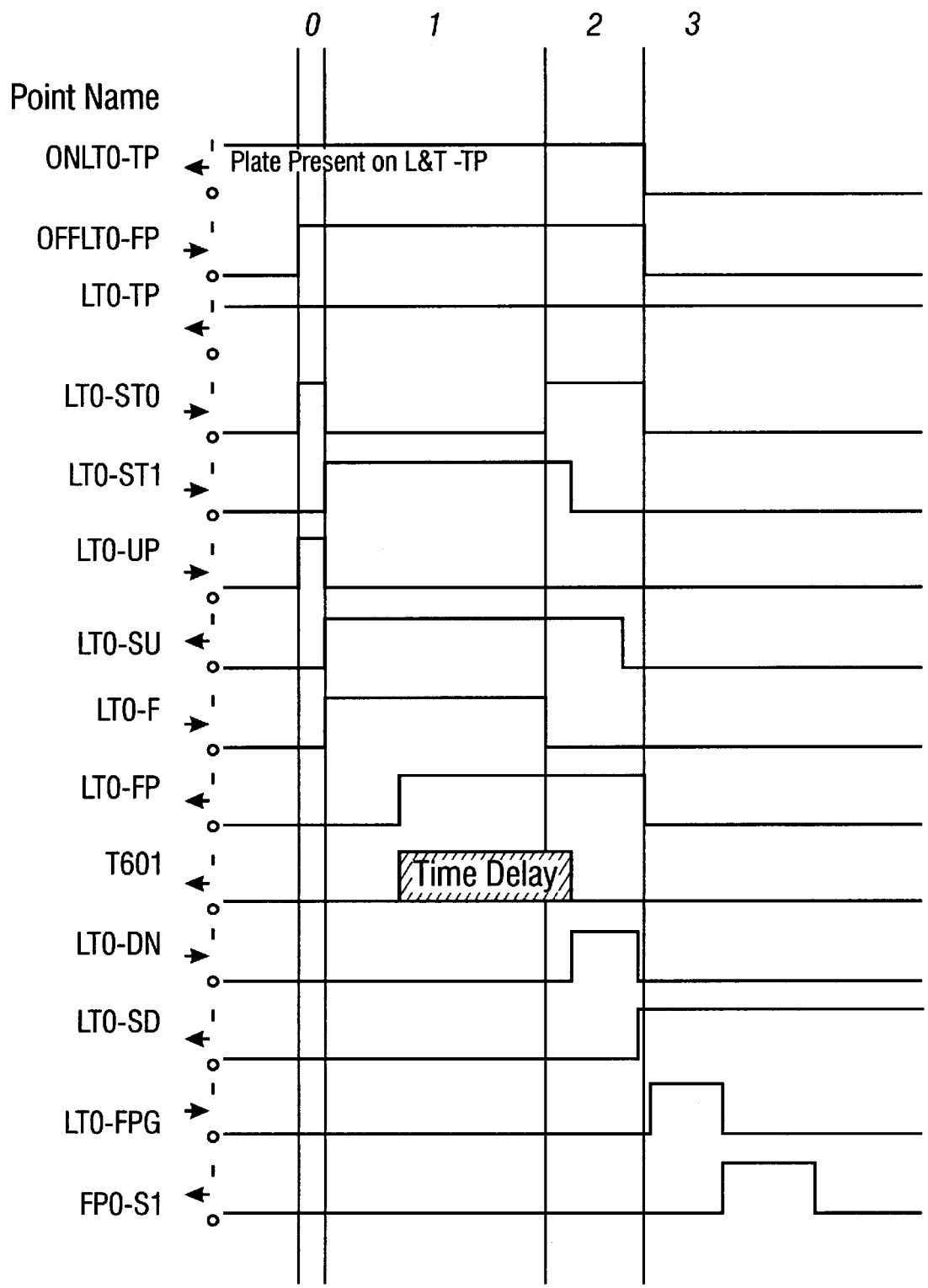
FIG. 6A and 6B show embodiments of a workstation interface.

A "handshaking logic" can be used between a lift and transfer mechanism and the sample transporter or a data processing and integration module and is described in FIG. 6A. Such logic can include all or at least five of the represented logic steps and more preferably at least eight logic steps to control the timing of the lift and transport. The following table describes the I/O Point definitions given in FIG. 6A. These I/O Points are defined for each lift and transfer station on the sample transporter. Each lift and transfer station can move units of work (e.g., plates) from one lane to another, or transfer a plate to a work center located to either side.

TABLE 1

| I/O Point in FIG. 6A | Function | Lane |
| --- | --- | --- |
| ONLT0-TP | Request to place plate on LT0 from TP lane | To/Pass |
| OFFT0-FP | Request to have plate exit from LT0 on the FP lane | From/Pass |
| LT0-TP | Sense the presence of a plate at TP lane | To/Pass |
| LT0-ST0 | Lift & Transfer Unit 0 State 1 bit | |
| LT0-UP | Make the L & T 0 go up | |
| LT0-SU | Sense when the LT0 unit is up | |
| LT0-F | Turn L & T 0 motor on in the F direction | |
| LT0-FP | Sense a plate on LT0 in the FP lane | From/Pass |
| T601 | Timer for stop delay | |
| LT0-DN | Make LT0 go down | |
| LT0-SD | Sense LT0 is down | |
| LT0-FPG | Control for LT0 lane FP exit gate | |
| FP0-S1 | Lane FP sensor | From/Pass |

Figure 6B:
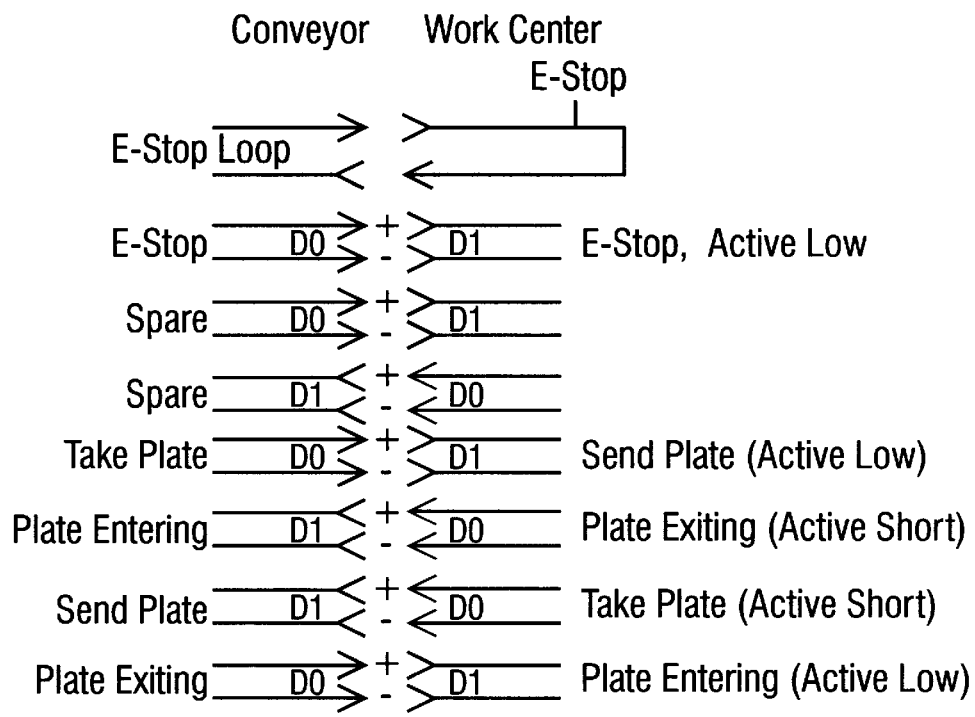

FIG. 6B shows the electrical specifications used to integrate a work station (work center) with asample transporter. All of the represented pins can be used for the physical handshake connection between a work station and a sample transporter. Preferably, at least five of the represented pins are used and more preferably at least eight logic represented pins are used to integrate a work station with a sample transporter or other module.

While the screening sample transporter provides parallel processing of multiple work units waiting or moving to multiple workstations, the workstations themselves also can provide parallel operations. The sample distribution robot shown has four parallel aspirate/dispense devices, and all can be operable on a different unit at the same time. This is one means of increasing throughput of the system. Since the screening sample transporter can accommodate six or more workstations, and each workstation can simultaneously operate on four or more plates, a large number of parallel operations can be performed at any instant.

In addition, a sample transport means can be used to operably link components of a liquid processing system or components within a module. Such a sample transport means can include conveyor belts, articulated robotic arms, slide mechanisms, automated guided vehicles and the like as known in the art, or developed in the future.

Reaction Module

Reagent Dispenser

In one embodiment, the invention provides for a reaction module that is a reagent dispenser to provide reagents (e.g. chemicals to be tested or targets) to the addressable wells in a predetermined manner. The reagent dispenser is integrated to other workstations with the data processing and integration module and operably linked with the sample transporter. One or more reagent dispensers can be operably linked to the sample transporter as shown in FIG. 5. Preferably, the reagent dispenser is of the type described in the Examples. Other reagent dispensers that are compatible with the data processing and integration module and the sample transporter (if operable linkage to the sample transporter is desired) can be used as known in the art or developed in the future.

Figure 7:
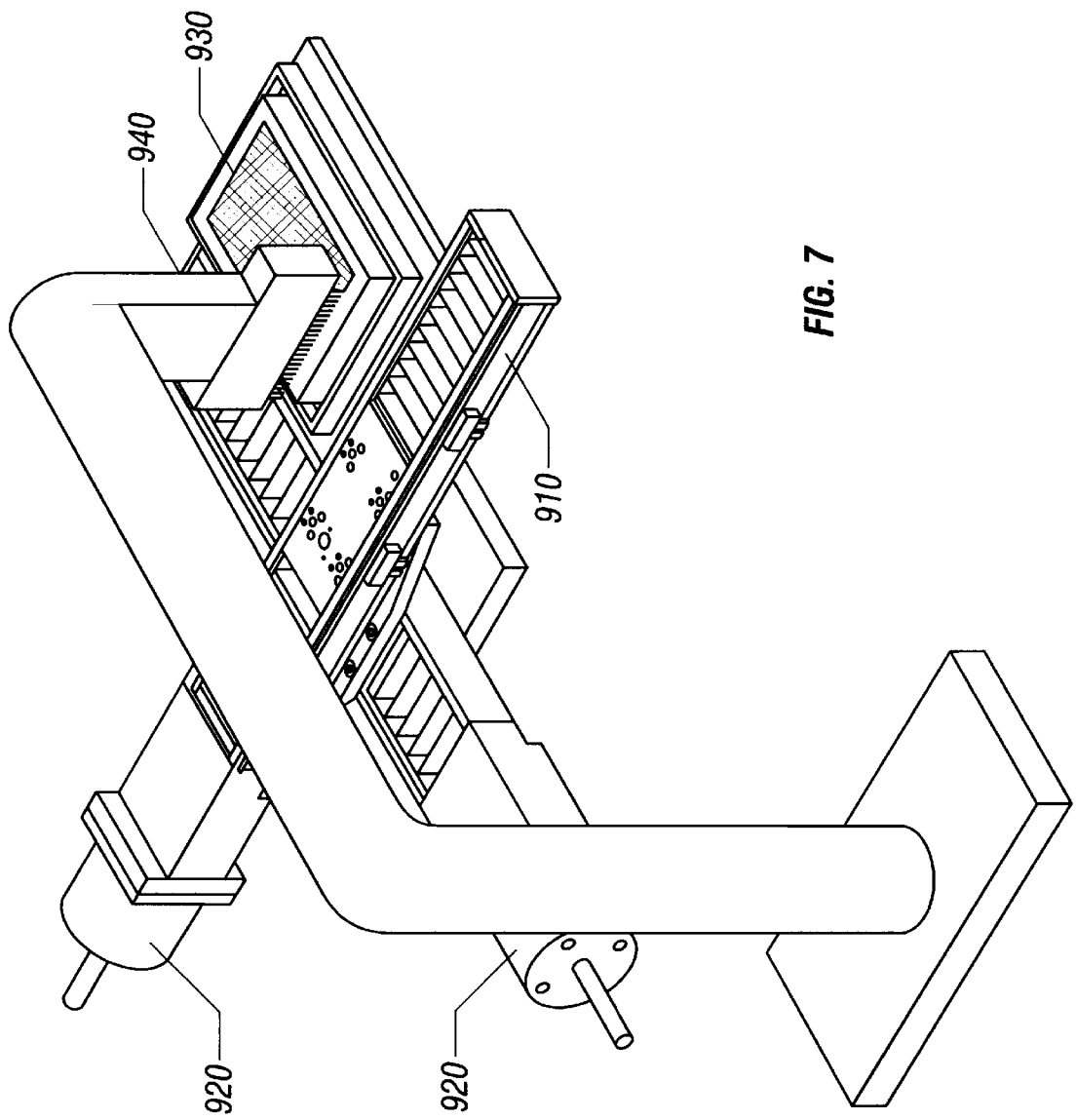
FIG. 7 shows one embodiment of a reagent dispensor.

FIG. 7 shows one embodiment of a reagent dispenser comprises an X,Y positioner 910 with two stepper motors 920 to control the positioning of a plate 930. The X,Y positioner places the plate in a predetermined X,Y coordinate that corresponds to the array of liquid dispensers 940. To position the addressable wells of a high density formal plate under the linear array, the X,Y positioner must preferably be able to locate predetermined X,Y coordinate within about 50 to 200 microns. It is therefore desirable to integrate and control X,Y positioners of the reagent dispenser, as well as of other components, with the data processing and integration module to finely control the stepper motors. Alternatively, the reagent dispenser can finely control the stepper motors with its own computer or programmable logic controllers.

For some embodiments of the invention, particularly for plates with 96, 192, 384 and 864 wells per plate, dispensers are available for integration into the system. Such dispensers are described in U.S. Pat. No. 5,525,302 (Astle), U.S. Pat. No. 5,108,703 (Pfost), U.S. Pat. No. 5,226,462(Carl), and PCT patent application WO 95/31284 (Gordon).

Detector

In one embodiment the invention provides for a reaction module that is a fluorescence detector to monitor fluorescence. The fluorescence detector is integrated to other workstations with the data processing and integration module and operably linked with the sample transporter. Preferably, the fluorescence detector is of the type described herein and can be used for epi-fluorescence. Other fluorescence detectors that are compatible with the data processing and integration module and the sample transporter, if operable linkage to the sample transporter is desired, can be used as known in the art or developed in the future. For some embodiments of the invention, particularly for plates with 96, 192, 384 and 864 wells per plate, detectors are available for integration into the system. Such detectors are described in U.S. Pat. No. 5,589,351 (Harootunian), U.S. Pat. No. 5,355,215 (Schroeder), and PCT patent application WO 93/13423 (Akong). Alternatively, an entire plate may be "read" using an imager, such as a Molecular Dynamics Fluor-Imager 595.

Figure 8:
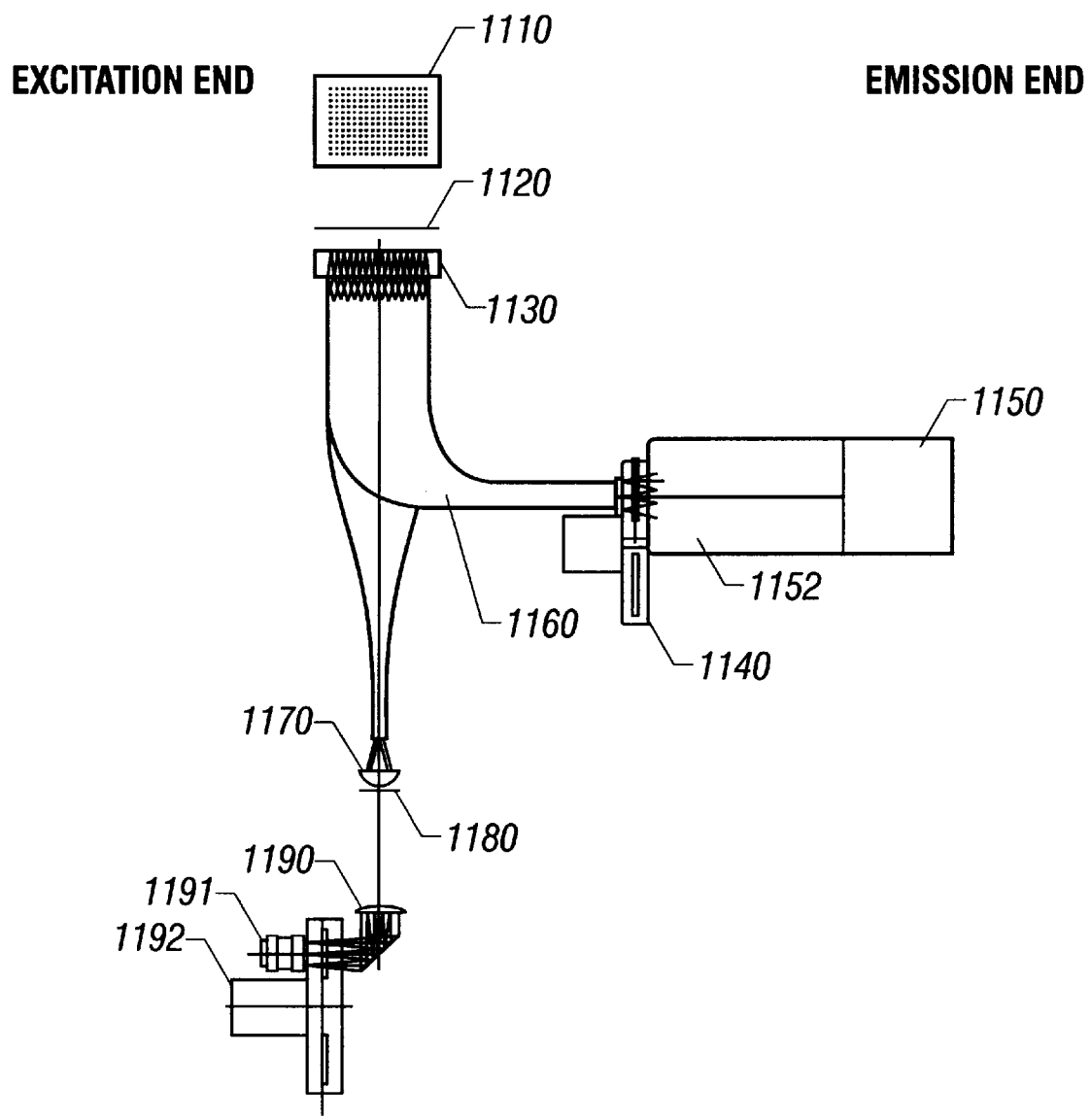
FIG. 8 shows one embodiment of a detector.

FIG. 8 shows one embodiment of a fluorescence detector comprising an X,Y positioner 1110 with two stepper motors (not shown) to control the positioning of a plate 1110 (plain view) and 1120 (side view). The X,Y positioner places the plate in a predetermined X,Y coordinate that corresponds to the array of optical collection assembly 1130. To position the addressable wells of a high density formal plate under the linear array, the X,Y positioner must preferably be able to locate predetermined X,Y coordinate within about 50 to 200 microns. It is therefore desirable to integrate and control X,Y positioners of the fluorescence detector with the data processing and integration module to finely control the stepper motors. The filter wheel 1140 is part of the emission optical relay system that filters light emitted from each fiber optic bundle 1160 that corresponds to a particular optical collection assembly. An optical relay means 1152 optically connects the bundle to a photon detection means 1150. A field lens 1170 is used to focus excitation light from a light source 1192. A second filter wheel 1192 is used to filter excitation light. Light is then relayed to a field lens 1190 and is then passed through a controllable aperture 1180. Light is then finally focused onto the fiber optic bundle for emission into addressable wells.

The detector is preferably capable of fluorescence emission measurements in the 400 to 800 nm range. Typically, the detector comprises a means for excitation of fluorescence in the 350 to 800 nm range. The detector is often capable of many different operating modes that facilitate drug discovery assay requirements. These operating modes can include: single excitation wavelength with single emission wavelength detection, single excitation wavelength, dual emission wavelength detection, sequential dual excitation wavelength with dual emission wavelength detection and ratio measurement determination, sequential dual excitation wavelength with four emission wavelength detection and ratio measurement determination, homogeneous time resolved fluorescence with single excitation wavelength and single emission wavelength detection, homogeneous time resolved fluorescence with single excitation wavelength and dual emission wavelength detection and ratio determination measurement, homogeneous time resolved fluorescence with sequential dual excitation wavelength and dual emission wavelength detection and ratio determination measurement, dual sequential excitation wavelengths and single emission wavelength detection with ratio determination measurement, luminescence measurement at a single wavelength with luminescence measurement at dual wavelengths, luminescence measurement at dual wavelengths with a ratio determination, and time resolved fluorescence emission (intrinsic dye properties with or without a binding event).

In the preferred embodiment, the detector comprises a light source assembly (e.g., Xenon) that can be switched between continuous and pulsed (1 kHz) output depending upon power supply. It includes an excitation light aperture to control the excitation field of view for fluorescence. Fused silica fiber optic light guides can be used for maximum transmission of excitation and emission light. Guides are selected for ultra low auto-fluorescence and raman background. The light collection assembly is optimized to gather light from an addressable well (e.g., coaxial fiber optic arrangement with a ball lens light collection assembly). The surfaces of the lens are preferably coated with anti-reflection coatings that reduce background signal levels during detection. The fiber optic guide/collection assembly is designed with a predetermined physical spacing of guides/collection assemblies that directs the excitation light to reduce optical cross talk to negligible or acceptable levels at the collection site. The physical spacing can also spatially correspond to the well density of the addressable wells of the interrogated plate. Plates with well densities greater than the density of light collection assemblies can be interrogated with light collection assemblies spatially arranged to accommodate X,Y positioning for higher well densities. This can be accomplished with the use of a X,Y positioner as described herein for liquid handling apparatuses. Preferably, dual emission collection fiber optical guides are used to enable simultaneous collection of two emission wavelengths during detection without any movements of optical relay system. The detector can include an excitation filter "wheel" for rapidly changing an excitation interference filter or an emission filter "wheel" for rapidly changing an emission interference filter set. The detector can also include a Z positioner to change the distance between the collection assemblies and the well or plate (usually the plate bottom) to optimize signal collection. Typically, the fiber optic guides and light collection assemblies are arranged in two dimensional arrays (e.g. corresponding to a 96 well plate) to allow for simultaneous detection of all addressable wells or a matrix of a portion addressable wells. The detector can include a photon sensitive surface for measuring photon emission, such as a CCD, photodiode, or a PMT. The detector can intensify the signal, and gate if desired, using a photon intensifier. Preferably, the detector can utilize a high quantum efficiency CCD without an intensifier for long detection integration. Alternatively, the detector can utilize PMT's or multi-site PMT's for photon detection and quantitation.

The detector functions primarily in the epi-fluorescence mode where the preferred illumination is from the bottom of the plate and the preferred collection is also from the bottom of the plate. The detector can function in all of the above mentioned modes with bottom viewing of the plate. The detector usually is capable of three to four orders of magnitude of dynamic range in signal response from a single reading. The detector, in a preferred embodiment, utilizes a CCD chip for imaging and detecting photons emitted from the assay wells.

The detector is typically capable of measuring the emission output at simultaneous dual wavelengths for 96-assay wells at a time. The detector can make ratio determinations on the 96-assay wells based on the dual wavelength detection or excitation ratio measurements of 96-assay wells by a change in the filter element in front of the Xenon Arc lamp source. The excitation ratio measurements can be measured serially at each set of 96-assay wells to be detected. The detector is capable of reading 96-assay wells in less than a second. This is a dramatic improvement over "state-of-the-art" fluorescence readers. This is 30 to 200 times faster than current readers. The detector optical guide/collection assembly has measured fluorescence from a sample with as little as $5 \times 10^{-12}$ mole fluorescein in 1 microliter of solution and at two wavelengths simultaneously.

The ratio mode of the detector enables changes in signal levels with respect to relative signal levels to be observed without complex calibration. The ratio mode of the detector is tolerant of differences in the quantities of isolated targets, cells or dye loading into cells. Hence, differences between wells can exist for the cells and dye levels, but within a single well, these differences can be normalized to relative change in the intensities. Without ratiometric detection, absolute signal levels can obscure the slight changes within each well.

The throughput of a detector in a screening system is often the slow step in processing a large number of assay plates. The detector (or detectors) usually must keep pace with the number of assay plates to be analyzed. Ultimately, the rate limiting step in a screening experiment determines the number of assay plates which can be analyzed in a given time period. For example, a preferred detector utilizes 96-array trifurcated fiber assemblies that enable one excitation wavelength (one bundle set) and two emission wavelengths (two bundle sets) per reading. In the case where excitation ratio measurements are required, the detector can sequentially deliver the two excitation wavelengths and then provide up to four emission wavelength results. Additional emission wavelength readings can be obtained by sequential switching of the emission filters. In the case of a 3,456 plate, 36 separate readings will be required to completely detect fluorescence from all 3,456 addressable wells. At one second per reading, the detection time is approximately 36 seconds not counting plate in/out and discreet movements. If the transfer time of the plate in and out of the detector is 24 seconds total plate reading time is one minute per plate. This results in the processing of sixty 3,456 well plates per hour, or 207,360 addressable wells per hour (4,976,640 addressable wells per 24 hours).

The selection of different operating modes of the detector is often based on the type of assay to be performed. Thus, the detector is usually designed with numerous modes of operation to provide flexibility in detection. Each mode is selected based on its compatibility with a particular set of fluorescent probes and reagents. The detection is then tailored to meet the assay's and the probe's requirements.

TABLE 2

| | Per 96 Element Matrix | | | | |
|---|---|---|---|---|---|
| Detection/Integration Time (msec) | Positioner Move Time (msec) | Pause Time (msec) | Total (msec) | Per Plate Total (sec) | Per Plate Total (min) |
| 500 | 500 | 100 | 1100 | 40 | 0.66 |
| 1000 | 500 | 100 | 1600 | 58 | 0.96 |
| 3000 | 500 | 100 | 3600 | 130 | 2.16 |
| 5000 | 500 | 100 | 5600 | 202 | 3.36 |
| 10000 | 500 | 100 | 10600 | 382 | 6.36 |

Table 2 shows calculated detection times for a 96-matrix optical array detector The detector can have variable data acquisition time depending on assay requirements. If a read/integration time is 1 sec per 96 elements, a plate read time is under 1 minute. If a plate in/plate out operation 1 minute, then thirty, 3,456 plates per hour can be read at two wavelengths. Thirty such plates are equivalent to over 90,000 samples per hour (assuming 10% of the plates are used for controls, etc.). For an eight hour work period, about 720,000 samples can be processed. The inventors have measured signals from microliter wells (assay volume about 2 microliters) in ratiometric fluorescent measurement mode in about 100 milliseconds.

Fluorescence Measurements

It is recognized that different types of fluorescent monitoring systems can be used to practice the invention with fluorescent probes, such as fluorescent dyes or substrates. Preferably, systems dedicated to high throughput screening, e.g., 96-well or greater microtiter plates, are used. Methods of performing assays on fluorescent materials are well known in the art and are described in, e.g., Lakowicz, J. R., *Principles of Fluorescence Spectroscopy*, New York: Plenum Press (1983); Herman, B., Resonance Energy Transfer Microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N.J., *Modern Molecular Photochemistry*, Menlo Park: Benjamin/Cummings Publishing Col, Inc. (1978), pp. 296–361 and the Molecular Probes Catalog (1997), OR, USA.

Fluorescence in a sample can be measured using a detector described herein or known in the art for multi-well plates. In general, excitation radiation, from an excitation source having a first wavelength, passes through excitation optics. The excitation optics cause the excitation radiation to excite the sample. In response, fluorescent probes in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage (e.g., a dedicated X,Y positioner) moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Preferably, FRET (fluorescence resonance energy transfer) is used as a way of monitoring probes in a sample (cellular or biochemical). The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in signal are determined as the ratio of fluorescence at two different emission wavelengths, a process referred to as "ratioing." Differences in the absolute amount of probe (or substrate), cells, excitation intensity, and turbidity or other background absorbances between addressable wells can affect the fluorescence signal. Therefore, the ratio of the two emission intensities is a more robust and preferred measure of activity than emission intensity alone.

A ratiometric fluorescent probe system can be used with the invention. For instance the reporter system described in PCT publication WO96/30540 (Tsien) has significant advantages over existing reporters for gene integration analysis, as it allows sensitive detection and isolation of both expressing and non-expressing single living cells. This assay system uses a non-toxic, non-polar fluorescent substrate which is easily loaded and then trapped intracellularly. Cleavage of the fluorescent substrate by β-lactamase yields a fluorescent emission shift as substrate is converted to product. Because the β-lactamase reporter readout is ratiometric, it is unique among reporter gene assays in that it controls variables such as the amount of substrate loaded into individual cells. The stable, easily detected, intracellular readout simplifies assay procedures by eliminating the need for washing steps, which facilitates screening with cells using the invention.

Data Processing and Integration Module

Because the present invention provides for unprecedented throughput rates for processing of liquid samples, it will be important in many embodiments of the invention, especially system embodiments, to integrate modules, direct workflow and manage information generated by such a system. This can be accomplished by providing a computer module with a processor that can integrate and programmably control workstations and workflow, and collect and store information from each workstation. A central feature applicable to most such systems is a computer module to route the work unit, track work unit inventory and to provide instructions to process liquid samples through the appropriate workstations. Typically, the computer will include a relational database that contains information for processing a liquid sample and optionally, using the information resulting from a process to create a database of output information that can then be used to support additional analysis of the data or to automatically modify the process based on the results obtained in a single or multiple cycles of a process.

In one embodiment, a data processing and integration module can integrate and programmably control a storage and retrieval module, a sample distribution module, and a reaction module to facilitate rapid processing of said addressable sample wells. Preferably, the data processing and integration module can programmably route work flow to modules by the programmably controlled adaptive routing, and optionally programmably controlled parallel processing of addressable wells.

To manage information in the system, the data processing and integration module comprises elements to store, manage and retrieve data, including a data storage device and a processor. The data storage device can hold a relational database, an array of physical disk drives (e.g., random access disk drives), and a connection to other system components via a network. A data storage device can, for instance, store a relational database for environmental, diagnostic, chemical synthesis and drug discovery applications. For instance, one particularly useful relational database can be provided by Oracle, and the network can be a TCP/IP (transfer communication protocol) ethernet LAN (local area network).

The system can be controlled using supervisory control programs, which are not necessarily located on the same computer as the data storage device. For example, in one embodiment of a system, a separate supervisory control computer is provided for each of the Storage and Retrieval, Reagent Transport, and Reagent Distribution functions. A supervisory control computer is a computer programmed to control a particular subsystem using data from the data storage device and operating on a workstation or component, such as a storage and retrieval, reaction module or sample transporter.

Within the data storage device, exists a structure for information in the form of tables and relations. This structure is designed to meet the specific needs of the system, wherein it must accommodate the throughput demands of an automated system and facilitate the presentation of information for analysis and visualization of results. The data storage device can typically process in excess of 100,000 transactions (read or write particular data) per day, while accurately keeping track of every chemical, biological reagent, operation, unit of work and workstation and other related activities. Integrity of the data storage device is typically maintained for simultaneous multiple users and processes.

Information in the relational database of the data storage device is used to define operations to be performed, and a complete audit trail can be maintained of every operation on every unit of work throughout the system.

Storage devices suitable for use with the present invention are well known and are commercially available from a number of manufacturers, such as the 2 gigabyte Differential System Disk, part number FTO-SD8-2NC, and the 10 gigabyte DLT tape drive, part number P-W-DLT, both made by Silicon Graphics, Inc., of Mountain View, Calif., or equivalents (e.g., optical discs). A preferred embodiment uses Hewlett Packard 4GB Hot Swap Drives in a Netserver LX Pro configured as RAID-5

Figure 9A:
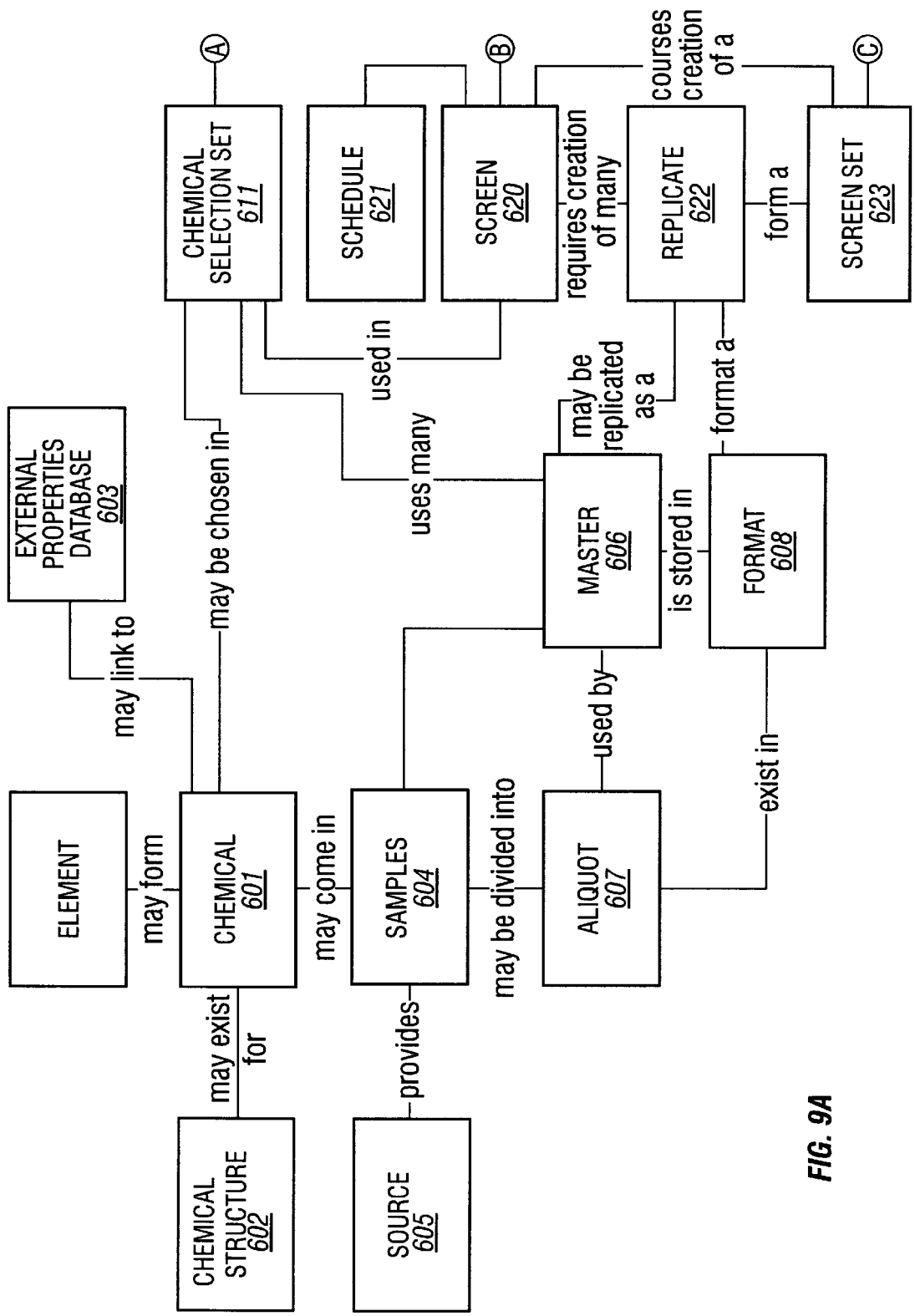
FIG. 9 shows one embodiment of a data structure.
Figure 9B:
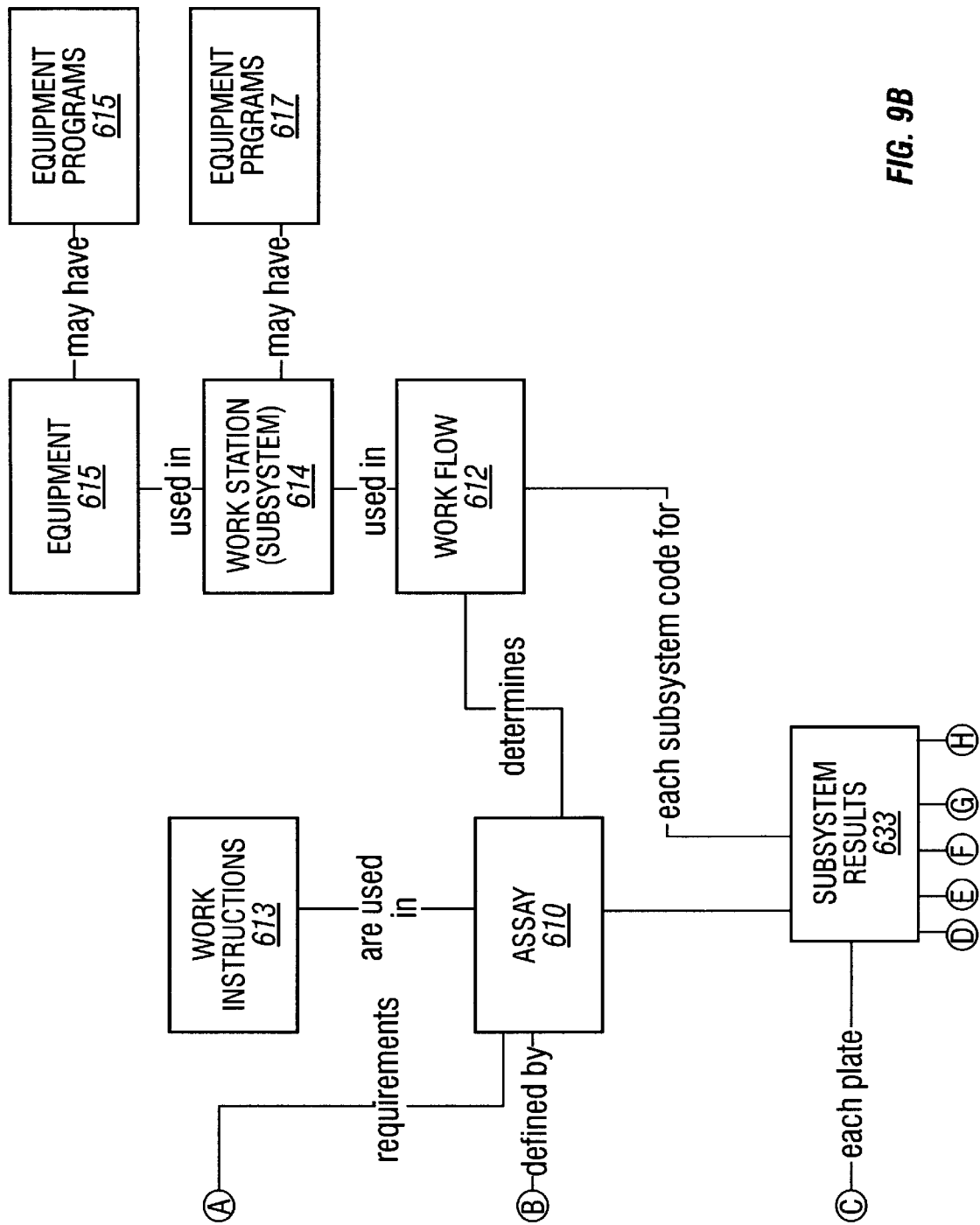
Figure 9C:
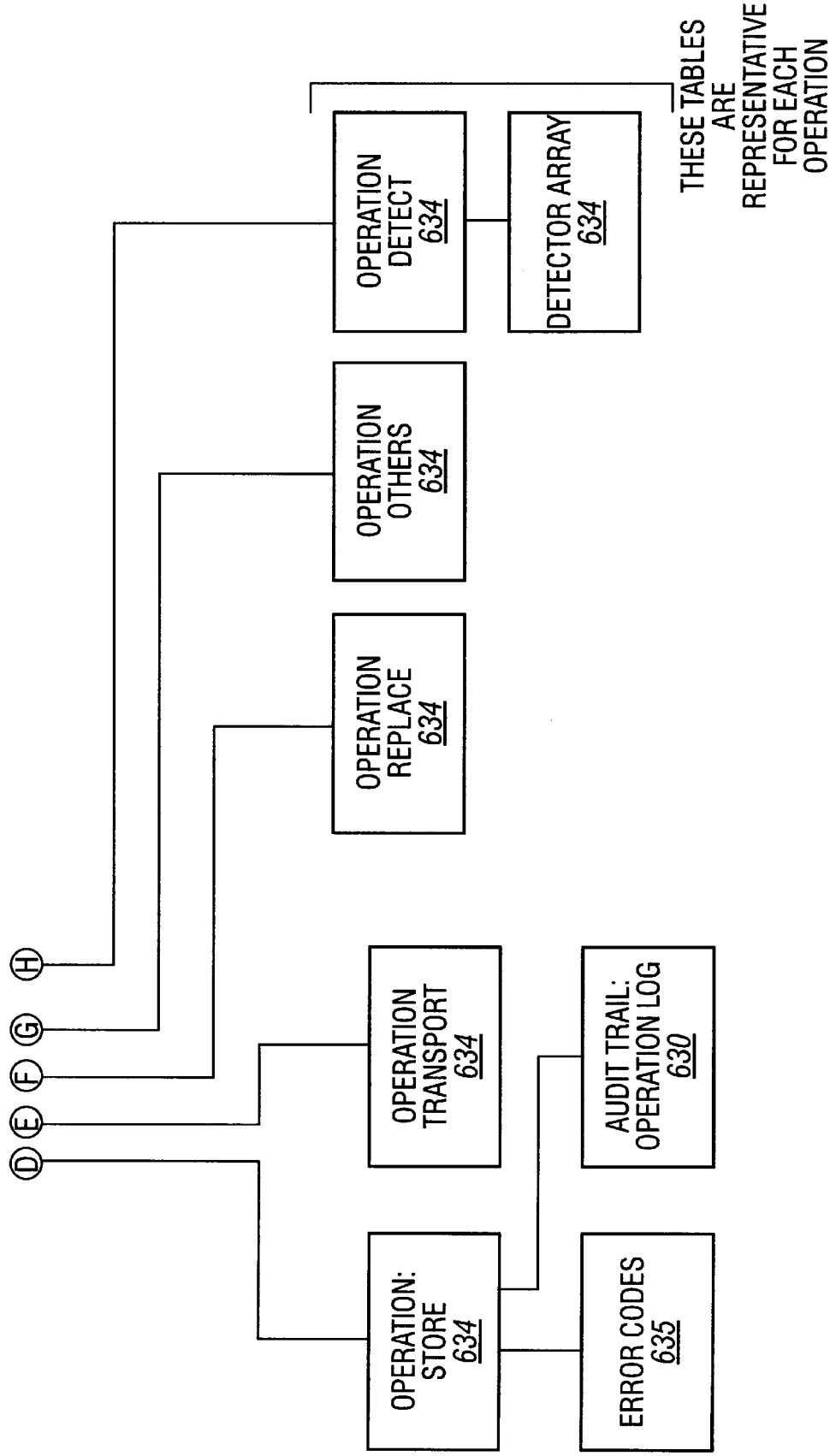

FIG. 9 shows a data structure diagram illustrating the tables and relations in the supervisory control system.. The data structure can be divided into function sectors, such as chemical and sample management, work flow and assay design, screening information, and subsystem control.

A chemical and sample management may embody links to other computerized systems for data management, such as an external properties database 603 that could contain chemical and physical properties. The system may optionally contain information related to the general lookup of properties or structures of chemicals. Such information is contained in the chemical structure table 602. Chemicals themselves are represented in a chemical table 601, which contains data regarding chemical formula, scientific names, and text descriptors. All information about a particular instance of a chemical is represented in the samples table 604. A sample may be obtained from a supplier, created by a chemist, or from any other means defined in the source table 605. The FIG. 9 also describes other relations that are most important between each table.

A chemical and sample management may also comprise a plurality of samples that can be grouped together in the master table 606. The inventors have made such a collection on the order of about 10,000 samples or chemicals. Larger collections of about 50,000, about 100,000 and over 500,000 (e.g., about 1,000,000 to about 10,000,000) are also contemplated. The master table is used to define groupings of chemicals, such as would occur when the chemicals were present in a common format.

Each chemical in the master table is also represented in an aliquots table 607. The creation of aliquots from any chemical managed by the system may be in any format and is not limited to multi-well plates. A chemical may be individually tracked, or become part of a master configuration where it is present with a plurality of other chemicals, in which case the group, rather than a single chemical can be tracked by the system. Each tracked entity (e.g., work unit) is recorded as an entry in format table 608. The current location of each tracked entity is stored along with its identification in the table that represents that entity. Typical formats can include tubes and bottles of various capacities, arrays of wells as in the various multi-well plates, or any other format desired. Any chemical or group of chemicals stored in a format can be identified, e.g., by a unique bar code label.

Figure 10A:
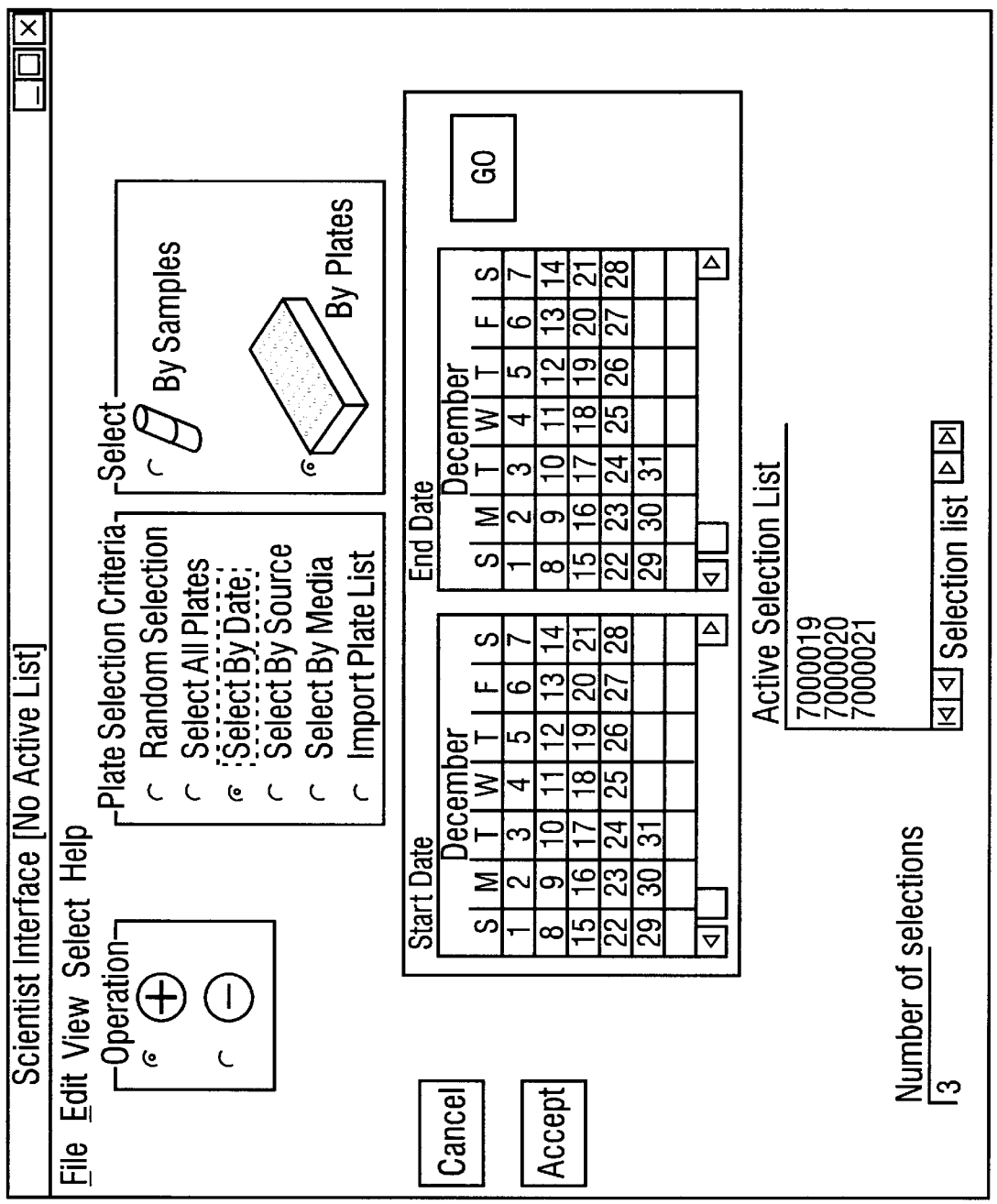
FIG. 10A shows one embodiment of a user interface.
Figure 10B:
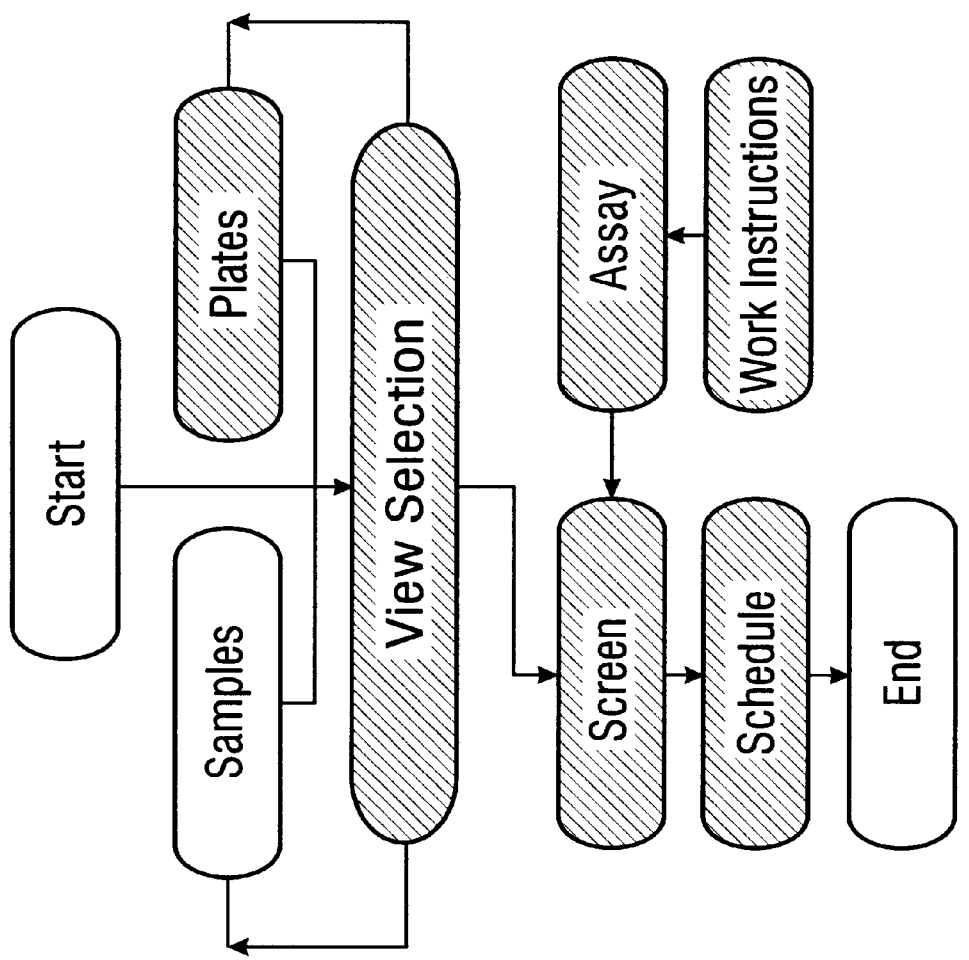
FIG. 10B shows one embodiment of a user interface.
Figure 10C:
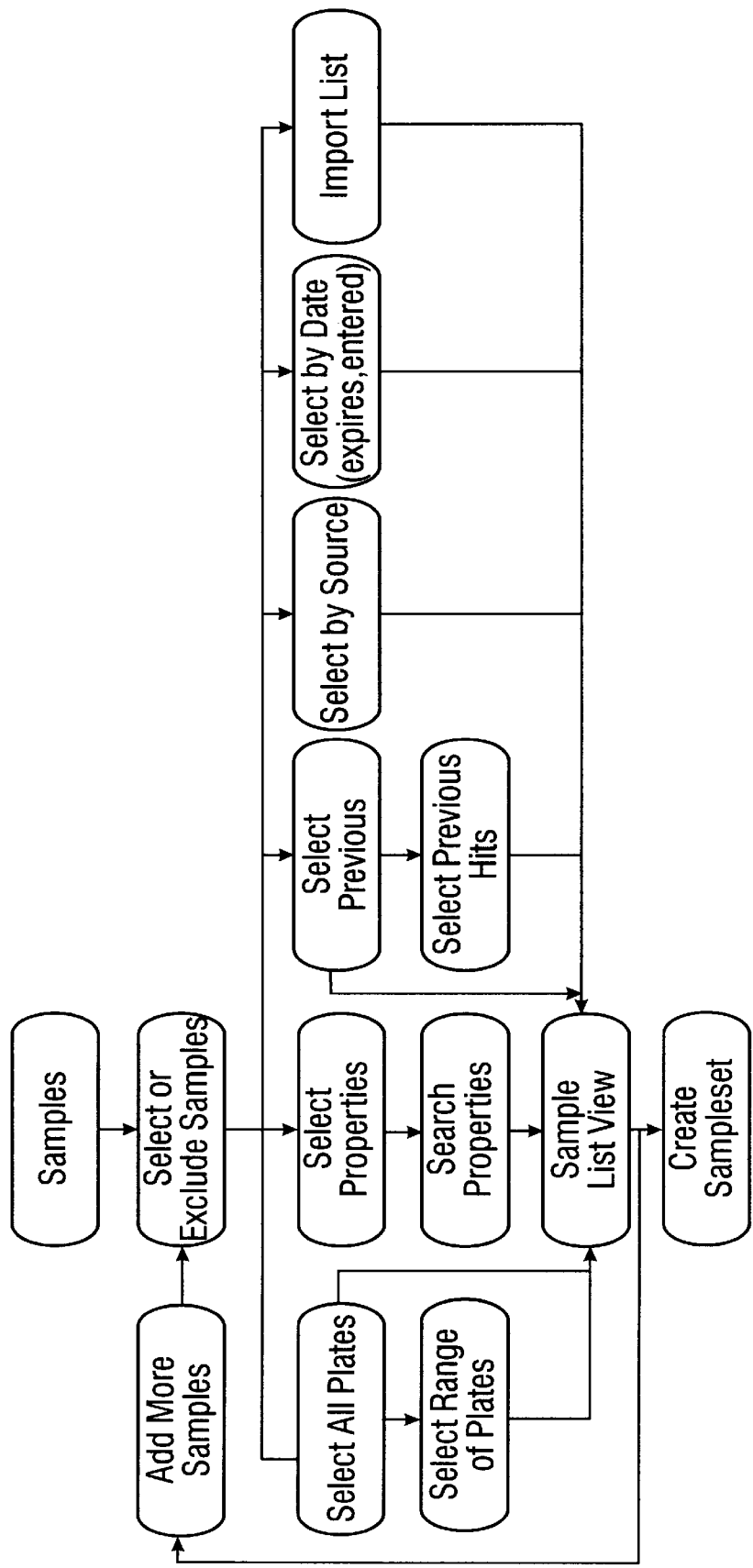
Figure 10D:
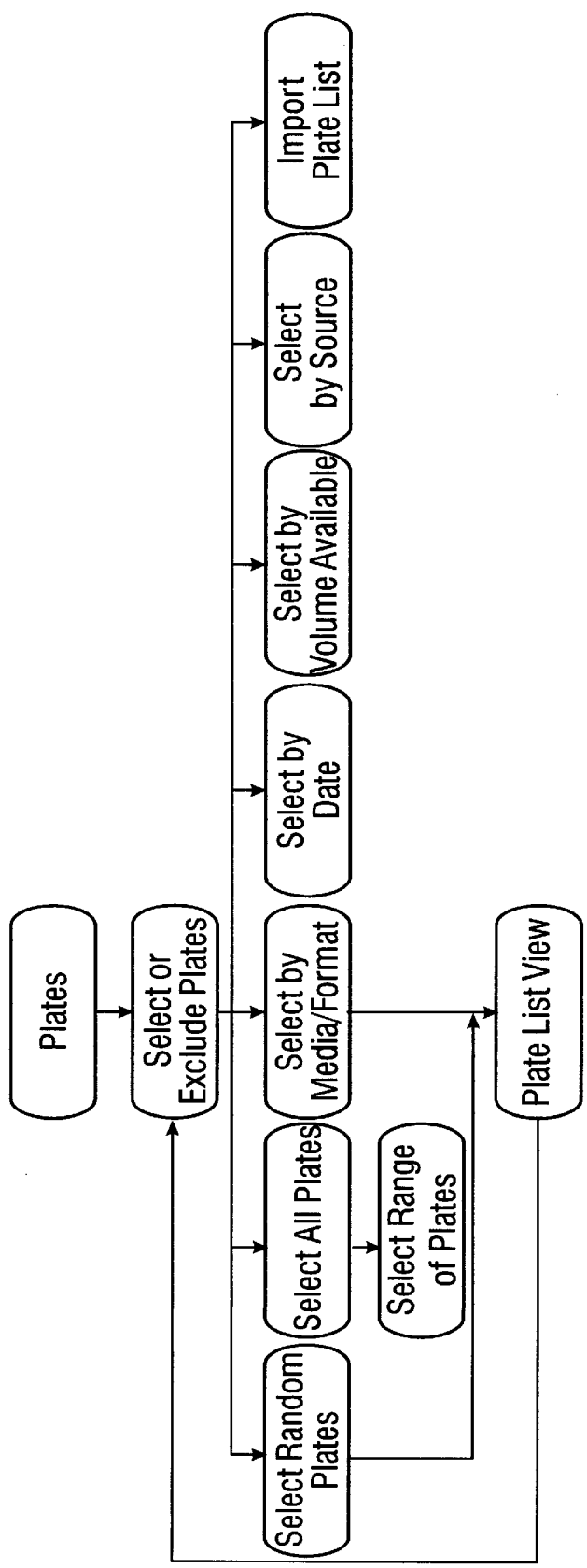

The work flow and assay design area of the data store typically defines the work process to be performed, and parameters necessary to control the automation of the system. Automation refers to both individual workstations, and can include the transport and storage and retrieval functions. An external scientist interface program is used to fill in values in the work flow and assay design tables, which can then be scheduled and executed by the operator interface program. A flowchart of some elements of the scientist interface is provided in FIG. 10A and one embodiment of a scientist interface is shown in FIG. 10B.

The work flow and assay design algorithms can be implemented in supervisory control computers or with a single supervisory control computer. These programs can constitute a batch process control system (meaning that desired sequences of parameters or instructions are created and executed in units of operation) with continuous and discrete elements (meaning that the system must manage a continuous control based on process variables, as well as real-time events, such as interrupts). The data store structures exist to provide parameters and define the workflow, and to receive results from these supervisory control computers.

An assay can be defined in the assay table 610, composed of three elements: selections from the chemical selection set table 611, a sequence of workstations to be utilized defined in the work flow table 612, and a human readable text, defined in the work instructions table 613. The work instructions include the steps necessary for an operator in preparing each workstation for the assay, such as reagent preparation, machine cleaning and setup, and any other manual operations.

The definition of work flow can be performed by the scientist interface software. A graphical user interface is used to build an assay or other liquid sample process on a computer screen from the various workstations that exist in the system. These workstations are represented in the workstation table 614, which is itself composed of references to the equipment table 615 and the corresponding entries in the equipment parameters table 617. Thereby, the scientist interface can expand the representation of a workstation to display any configuration requirements or programs for each piece of equipment at the workstation. Different workstations will require different parameters, and screens are specially developed to enter that information in the equipment parameters table.

Screening information portions of the data store are used to bring chemicals and work flows together and to perform a screen (or alternative an analysis or synthesis). Each screen is defined in a screen table 620. Once screens are defined they can be scheduled for running by the operator interface that modifies the schedule table 621. Many screens can be defined using the same entry in the assay table 610. Based on the screen and the chemicals defined to participate in the screen, i.e., the entries in the chemical selection set table 611 that are defined in work flow and assay design, the operator interface program will create a list of required replicates to be created from masters, and make entries in the replicate table 622. The replicates are always related to a master in a particular way. Many masters can be replicated on a replicate, but each replicate must have at least one master (e.g., the representation of a master plate and a daughter plate). This permits combining multiple storage plates into a single plate of higher density.

Automated portions of the screening system, such as format copying devices, create replicates. The replicate table 622 is used to record their parameters, i.e., the bar code label, plate type, and master plates used. Usually it is advantageous for the replicate record itself not to contain information about the chemicals. For all further operations on the replicate, operations will be on the entire format. For analysis purposes, the chemical information is readily available in the master records, which are related to each replicate. The list of replicates for a screen is placed in a table of screen sets 623. The screen set is a list of the plates necessary to represent the chemical selection set, already described in chemical selection set table 611.

The data storage device can contain items related to the automated operation a process. A computer program is used to control each workstation in the system. An advantageous design element is to include all information necessary to operate the workstation in the respective operation table(s) 634. The operation tables given here are representative and will vary for different operations that are available in the system.

Additional tables can exist depending on the workstation to record error codes in the error code tables 634, history of operations in the audit trail tables 636, or raw data such as shown in the detector array table 637. Subsystem results are summarized in the subsystem result table 633, which is related to the contents of the workflow table 612 defined by the scientist interface program. For analysis, the content of the subsystem results table 633 is used to visualize completed screens.

Previous data stores for similar applications have concentrated on the physical representations of units of work. These systems were suited to manual handling of units of work and often used elaborate data entry mechanisms. The present invention focuses on the automated handling of units of work, and typically assumes that the well quantity and density processed greatly exceed what would be reasonable for a human operator to monitor. As a result, this data store is structured for high performance. For example, the replication of a single high density unit of work would require thousands of database transactions in other designs, but can be accomplished in a single transaction against a replicate table in the present invention.

Data flow in and out of the data store is primarily through integrated instruments, controllers, and devices. Typically, transactions e.g., moving a plate, dispensing, aspirating, and others, are recorded in the database.

Detectors, such as those found in the reaction module are instruments which produce large quantities of data associated with each well. This data is processed and stored in the data processing and integration module. It is also desirable that the data processing and integration module provide a historical record of all operations and results obtained for a given unit of work, or an addressable well. In the preferred embodiment, an addressable well can be examined based on the processed detector results, and a hierarchical view of all previous results and operations is obtained.

Specific Systems, Material FHow and Work How Related to Screening Chemicals

Figure 2:
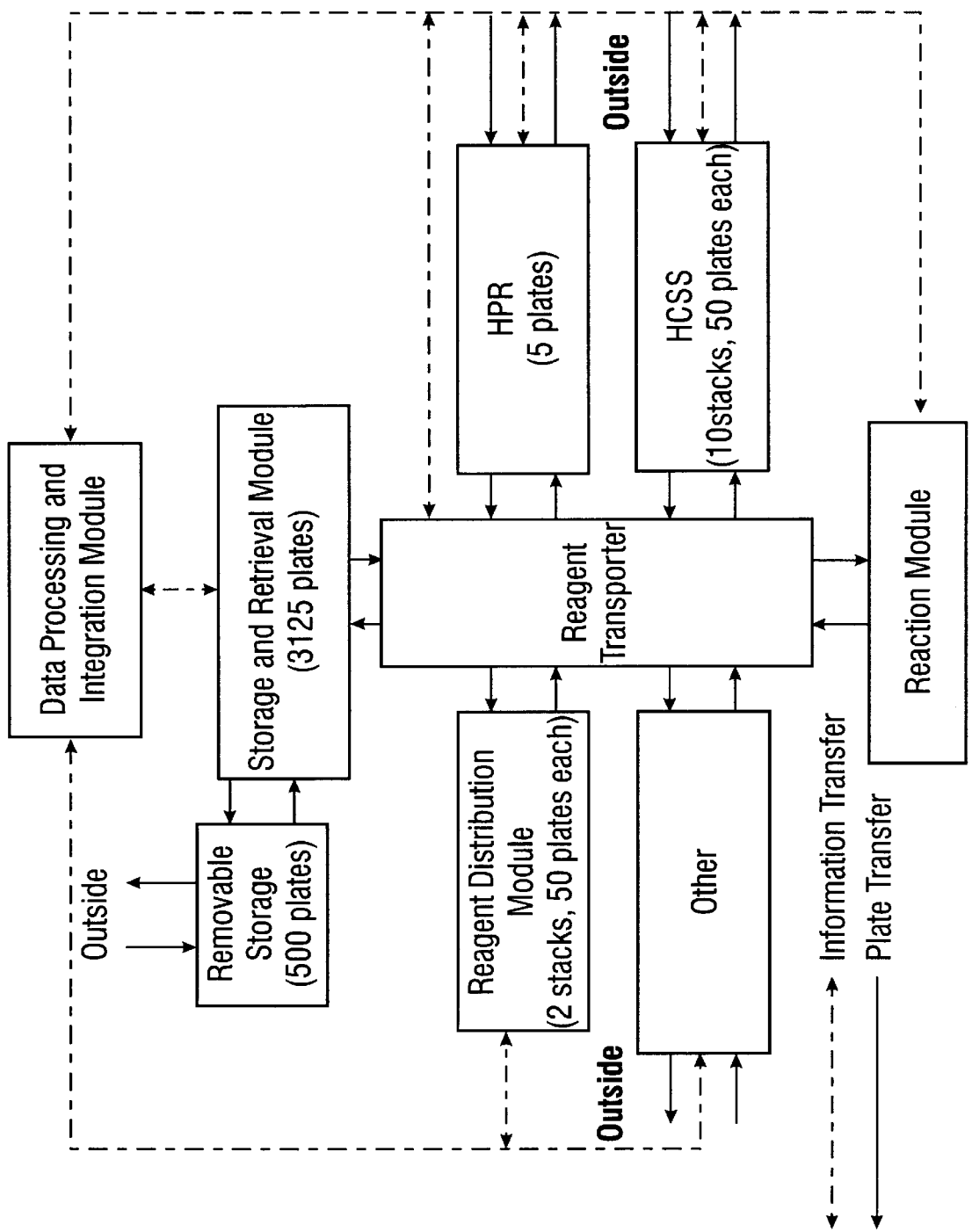
FIG. 2 shows one embodiment of a liquid sample processing system that could be used for identifying useful chemicals and exemplary routes of information and plate transfer.

One embodiment of the present invention is a liquid processing system for screening chemicals for useful activity, as shown in FIG. 2. This screening system comprises a storage and retrieval module for storing and retrieving vast numbers of different reagents in containers, a sample distribution module to handle (e.g., aspirate reagents from containers and dispense reagents into other containers) small volumes of liquids at a high rate of speed, a sample transporter to transport reagents from a selected component to another component at a compatible throughput rate, a hit profiling robot (HPR) to aspirate and dispense selected solutions from addressable wells containing chemicals suspected of having useful activity, a high capacity stacking system (HCSS) to act as a plate buffer to temporarily store plate for greater retrieval flexibility, a reaction module (e.g., a second reagent dispenser or a detector) for chemical reactions or physical measurements at high throughput rates, and a data processing and integration module. The data processing and integration module integrates each component using a computer program, and optionally with a database comprising predetermined and modifiable instructions for performing the screening process. The sample transporter operably integrates the systems by transporting plates from one component to another component. Preferably the sample transporter permits parallel processing, and optionally adaptive routing, examples of which are described herein. The data processing and integration module also preferably can integrate the sample transporter with the other components to facilitate parallel processing and adaptive routing of plates. Preferred components and methods are described herein. Suitable state-of-the-art components can be substituted, so long as such components can integrate with the data processing and integration module and can be operably linked to the other components of the screening system. Other components, such as shown in FIG. 2, may be included in the system as well.

Figure 11:
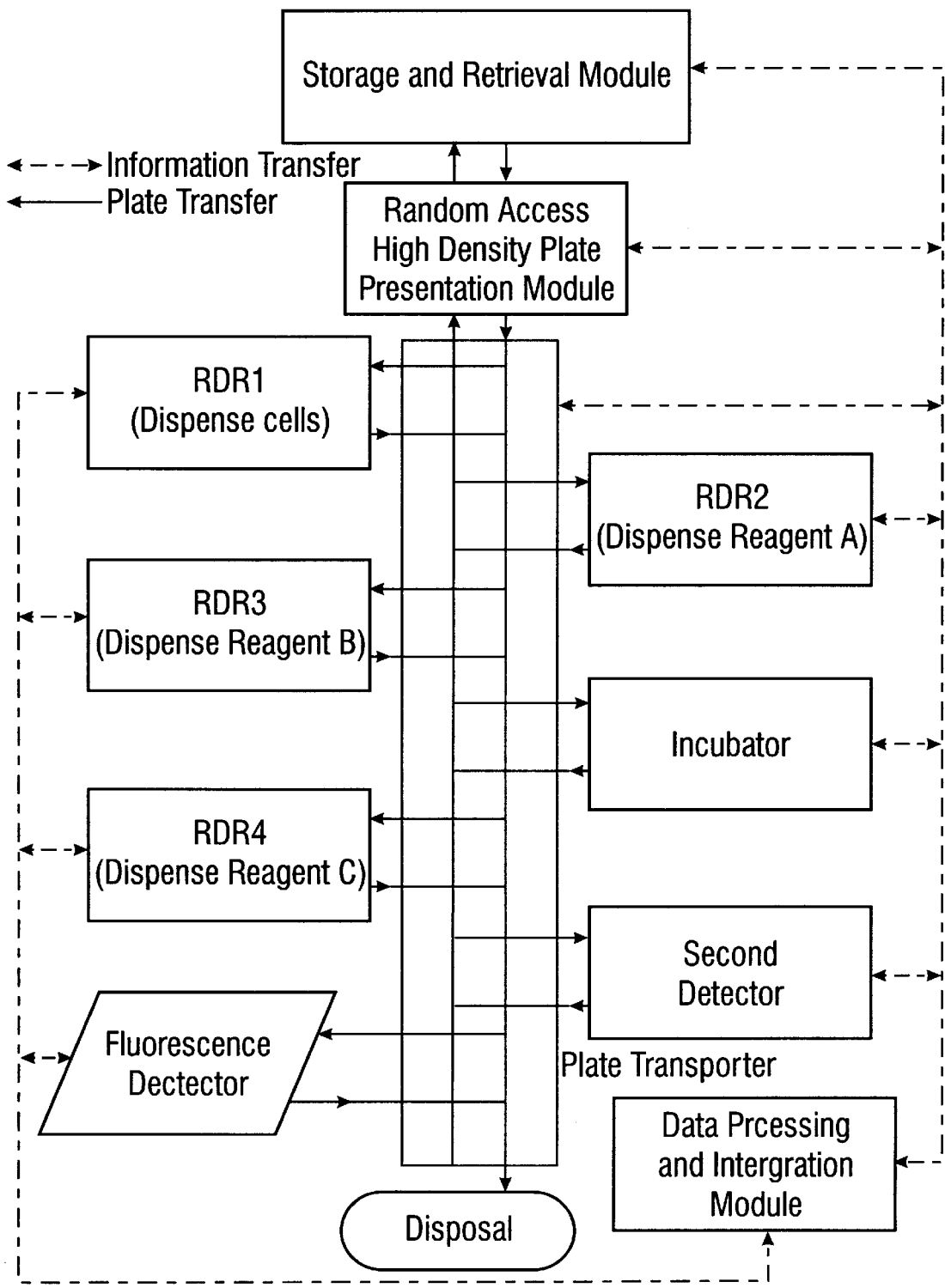
FIG. 11 shows one embodiment of a screening system.

A preferred embodiment of the screening system is shown in FIG. 11. Shown in FIG. 11 is a storage and retrieval module, a random access high density plate presentation module, multiple reagent dispensing robots for dispensing reagents to be used in a substantial proportion of the plates, multiple incubators to control the temperature of chemical events, a fluorescent detector to detect fluorescence of each sample in an addressable well, a plate transporter to transport plates and a data processing and integration module to integrate each component. This type system is desirable for complex screening procedures, where different reagents may require a different reagent dispensing robot based on the type of reagent, solvent, or screening process. One reagent dispensing robot can be dedicated for dispensing aqueous reagents, a second for non-aqueous solvents and a third for biological materials such as cells. Such a system can also include an incubator for controlling environmental conditions and humidifying assay plates to reduce evaporation. Incubators in the art can be adapted for such use, such as those discussed in U.S. Pat. No. 5,149,654 and U.S. Pat. No. 5,525,512. Preferably, each component is serviced by a multi-lane sample transporter to permit parallel processing.

Example of Work Unit (e.g., plate) Handling

The screening system typically operates on a work unit (unit) with standardized processing format. The work unit sometimes embodies a particular processing format, such as a plate. Such work units often vary in external dimensions, materials of construction, physical design and density (or number of wells). The screening system is preferably constructed using workstations to handle a standard processing format that allows for a flexible work unit. This approach reduces the need for complete uniformity of the work unit, as is required in many automated laboratory and chemical discovery systems. Consequently, the present invention's screening system can function with a mixture of many work units without adjustment or calibration. This permits the system to universally handle varying work units of a standardized processing format. Usually, such systems or components will handle at least 2 work unit densities with a standard format, preferably at least 3 work unit densities with a standard format, and more preferably at least 4 work unit densities with a standard format.

Typically, a storage and retrieval end actuator universal stacker/destacker transport system elements and the registration device are all devices that are designed to handle work units with standardized processing format. Preferably, to enhance workflow and throughput, all the devices that handle work units are designed to handle the same standardized processing format. Examples of these types of devices are described herein, especially in the Examples.

Material Flow Through a Screening System

The operation and liquid processing steps of a screening system can be described in terms of material flow. When describing material flow, a work unit can be considered to contain one or more chemicals (or chemicals in solution) in an array. The work unit of work might be a member of the chemical library, or might be a format designed for a specific purpose, such as a multi-well format drug screening plate. As described herein, workflow throughput can be optimized or increased using parallel processing, adaptive routing and computerized instructions from relational databases. An example of actual materials flow through a screening system is described below.

Figure 12A:
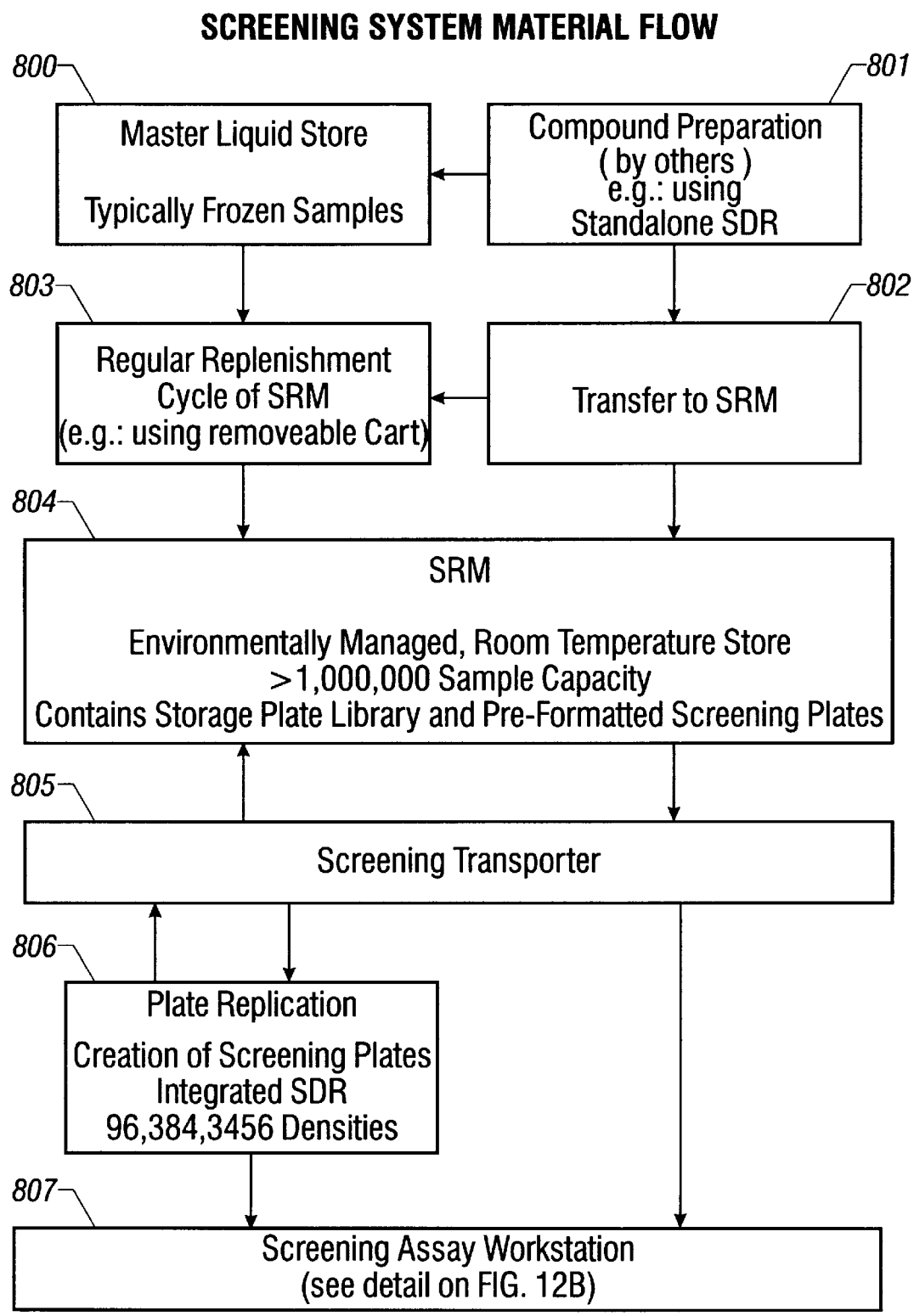
FIG. 12 shows one embodiment of screening system material flow.
Figure 12B:
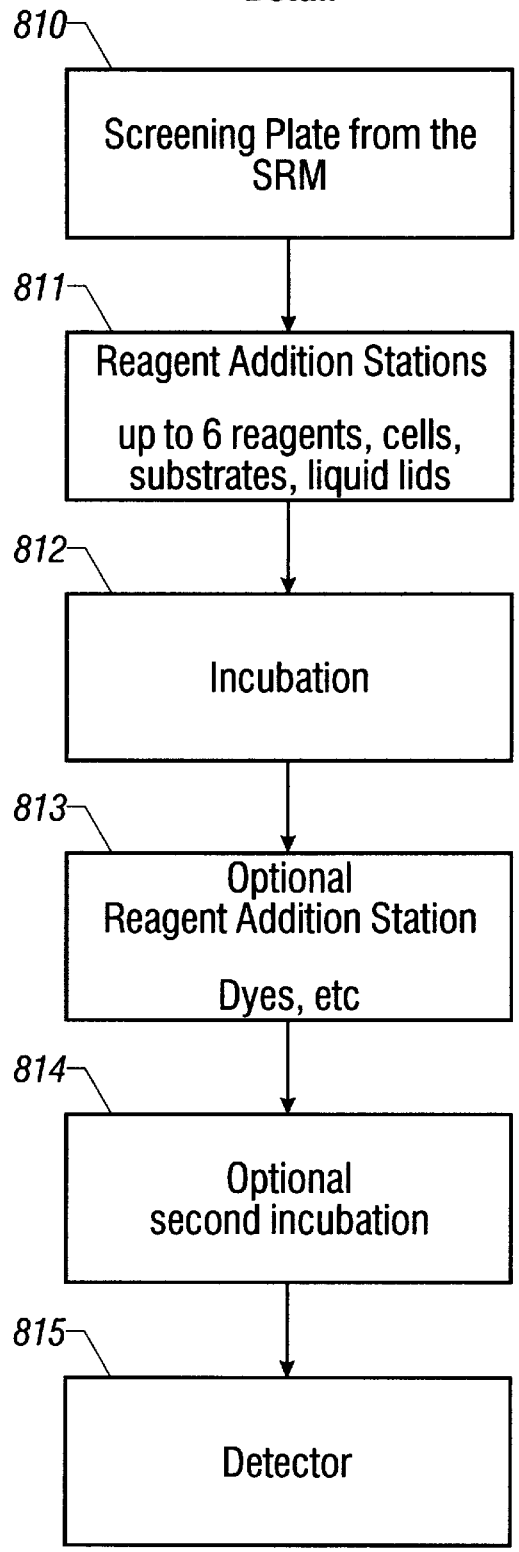

FIG. 12 shows material flow in a screening system and pre-screening processing. Master liquid storage 800, which is not usually part of the screening system, is the long term storage of chemicals prepared in compound preparation 801. Chemicals can also be formatted into work units in compound preparation step 801. Compound preparation involves the preparation of measured chemical samples, dilution in a liquid or dissolving with a solvent, and division of chemical solutions into measured aliquots. Usually, such chemical aliquots are reagents. In a screening context they are often referred to as test compounds. The chemical solutions, representing a known concentration are then grouped together in storage work units (e.g., addressable wells). In the preferred embodiment, these are multi-well storage plates of high volume capacity (e.g., 96-wells with 200 to 500 microliters per well). A standalone sample duplication robot can aid the compound preparation process. Work units are then transferred directly to the storage and retrieval module using the removable cart 802 or transferred during a replenishment cycle with a removable cart 803 to the storage retrieval module 804. Each removable cart can contain a plurality of storage work units (e.g., about 488). The master library work units are used to replenish the storage retrieval module as quantities are depleted, or a time period expires. A data processing and integration module can track the level of solution in a storage work unit as well as the expiration date for each work unit with a reagent or test compound.

The storage and retrieval module 804 can store a large number of chemicals in work units. Usually, the storage and retrieval module can store at least about 200,000 discrete chemicals on at least about 2,000 thousand work units and preferably at least about 1,000,000 discrete chemicals on at least about 4,000 work units and at least about 10,000,000 work units. Storage volumes for such stores are described herein (e.g., 20 to 100 microliters). Empty work units can also be contained in the store, and can be replenished with the removable cart 803. The storage and retrieval module provides environmental protection of the work units, which are individually accessible at room temperature. The storage and retrieval module contents can be randomly picked and delivered to the screening transporter 805 for transport. Transport functions include presentation of work units at workstations, routing from any workstation to any other, queuing of work units at workstations, and operably linking workstations of the screening system.

Formatting of work units (duplication or reformatting the work units the storage and retrieval module) involves a plate replication workstation 806. The equipment used in plate replication can be an sample duplication robot. Reformatting work units involves the transfer of chemicals from one work unit format to another, such as would be required when a higher density work unit was needed in a screening operation. For example, the formatting of storage plates (often at 96-wells per plate) into high density plates (e.g., as densities of at least about 864 to 3,456-wells per plate, or higher). The plate replication workstation can efficiently create a plurality of screening work units from a set of storage work units. If screening work units are not immediately needed they can be sent to the storage removal module..

As work units are directed for screening, either from the screening transporter 805 or from the plate replication workstation 806, they are transferred by the screening transport 805 to the screening assay system 807. Once a work unit has been used in the screening assay system, it will usually be consumed and not replaced in the storage and retrieval module. In some screening applications it may be desirable to perform a second test on the same work unit, in which case it may be desirable to route the work unit back through the system.

The screening assay system 807 typically consists of a series of steps defined in an assay sequence. The scientist interface (i.e. a computer screen or image) can be used to define each assay, which is then represented in the data storage device, which is part of the data processing and integration module. The material flow is modified by the software definition of the assay.

The general characteristics of the screening assay system are that all work units must follow a substantially similar material flow, in terms of time and devices used, to assure that results are comparable between work units. The assay set-up with the scientist interface includes the definition of the material flow, timing, workstation setup requirements, reagent preparation, maximum processing time, and the work units from the chemical library store in the storage and retrieval module that will be processed.

Work units 810, formatted specifically for screening by the plate replication workstation 806 are delivered by the screening transporter 805. Depending on the workflow defined in the assay, they are then consistently processed through a series of steps. In a reagent addition step 811, cells and a number of reagents can be dispensed into the work unit. A known agonist might be added to activate cells in a cell-based assay. Liquid lids might be dispensed. Such liquid lids are inert materials, which will reduce the evaporation of liquid from a well.

The work unit is then moved to an incubation step 812. Incubation time and environmental conditions, including temperature, humidity, and nitrogen can be carefully controlled. The conditions in this workstation, as in all others have been defined in the scientist interface software as the assay is developed. This results in an entry in the workstation operations table (in the data processing and integration module) for the particular work unit. As the work unit is processed, entries are made by the supervisory controller and can optionally provide an audit trail and error notification of process deviations for each work unit.

Following incubation 812, the work unit may be transferred to an additional reagent addition workstation 813. At this point, dyes, substrate, or additional indicators are added to facilitate the detector operation. If necessary an additional incubation 814 can be provided. In some cases this incubation is simply performed as part of the transport operation to the detector workstation through a measured time delay.

The work unit is then transferred to the detector 815. Detectors can vary depending on the assay and multiple detectors may exist on the same system. Typical detectors will measure emitted or fluorescent light, or measure a calculated ratio of light from each well of the work unit. After the work unit is processed at the detector, it could be transferred to a waste station, or returned to the storage and retrieval module.

Figure 13A:
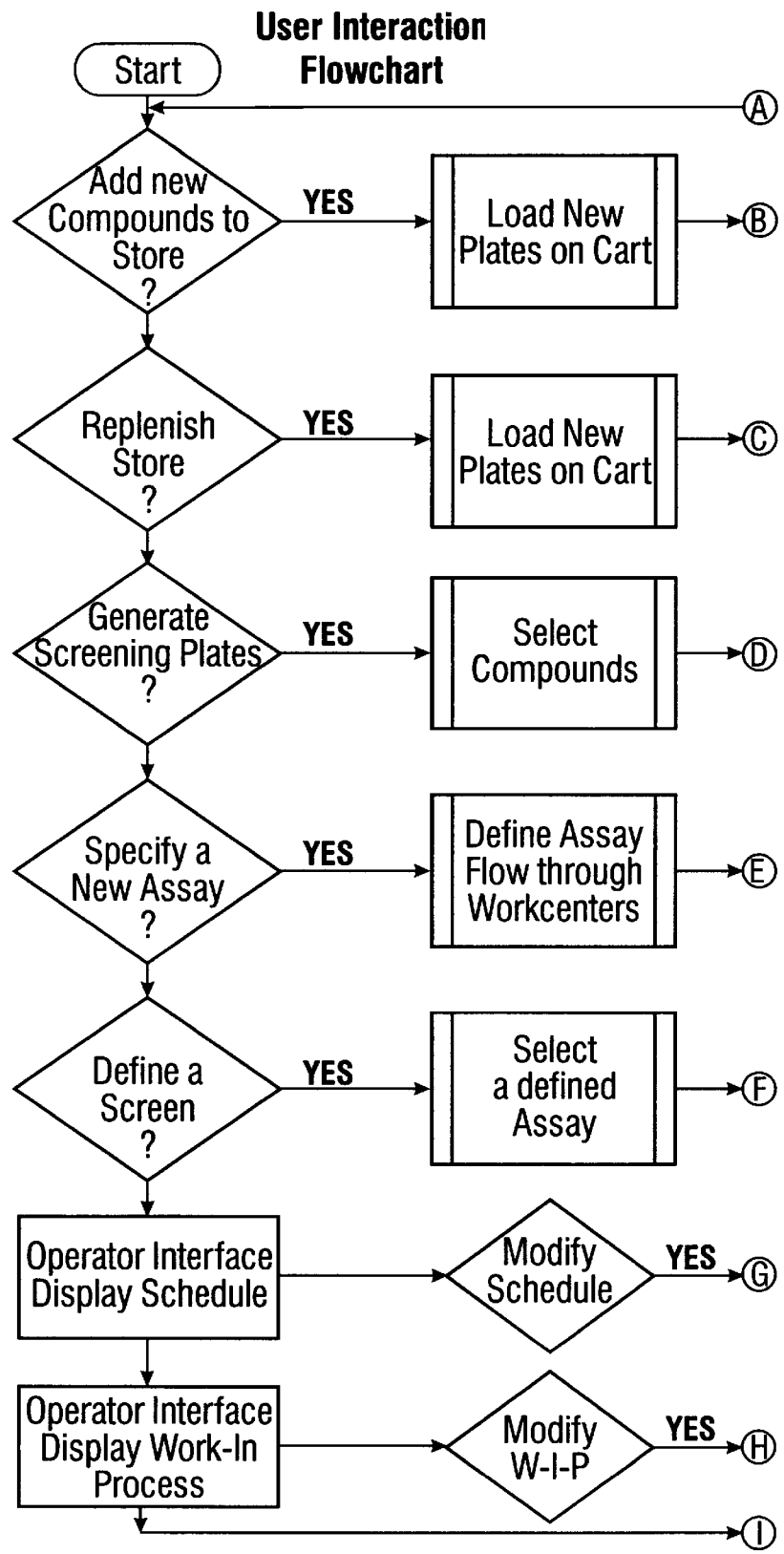
FIG. 13 shows one embodiment of an user interaction flowchart.
Figure 13B:
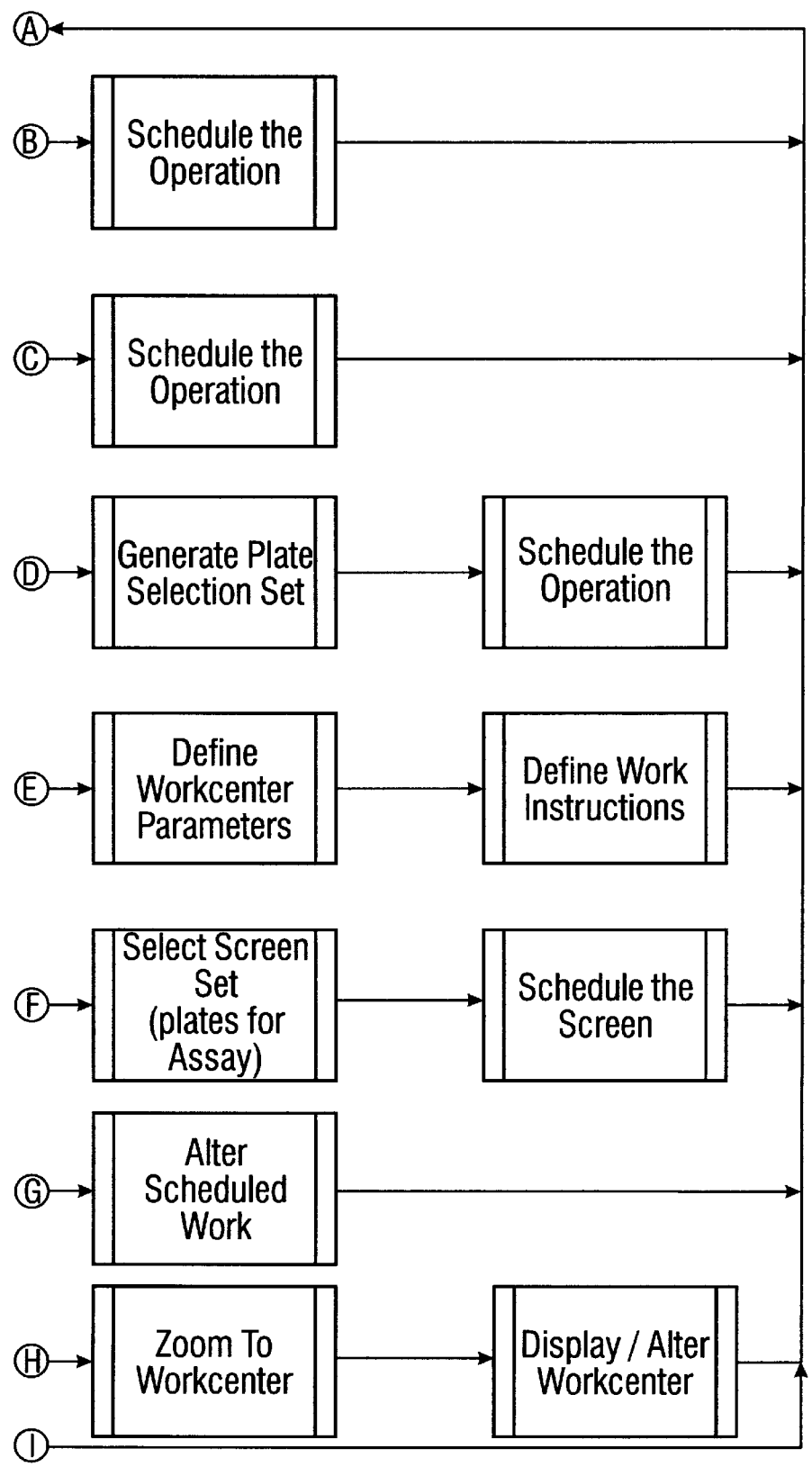

FIG. 13 shows a user interaction flowchart that describes a flow from the user's point of view. Since both a scientist and operator interface are typically provided, the operator of the system is primarily concerned with the momentary operations requirements of the automated units. A single operator interface is normally used. Typical operations that will be included are: (1) compound addition, (2) replenishment, (3) plate generation, (4) defining an assay or procedure, (5) executing a screen, (6) scheduling work, and when no other operation is necessary, (7) observing system operation.

In some embodiments, it will be desirable to include an incubator. An example of such a screening system is shown in FIG. 11. An incubator can have environmental control of atmosphere (e.g., carbon dioxide and oxygen level for cells), humidity, and temperature. Its capacity and ingress and egress points preferably allow for random access by automation.

It is also desirable to operably link an incubator with a transport mechanism such that any plate can be positioned at a common interface point. A conduit (e.g., linear and orthogonal conduit) transports plates within a controlled environment such that as they are requested, they are presented to a common access point. Empty places within this conduit allow new plates to enter the controlled atmosphere. Environmental parameters are measured and controlled via proportional integral, derivative controllers with appropriate sensors. Proportional integral, derivative controllers apply mathematical parameters to react to changes in a measured value and generate a control output.

Methods of Identifying Useful Chemicals

The invention includes methods for identifying useful chemicals. For example, the method can comprise:

A. retrieving from a storage and retrieval module a plurality of chemicals in solution in addressable chemical wells, a reagent well retriever and having programmable selection and retrieval of the addressable chemical wells and having a storage capacity for at least 100,000 of the addressable wells, B. transporting selected addressable chemical wells with a sample transporter to the sample distribution module and the sample transporter optionally having programmable control of transporting of the selected addressable chemical wells, C. aspirating the plurality of chemicals with a sample distribution module comprising a liquid handler to aspirate solutions from selected addressable chemical wells, the sample distribution module having programmable selection of and aspiration from the selected addressable chemical wells, D. dispensing the plurality of chemicals with the sample distribution module using computer programmable dispensation into addressable sample wells, E. transporting the addressable sample wells with a sample transporter to a reagent dispenser module and optionally having programmable control of transporting of the addressable sample wells, F. dispensing at least one assay solution into the addressable sample wells with a reagent dispenser, and G. detecting a signal in the addressable sample wells with a fluorescence detector.

The storage and retrieval module, the sample distribution module, and the reaction module are integrated and programmably controlled by a data processing and integration module; and the storage and retrieval module, the sample distribution module, the sample transporter, the reaction module and the data processing and integration module are operably linked to facilitate rapid processing of the addressable sample wells. Typically, the methods can individually screen at least 25,000 selected and discrete chemicals in addressable sample wells in 24 hours with a single system.

Preferably, chemical libraries are screened such that at least one chemical library of structurally related chemicals. The chemical library is preferably a directed chemical library based on structure activity relationships or chemistry of a specific chemical moiety. Examples of chemical libraries and screening (such random library screening) are described herein and known in the art. The system can also be used to create pools of chemicals.

Preferably, the transporting step is a parallel transport for parallel processing of the addressable wells with the sample transporter. It will be particularly desirable to include adaptive routing, programmably controlled, by the data processing and integration module as part of the method for transporting plates. The transporting can further comprise separating the addressable sample wells from contact with the sample transporter and contacting the addressable sample wells with a X,Y positioner in a workstation, such as a reagent dispenser module. The sample transporter can be a conveyor means that can transport plates about 500 plates per hour across about 3 meters.

The dispensing step can preferably provide for a dilution of about 1,000 to 5,000 fold. Dispensing into small volumes facilitates processing. Volumes less than about 5 microliters for each addressable sample well is particularly useful. The dispensing is into addressable sample wells that typically have a well center to well center distance of less than 5 millimeters and are disposed on a plate with a standard footprint no larger than a standard microtiter plate footprint. The dispensing typically comprises dispensing a predetermined volume of an assay solution comprising a target into the addressable sample wells. The targets can be those described herein, known in the art or developed in the future, for instance from genomics. Targets include proteins such as membrane protein and soluble proteins. The dispensing can also comprise dispensing a predetermined volume of an assay solution comprising an agonist, antagonist or other chemical that interacts with the target to use as a positive or negative control, which can help determine the level of activity of the test chemical. The signal in the addressable sample wells due to the test chemical can be less or more than the control depending on the control. Activity is often measured from a reporter that indirectly or directly indicates the activity of the chemical against the target. In most circumstances, if the reporter produces less of the signal in the presence of a modulator than in the presence of the agonist alone, it can indicate that the modulator is an antagonist. In most circumstances, if the reporter produces more of a signal in the presence of a modulator than in the presence of the antagonist, it can indicate that the modulator is an agonist.

Preferably, a plurality of chemicals is aspirated from selected addressable chemical wells disposed on a first plate with a first density of wells per cm squared. The first plate is then transported away from the liquid handler and addressable sample wells disposed on a second plate, with a second density of wells per cm squared are transported to the liquid handler. The second plate is then positioned for dispensation by the liquid handler. The dispensing of the plurality of chemicals from the selected addressable chemical wells with the liquid handler then proceeds into a first set of selected addressable sample wells disposed on the second plate. The second plate typically has a higher density of wells than the first plate for screening.

Many different assays can be employed with the invention, such as biochemical and cell based assays. Fluorescent probes can be substrates for enzymes, dyes, fluorescent proteins and any other moiety that can produce a fluorescent signal under the appropriate conditions. For example, probes described in PCT application PCT US95/14692 (Tsien), PCT application PCT US96/04059 (Tsien), PCT application PCT US96/09652 (Tsien), and U.S. patent application Ser. No. 08/680,877 (Tsien and Cubitt), U.S. patent application Ser. No. 08/706,408, (Tsien) can be used.

In another embodiment, the invention provides a method of developing a therapeutic chemical. The method comprises: (a) testing a chemical for modulating activity of a target, in a device of the invention, (b) testing the chemical against the molecular target for the modulating activity determined in step (a), (c) testing the chemical or a derivative thereof against a different molecular target for modulating activity, and (d) testing either the chemical or the derivative tested in step (c) in an animal for modulating activity.

Targets

One method of the present invention uses targets for identifying chemicals that are useful in modulating the activity of a target. The target can be any biological entity, such as a protein, sugar, nucleic acid or lipid. Typically, targets will be proteins such as cell surface proteins or enzymes. Targets can be assayed in either biochemical assays (targets free of cells), or cell based assays (targets associated with a cell).

For example, cells may be loaded with ion or voltage sensitive dyes to report receptor or ion channel activity, such as calcium channels or N-methyl-D-aspartate (NMDA) receptors, GABA receptors, kainate/AMPA receptors, nicotinic acetylcholine receptors, sodium channels, calcium channels, potassium channels excitatory amino acid (EAA) receptors, nicotinic acetylcholine receptors. Assays for determining activity of such receptors can also use agonists and antagonists to use as negative or positive controls to assess activity of tested chemicals. In preferred embodiments of automated assays for identifying chemicals that have the capacity to modulate the function of receptors or ion channels (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed, are those disclosed in the Molecular Probes 1997 Catalog, herein incorporated by reference.

Other methods of the present invention concern determining the activity of receptors. Receptor activation can sometimes initiate subsequent intracellular events that release intracellular stores of calcium ions for use as a second messenger. Activation of some G-protein-coupled receptors stimulates the formation of inositol triphosphate (IP3 a G-protein coupled receptor second messenger) through phospholipase C- mediated hydrolysis of phosphatidylinositol, Berridge and Irvine (1984), Nature 312: 315–21. IP3 in turn stimulates the release of intracellular calcium ion stores. Thus, a change in cytoplasmic calcium ion levels caused by release of calcium ions from intracellular stores can be used to reliably determine G-protein-coupled receptor function. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm. Furthermore, there are cyclic nucleotide-gated ion channels, e.g., rod photoreceptor cell channels and olfactory neuron channels (see, Altenhofen, W. et al. (1991) Proc. Natl. Acad. Sci U.S.A. 88: 9868–9872 and Dhallan et al. (1990) Nature 347: 184–187) that are permeable to cations upon activation by binding of cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel and DNA encoding a receptor (e.g., certain metabotropic glutamate receptors, muscarinic acetylcholine receptors, dopamine receptors, serotonin receptors, and the like), which, when activated, causes a change in cyclic nucleotide levels in the cytoplasm.

Any cell expressing a protein target in sufficient quantity for measurement in a cellular assay can be used with the invention. Cells endogenously expressing can work as well as protein expressed from heterologous nucleic acids. For example, cells which may be transfected with a suitable vector encoding one or more such targets that are known to those of skill in the art or may be identified by those of skill in the art. Although essentially any cell which expresses endogenous ion channel or receptor activity may be used, when using receptors or channels as targets it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), Jurkats (ATCC No. TIB 152) and 153 DG44 cells [see, Chasin (1986) Cell. Molec. Genet. 12: 555] human embryonic kidney (HEK) cells (ATCC No. CRL1573), Chinese hamster ovary (CHO) cells (ATCC Nos. CRL9618, CCL61, CRL9096), PC12 cells (ATCC No. CRL17.21) and COS-7 cells (ATCC No. CRL1651). Preferred cells for heterologous cell surface protein expression are those that can be readily and efficiently transfected. Preferred cells include Jurkat cells and HEK 293 cells, such as those described in U.S. Pat. No. 5,024,939 and by Stillman et al. (1985) Mol. Cell. Biol. 5: 2051–2060.

Exemplary membrane proteins include, but are not limited to, surface receptors and ion channels. Surface receptors include, but are not limited to, muscarinic receptors, e.g., human M2 (GenBank accession #M16404); rat M3 (GenBank accession #M16407); human M4 (GenBank accession #M16405); human M5 (Bonner, et al., (1988) Neuron 1, pp. 403–410); and the like; neuronal nicotinic acetylcholine receptors, e.g., the human $\alpha_2$, $\alpha_3$, and $\beta_2$, subtypes disclosed in USSN 504,455 (filed Apr. 3, 1990, which is hereby expressly incorporated by reference herein in its entirety); the human $\alpha_5$ subtype (Chini, et al. (1992) Proc. Natl. Acad. Sci. U.S.A. 89: 1572–1576), the rat $\alpha_2$ subunit (Wada, et al. (1988) Science 240, pp. 330–334); the rat $\alpha_3$ subunit (Boulter, et al. (1986) Nature 319, pp. 368–374); the rat $\alpha_4$ subunit (Goldman, et al. (1987) Cell 48, pp. 965–973); the rat $\alpha_5$ subunit (Boulter, et al. (1990) I.

Biol. Chem. 265, pp. 4472–4482); the chicken $\alpha_7$ subunit (Couturier et al. (1990) Neuron 5: 847–856); the rat $\beta_2$ subunit (Deneris, et al. (1988) Neuron 1, pp. 45–54) the rat $\beta_3$ subunit (Deneris, et al. (1989) J. Biol. Chem. 264, pp. 6268–6272); the rat $\beta_4$ subunit (Duvoisin, et al. (1989) Neuron 3, pp. 487–496); combinations of the rat α subunits, β subunits and a and p subunits; GABA receptors, e.g., the bovine n, and p, subunits (Schofield, et al. (1987) Nature 328, pp. 221–227); the bovine n, and a, subunits (Levitan, et al. (1988) Nature 335, pp. 76–79); the γ-subunit (Pritchett, et al. (1989) Nature 338, pp. 582–585); the p, and p, subunits (Ymer, et al. (1989) EMBO J. 8, pp. 1665–1670); the 6 subunit (Shivers, B. D. (1989) Neuron 3, pp. 327–337); and the like; glutamate receptors, e.g., rat GluR1 receptor (Hollman, et al. (1989) Nature 342, pp. 643–648); rat GluR2 and GluR3 receptors (Boulter et al. (1990) Science 249:1033–1037; rat GluR4 receptor (Keinanen et al. (1990) Science 249: 556–560); rat GluR5 receptor (Bettler et al. (1990) Neuron 5: 583–595) g rat GluR6 receptor (Egebjerg et al. (1991) Nature 351: 745–748); rat GluR7 receptor (Bettler et al. (1992) neuron 8:257–265); rat NMDAR1 receptor (Moriyoshi et al. (1991) Nature 354:31–37 and Sugihara et al. (1992) Biochem. Biophys. Res. Comm. 185:826–832); mouse NMDA el receptor (Meguro et al. (1992) Nature 357: 70–74); rat NMDAP2A, NMDAR2B and NMDAR2C receptors (Monyer et al. (1992) Science 256: 1217–1221); rat metabotropic mGluR1 receptor (Houamed et al. (1991) Science 252: 1318–1321); rat metabotropic mGluR2, mGluR3 and mGluR4 receptors (Tanabe et al. (1992) Neuron 8:169–179); rat metabotropic mGluR5 receptor (Abe et al. (1992) I. Biol. Chem. 267: 13361–13368); and the like; adrenergic receptors, e.g., human pl (Frielle, et al. (1987) Proc. Natl. Acad. Sci. 84, pp. 7920–7924); human $\alpha_2$ (Kobilka, et al. (1987) Science 238, pp. 650–656); hamster $\beta_2$ (Dixon, et al. (1986) Nature 321, pp. 75–79); and the like; dopamine receptors, e.g., human D2 (Stormann, et al. (1990) Molec. Pharm. 37, pp. 1–6); mammalian dopamine D2 receptor (U.S. Pat. No. 5,128, 254); rat (Bunzow, et al. (1988) Nature 336, pp. 783–787); and the like; NGF receptors, e.g., human NGF receptors ( Johnson, et al. (1986) Cell 47, pp. 545–554); and. the like; serotonin receptors, e.g., human 5HTla (Kobilka, et al. (1987) Nature 329, pp. 75–79); serotonin 5HT1C receptor (U.S. Pat. No. 4,985,352); human 5HT1 D (U.S. Pat. No. 5,155,218); rat 5HT2 (Julius, et al. (1990) PNAS 87, pp.928–932); rat 5HT1c (Julius, et al. (1988) Science 241, pp. 558–564); and the like.

Ion channels include, but are not limited to, calcium channels comprised of the human calcium channel $\alpha_2$ β and/or γ-subunits disclosed in commonly owned U.S. application Ser. Nos. 07/745,206 and 07/868,354, filed Aug. 15, 1991 and Apr. 10, 1992, respectively, the contents of which are hereby incorporated by reference; (see also, WO89/ 09834; human neuronal $\alpha_2$ subunit); rabbit skeletal muscle al subunit (Tanabe, et al. (1987) Nature 328, pp. 313–E318); rabbit skeletal muscle $\alpha_2$ subunit (Ellis, et al. (1988) Science 241, pp. 1661–1664); rabbit skeletal muscle p subunit (Ruth, et al. (1989) Science 245, pp. 1115–1118); rabbit skeletal muscle γ subunit (Jay, et al. (1990) Science 248, pp. 490–492); and the like; potassium ion channels, e.g., rat brain (BK2) (McKinnon, D. (1989) J. Biol Chem. 264, pp. 9230–8236); mouse brain (BK1) (Tempel, et al. (1988) Nature 332, pp. 837–839); and the like; sodium ion channels, e.g., rat brain I and II (Noda, et al. (1986) Nature 320, pp. 188–192); rat brain III (Kayano, et al. (1988) FEBS Lett. 228, pp. 187–1.94); human II (ATCC No. 59742, 59743 and Genomics 5: 204–208 (1989); chloride ion channels (Thiemann, et al. (1992), Nature 356, pp. 57–60 and Paulmichl, et al. (1992) Nature 356, pp. 238–241), and others known or developed in the art.

Intracellular receptors may also be used as targets, such as estrogen receptors, glucocorticoid receptors, androgen receptors, progesterone receptors, and mineralocorticoid receptors, in the invention. Transcription factors and kinases can also be used as targets, as well as plant targets.

Various methods of identifying activity of chemical with respect to a target can be applied, including: ion channels (PCT publication WO 93/13423), intracellular receptors (PCT publication WO 96/41013),U.S. Pat. No. 5,548,063, U.S. Pat. No. 5,171,671, U.S. Pat. No. 5,274,077, U.S. Pat. No. 4,981,784, EP 0 540 065 A1, U.S. Pat. No. 5,071,773, and U.S. Pat. No. 5,298,429. All of the foregoing references are herein incorporated by reference in their entirety.

Chemicals Discovered by the Operation of Components or Systems and Related Compositions The invention includes novel chemicals identified as having activity by the operation of methods, systems or components described herein. Such novel chemicals do not include chemicals already publicly known in the art as of the filing date of this application. Typically, a chemical would be identified as having activity from using the invention and then its structure revealed from a proprietary database of chemical structures or determined using analytical techniques.

One embodiment of the invention is a chemical with useful activity, comprising a chemical identified by a system as having modulating activity of a molecular target. The system is a device for rapidly processing liquid samples, comprising: (a) a storage and retrieval module, comprising storage locations for storing a plurality of reagents in solution in addressable chemical wells, a reagent well retriever having programmable selection and retrieval of the addressable chemical wells and having a storage capacity for at least 100,000 addressable wells, (b) a sample distribution module comprising a liquid handler to aspirate or dispense solutions from selected addressable chemical wells, the sample distribution module having programmable selection of, and aspiration from, the selected addressable chemical wells and programmable dispensation into selected addressable sample wells and the liquid handler can dispense into arrays of addressable wells with different densities of addressable wells per centimeter squared, (c) a sample transporter to transport the selected addressable chemical wells to the sample distribution module and optionally having programmable control of transport of the selected addressable chemical wells, (d) a reaction module comprising either a reagent dispenser to dispense reagents into the selected addressable sample wells for reaction or a fluorescent detector to detect chemical reactions in the selected addressable sample wells, and (e) a data processing and integration module. The storage and retrieval module, the sample distribution module, and the reaction module are integrated and programmably controlled by the data processing and integration module; and the storage and retrieval module, the sample distribution module, the sample transporter, the reaction module and the data processing and integration module are operably linked to facilitate rapid processing of the addressable sample wells. The device can process at least 25,000 addressable wells in 24 hours. The invention also includes methods of modulating targets in cells (e.g., in vivo or in vitro) with compounds identified as having modulating activity by the inventions.

The invention also includes compositions comprising a chemical identified by systems described herein as having modulating activity of a target. The composition includes a carrier for the chemical. Most chemicals in such compositions will be at least 50% pure by weight, preferably at least 80% pure by weight, more preferably at least 95% pure by weight, and most preferably at least 99% pure by weight. Although natural products and combinatorial chemistry products often have purities lower than 80% by weight.

Such chemicals include small organic molecules, nucleic acids, peptides and other molecules readily synthesized by techniques available in the art and developed in the future. For example, the following combinatorial compounds are suitable for screening: peptoids (PCT Publication No. WO 91/19735, Dec. 26, 1991), encoded peptides (PCT Publication No. WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909–6913 (1993)), vinylogous polypeptides (Hagihara et al., J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al., J. Amer. Chem. Soc. 116:2661 (1994)), oligocarbamates (Cho, C.Y. et al., Science 261: 1303 (1993)), and/or peptidyl phosphonates (Campbell, D.A. et al., J. Org. Chem. 59: 658 (1994)). See, generally, Gordon, E. M. et al., J. Med Chem. 37: 1385 (1994). The contents of all of the aforementioned publications are incorporated herein by reference.

Pharmaceutical Compositions

The present invention also encompasses pharmaceutical compositions prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art. Typically, human clinical applications of products are commenced at lower dosage levels, with dosage level being increased until the desired effect is achieved.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 kg/kg and 100 mg/kg body weight, preferably between about 100 kg/kg and 10 mg/kg body weight. Administration is preferably oral on a daily basis.

The exact formulation, route of administration and dosage can be chosen by the individual physician in view of the patient's condition. (See e.g., Fingl et al., in The Pharmacological Basis of Therapeutics, 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses.

Computer Program Product, Computational Methods, Databases and Storage Devices Based on Infonnation Generated by the Operation of Components or Systems In one embodiment, the invention provides for a computer program product for processing samples and methods. The computer program product can include many of the methods described herein such as those methods related to databases, workflow, structure activity relationships, computer interfaces, identification of chemicals, parallel processing and adaptive routing.

For example, the invention includes a computer program product, comprising a computer useable medium having computer program logic recorded thereon for enabling a computer processor in a system to assist in performing a liquid sample process having a predetermined set of liquid sample process properties, the system comprising a storage and retrieval module to store and retrieve, in accordance with store and retrieve instructions, a plurality of addressable wells; a sample transporter to transport, in accordance with transport instructions, a plurality of addressable wells, and a reaction module to react chemicals or to detect a physical property, in accordance with reaction or detection instructions, in a plurality of addressable wells. The computer program logic comprises:

A. a workflow model means for enabling the computer processor to define the process properties of integrated components of the system to enhance distribution of workflow in the system, and B. a processing instruction means for enabling the computer processor to generate processing instructions for routing workflow comprising: 1) store and retrieve instructions, 2) transport instructions, and 3) reaction and detection instructions that, when executed, enable the system to rapidly process addressable wells.

In another embodiment the invention includes a database for computational analysis of chemical structure and activity against targets, comprising activity data of discrete chemicals. The data is stored on a computer accessible storage media. The data is generated by a system that can test for modulating activity of a molecular target. The system is a device for rapidly processing liquid samples, comprising a storage and retrieval module comprising racks for storing a plurality of chemicals in solution in addressable chemical wells, a chemical well retriever and having programmable selection and retrieval of the addressable chemical wells and having a storage capacity for at least 100,000 of the addressable wells, a sample distribution module comprising a liquid handler to aspirate or dispense solutions from selected the addressable chemical wells. The sample distribution module has programmable selection of and aspiration from the selected addressable chemical wells and programmable dispensation into addressable sample wells. The liquid handler of the sample distribution module can dispense into arrays of addressable wells with different densities of addressable wells per centimeter squared. It also includes a sample transporter to transport the selected addressable chemical wells to the sample distribution module that optionally has programmable control of transport of the selected addressable chemical wells and a reaction module comprising either a reagent dispenser to dispense reagents into the addressable sample wells for reaction or a fluorescent detector to detect chemical reactions in the addressable sample wells, and a data processing and integration module. The storage and retrieval module, the sample distribution module, and the reaction module are integrated and programmably controlled by the data processing and integration module; and the storage and retrieval module, the sample distribution module, the sample transporter, the reaction module and the data processing and integration module are operably linked to facilitate rapid processing of the addressable sample wells. The device can process at least 25,000 addressable wells in 24 hours. Other database related embodiments are contemplated with other systems described herein, as well as methods using the databases and storage devices storing the database.

EXAMPLES

Example 1 —Screening Sample Distribution Module

The screening sample distribution module permits the preparation of plates with chemicals, such as test chemicals from addressable chemical wells and biological reagents (e.g., cells or isolated molecular targets). The primary function of the screening sample distribution module is to aspirate solutions from one plate and transfer them into another plate. This is usually accomplished with an array of liquid handlers (e.g., liquid handling head), preferably an array of at least about 50, more preferably at least about 100 and most preferably at least about 200. The array is most preferably M liquid handlers by N liquid handlers, wherein M is the number of addressable wells in a column on a plate or an integer multiple thereof and N is the number of addressable wells in a row on such plate or an integer multiple thereof (wherein M and N preferably have the same integer multiple), as described herein. The sample distribution module can be integrated in a screening system, for example, as shown in FIG. 1 with a data processing and integration module. The screening sample distribution module can be operably linked to other workstations with a sample transporter, which is also shown in FIG. 2. The sample distribution module for both aspiration and dispensing in one embodiment comprises, dispensers, stackers, a liquid, a reader and a conveyor.

Dispensers

In one embodiment the screening sample distribution module was designed with a liquid handler, having. 96-dispensers that can use positive displacement disposable tips in 200 $\mu L$, 50 $\mu L$ and 20 $\mu L$ volumes. A disposable 200 $\mu L$ tip head can deliver a range of volumes of 1 $\mu L$ to 200 $\mu L$, with precision and accuracy of 10% at 1 $\mu L$ to 3% at 200 $\mu L$. An optional disposable 20 $\mu L$ tip can deliver a range of volumes of 0.1 $\mu L$ to 20 $\mu L$, with precision and accuracy of 10% at 0.1 $\mu L$ to 3% at 20 $\mu L$. The dispenser can move in Z-axis (vertical axis, i.e. perpendicular to plane of a floor), which is controlled with a Z-positioner and has a travel distance from below a conveyor, to access a wash station or reagent trough, to above the conveyor. Preferably, a lidded deep well plate can pass underneath (about 3 to 5.5 cm in distance). The dispense axis (the axis with respect to volume displacement) will be at least 10,000 steps (servo motor) to displace the full pipetting volume. Dispensing speeds are controlled by positive movement of a shaft and are controllable from 1 mm/second to 50 mm/second. The resolution of the z-axis will be at least 25,000 steps over 75 mm travel from below the conveyor to a fully retracted position. Positional feedback may be required for both z and d-axis (dispense axis), such as encoders, liquid level and limit switches. Both axes will be capable of simultaneous and concurrent operation independent of each other. The dispenser assembly must be continuously adjustable (no détentes or stops) in "X" and "Y" with a +/−10.0 mm positioning capability with respect to a plate conveyor. Dispensers can accommodate a flowing wash station and a refilling reagent trough. The dispensers can accommodate 384-well plates, well as 96-well plates. Dispensers can be a piezo device or a solenoid described herein or known in the art or developed in the future.

The liquid level for both aspirating and dispensing can be monitored by placing a sensor on or near the tip of the liquid handler, such as an electrical sensor. For example, the capacitive sensor described in U.S. Pat. No. 5,365,783 (Zweifel) can be used, as well as other suitable sensors known in the art. Such methods can also be applied to other liquid handling devices described herein.

Stacker Magazines

In one embodiment, the screening sample distribution module was designed with a stacker magazine having a capacity of about 50 standard microplates. Bi-directional stacking with lidded or unlidded plates is desirable. The stacker magazine can accommodate either standard height plates or deep well plates in a given stack and plate types will typically not be mixed in a stack.

Lidder

In one embodiment, the screening sample distribution module was designed with a bi-directional plate delidder and relidder. The lidder removes and replaces plate lids at a rate of about 5 to 11 plates per minute in one direction. The lidder can store approximately 60 lids. Preferably, a modified lid is used for separation.

Bar Code Reader

In one embodiment, the screening sample distribution module was designed with a bar code reader to scan incoming plates and verify plate location in the screening sample distribution module and to permit location of an addressable well. Typically, bar codes are detected to locate plates before any manipulation is performed. Bar code labels were positioned on the narrow end of the plates, column 12 side, and will be 3 to 1 ratio, 0.25"×1.0", 10 mil bar code 128, from Intermec, Everett, Wash.. Misread or unreadable labels will produce an error code available to the supervisory control system. Labels and adhesive must resist the action of solvents and environmental conditions.

Conveyor

In one embodiment, the sample distribution module was designed with a bi-directional conveyor transport plates within the sample distribution module. It can be optionally used to transport plates for movement between module components (e.g., dispenser head assembly and stacker magazines). The conveyor operates at a speed allowing a transit time between modules of 2–4 seconds or less. Gates are available for arresting plates at predetermined module positions. Detaining of a plate on the conveyor by a gate will not cause the plate to vibrate or move such that the module associated with that position fails to perform its function. Conveyors for a sample distribution module are preferably belt-driven and allow a rotating belt to contact a plate bottom.

Interfaces/Communication

Figure 6B:
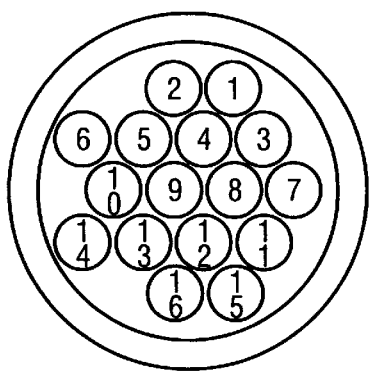

In one embodiment, the screening sample distribution module was designed with a (programmable logic controller with ladder logic) having a minimum of two RS-232 ports open for external communication and programming (or GPIB interfaces). The programmable logic controller with ladder logic will have an ethernet communication card enabling the programmable logic controller with ladder logic to communicate with another computer via transmission control protocol/internet protocol. The programmable logic controller with ladder logic will have four discrete inputs and three discrete outputs open for handshaking to a conveyor system. The conveyor control logic is written to conform to the handshaking logic outlined in FIG. 6. The sample duplication robot E-Stop switch must be a dual pole design to allow an external E-Stop loop to be wired through the switch.

Error Conditions

Failure of the sample distribution module to perform any programmed function within an allotted time will also constitute an error. Performance of a function outside of measurable parameters will also constitute an error. Errors will be corrected automatically when within the ability of the instrument to do so. Unrecoverable errors can notify the user via both the touch screen and the external link, and will set the handshaking logic to refuse further plate input, until the error is corrected. For given families of error conditions, a response can be specified, e.g., for recoverable errors, bar code errors. For errors that are automatically recoverable, response parameters will exist to either pause the instrument and report the error, or to automatically recover from the error, report/log the error and resume operation. Recoverable errors will have a time-out function to halt recovery, if time exceeds a configurable value.

Functional Capability

The control software can control the parameters as specified in Table 3, via an interface. Level two will facilitate the same function via an external computer.

TABLE 3

| Bar Code | Conveyor | Delidder | Aspirate | Aspirate Range | Dispense | Dispense Range | Stacker |
|---|---|---|---|---|---|---|---|
| Read | ON/OFF | Up/Down | Z Height (mm) | −30 to 60 | Z Height (mm) | −30 to 60 | Up/Down |
| Compare | Forward/Reverse | | Volume (µL) | 0 to 200 | Volume (µL) | 0 to 200 | |
| Exception | | | Speed (%) | 0 to 100 | Speed (%) | 0 to 100 | |
| | | | Overfill (µL) | 0 to 200 | | | |
| | | | Air Gap (µL) | 0 to 200 | | | |
| | | | Pre-Dispense (µL) | 0 to 200 | | | |
| | | | Plate/Bath | 0 or >0 | | | |

Replication/Expansion (Master to Multiple Daughters) A master plate can be distributed into one or more daughter plates. The master plate is aspirated from one or more of the pipetting stations in the sample distribution module. Daughter plates are positioned under these pipettors. If the replicate volume is large, e.g. volume x replicate number is greater than the tip volume, then multiple aspirations from the master are required. Additionally, it is often faster to bring in four masters and then four daughters (one for each master) and repeat this until each master is replicated completely. The master may also be 384 and the replicates 96-well plates. If this is the case, the only difference is that the master must travel under each pipettor to access each quadrant. Later the master could be 864-well and have nine daughters produced. Pooling/Compression (Multiple Masters to a Single Daughter) Multiple master plates are positioned under separate pipettors. A single daughter is dispensed to by each pipettor. This may be in the same wells or separate wells of a 384-well plate or greater density. Pooling could consist of more than four masters being combined to a single daughter, this would require the daughter to be sequestered while new masters were aspirated from. Later this could be at least 36 masters to one 3,456-well plate.

Example 2 —Plate Handling and a Sample Transporter

The screening system typically operates on a work unit (unit) with a standardized processing format. The work unit sometimes embodies a particular processing format, such as a plate. Such work units often vary in external dimensions, materials of construction, physical design and density (or number of wells). The screening system is preferably constructed using workstations to handle a standard processing format that allows for a flexible work unit. This approach reduces the need for complete uniformity of the work unit, as is required in many laboratory automation and discovery systems. Consequently, a screening system can function with a mixture of many work units without adjustment or calibration. This permits the system to universally handle varying work units of a standardized processing format. The sample transporter preferably comprises components that permit universal plate handling. The sample transporter can be used to operably link workstations together as shown in FIG. 11.

Typically, a storage and retrieval module and operably linked sample transporter include a storage and retrieval end actuator, universal stacker/destacker, transport system elementsand the registration device that are designed to handle work units with a standardized processing format. Preferably, to enhance workflow and throughput, these all the devices that handle work units that are designed to handle the same standard plate footprint.

Figure 14:
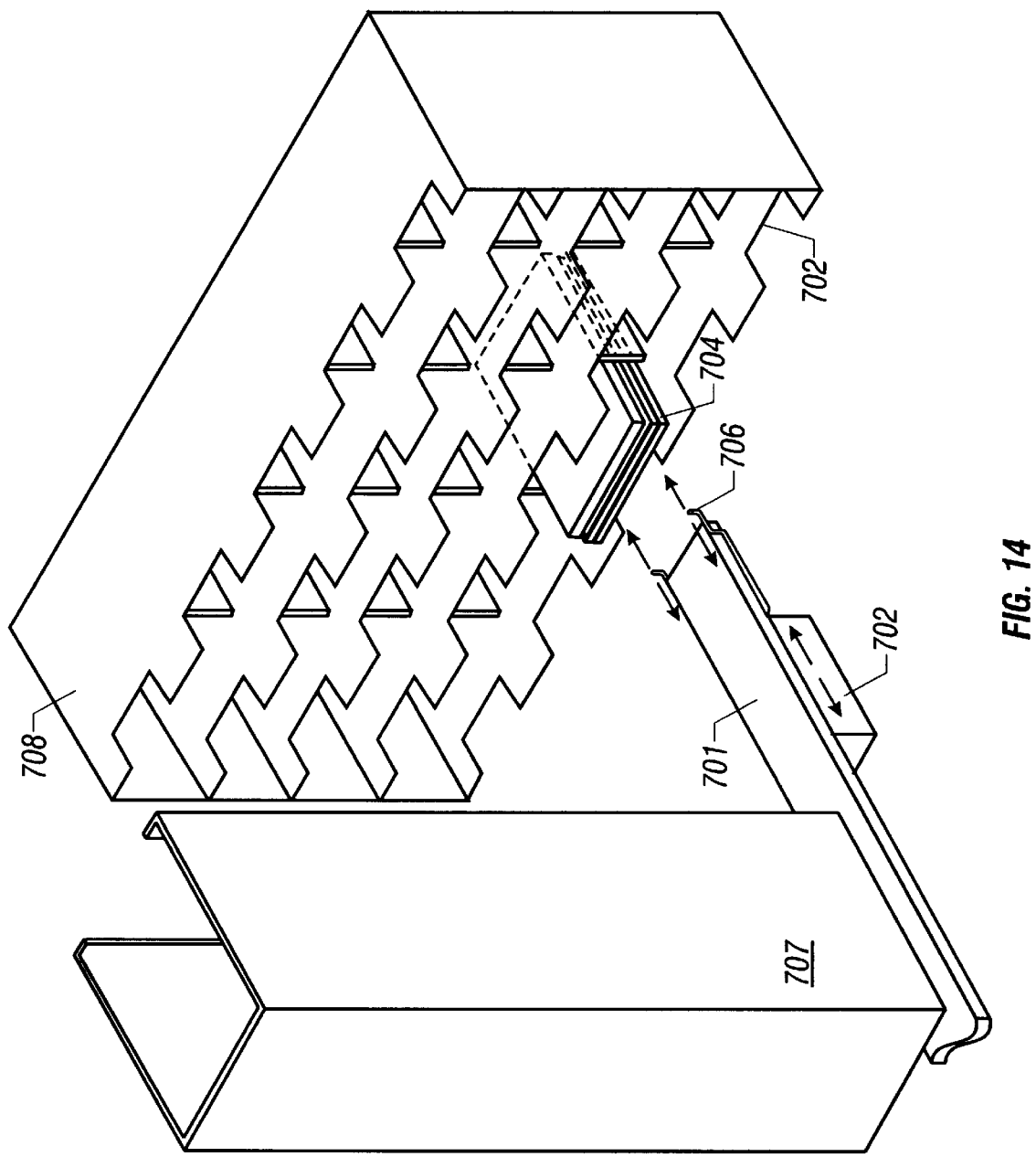
FIG. 14 shows one embodiment of a storage and retrieval end actuator.

FIG. 14 shows part of a storage and retrieval end actuator with part of a storage and retrieval module. The storage and retrieval end actuator can be used as a universal end actuator and adapted to move a work unit with a standardized processing format. For example, an storage and retrieval end actuator can be a component of the storage and retrieval module to retrieve wells. A design preference of the storage and retrieval module is to maximize the number of units that can be contained in a given vertical and horizontal space. It is undesirable to allow access space on either side of the work unit. The storage and retrieval end actuator provides the advantage, compared to many actuators, of not requiring any horizontal space to move a plate.

To retrieve a work unit from a storage and retrieval module, the storage and retrieval end actuator can be positioned in front of a particular hotel within the storage and retrieval module using an X and Z positioner. In FIG. 14, the platen 701 is positioned within a notched hotel shelf 702 in the hotel 708 enclosure, but slightly below the work unit 704. A drive means 703, extends or retracts push/pull hooks 706 to the end of the platen under the work unit. At this point, the X and Z positioner raises the platen a small amount, engaging the hooks beneath the work unit 704. Work units should have an opening(s) that will engage the hooks. A push/pull means operates to pull the work unit onto the platen. Its travel allows the unit to be centered on the platen for the subsequent upstack operation in the end actuator's stacker 707. Guides can be fitted, which are not shown, to center the unit on the platen. An advantage of the storage and retrieval end actuator is that it can operate on any work unit that has an opening, such as a concave or hollow bottom found on commercially available plates. The storage and retrieval end actuator does not require any other physical dimension or special tooling of the work unit, although it may be preferred.

The placement of a work unit in the storage and retrieval module (or on a sample transporter) is similar, except the push/pull hooks are positioned to allow the push/pull hooks to push the work unit by its front edge into the notched hotel shelf. To store a work unit, the platen is positioned slightly above the floor of the notched hotel shelf. The storage and retrieval end actuator can be optionally configured with a detector that identifies a work unit by its bar code or other identifying marking.

A universal stacker/destacker that can handle work units, e.g., plates, by stacking or destacking a plurality of units, both with and without lids. It can often act as a buffer between an storage and retrieval module and the sample transporter. The universal stacker/destacker should minimize the height of a completed stack. Ideally, stack height should not be any more that the sum of the height of the stacked units. The universal stacker/destacker should also be able to accept plates of different heights. Plates can vary in height depending on the well capacity (typically between 1.2 cm and 5.5 cm). Therefore, a separator device is largely unacceptable. Stacking and destacking can be accomplished by a plate lifter that can bottom load and bottom unload a plate in a stack, while maintaining the position of the stack. Alternatively, the universal stacker/destacker may move down or up and the platen maintain its Z- position. Plates are kept in place by either providing a plate holding means disposed on the universal stacker/destacker frame or a plate holding means disposed on a platen (e.g., as depression on the platen into which a single plate falls while leaving behind the remainder of the stack when the platen is withdrawn). Preferably, the universal stacker/destacker should also be able to release an entire stack, if transport of the entire stack is desired.

Figure 15A:
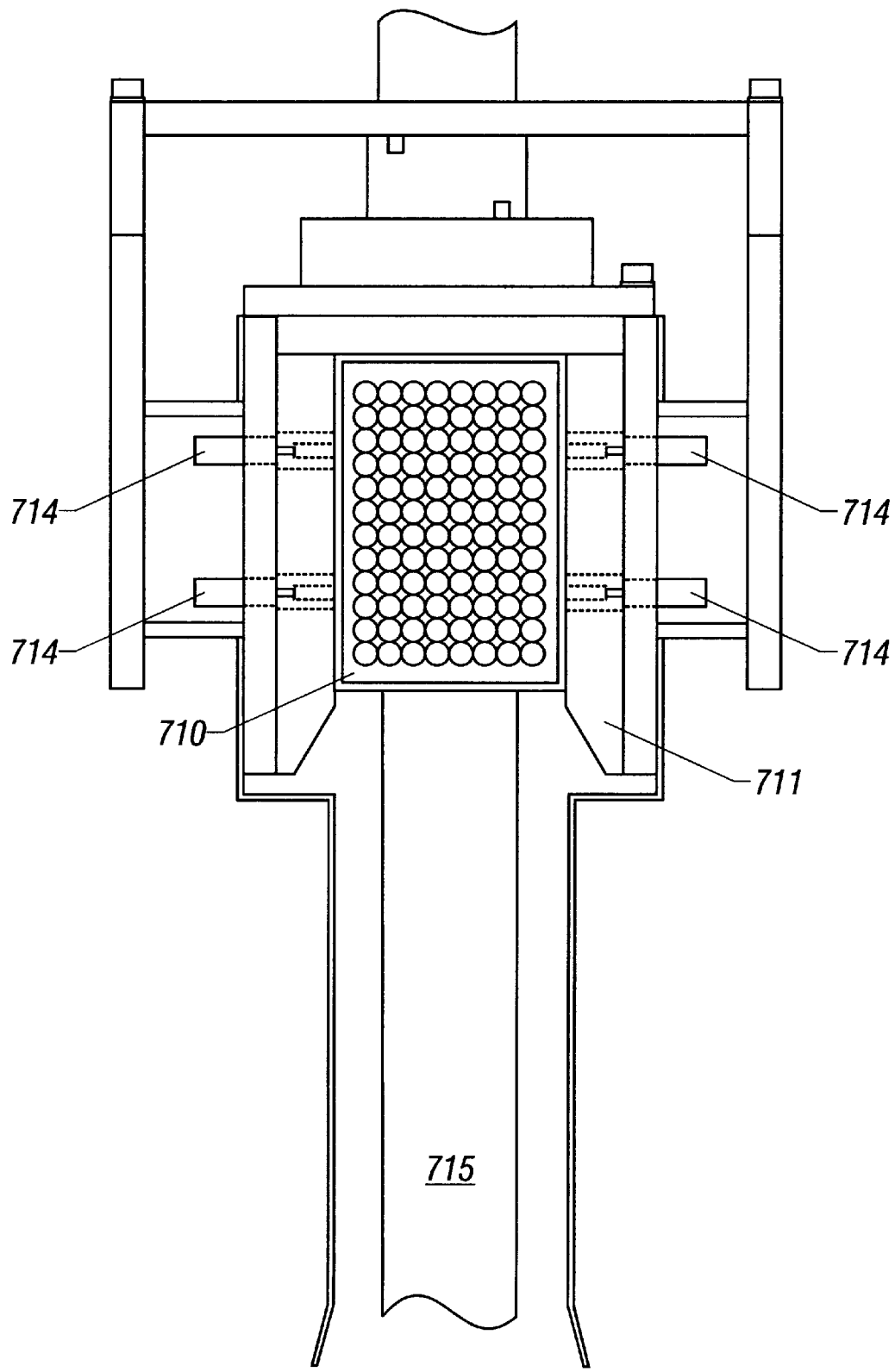
FIG. 15A and 15B shows one embodiment of a universal stacker.
Figure 15B:
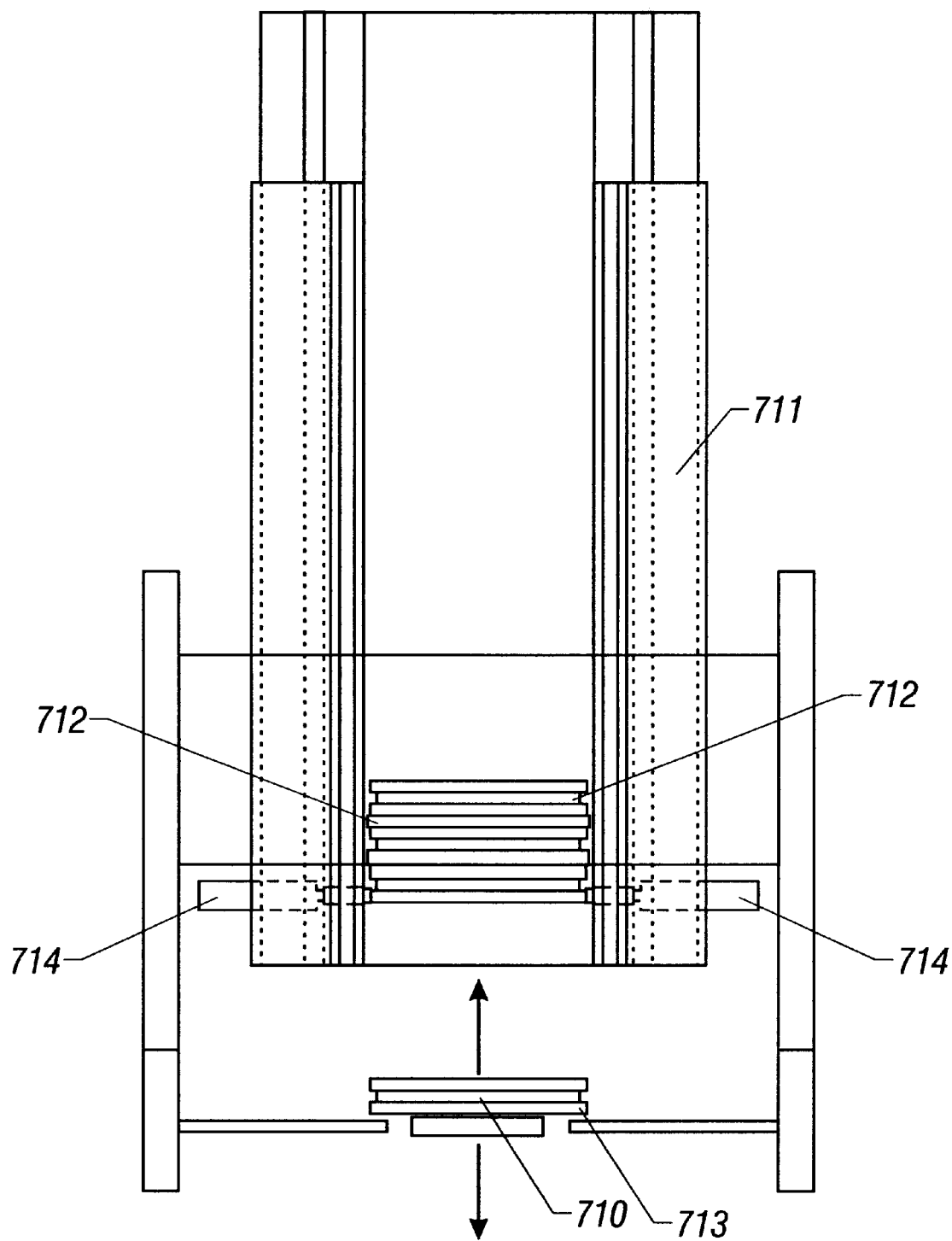

FIG. 15A (plan view) and FIG. 15B show a Universial stacker/destacker with a work unit 710 (shown with a lid) on a platen 715. To stack the work unit the platen is vertically lifted into the frame of the universal stacker/destacker. The amount of vertical lift distance can be a calculated distance based on the type of work unit. This value can then be used by the data processing and integration module to control the vertical lift of the platen. This information can be contained in the data processing and integration module Data Store and can be used to drive a work unit's unit Z-positioning device. The work unit is guided by a three sided stack enclosure 711. As the work unit is lifted, it may come in contact with pressure pins 714 either indirectly (with another work unit above it that is engaged by pressure pins 714) or directly, if no work unit is above it. Once the work unit is lifted sufficiently, pressure pins 714 release the work unit immediately above the newly entered work unit and engage the new work unit. The new work unit, and all higher stacked units 712 are then raised a calculated distance to securely engage the lower skirt of a plate 713 with pressure pins 714. The pressure pins can engage the work units with a preset pressure based a retractable spring or spring like mechanism or a variable pressure based on a retractable piston that is computer-controlled to permit release or engagement of work units.

Down stacking is accomplished in a reverse manner. Pressure pins are actuated and released by compressed air. Lid information is included in the calculations, so that there is never interference with lidded units. The entire stack may be transferred to the input/output station by releasing the pressure pins 714 and allowing the platen 715 to transfer the entire stack.

Figure 16A:
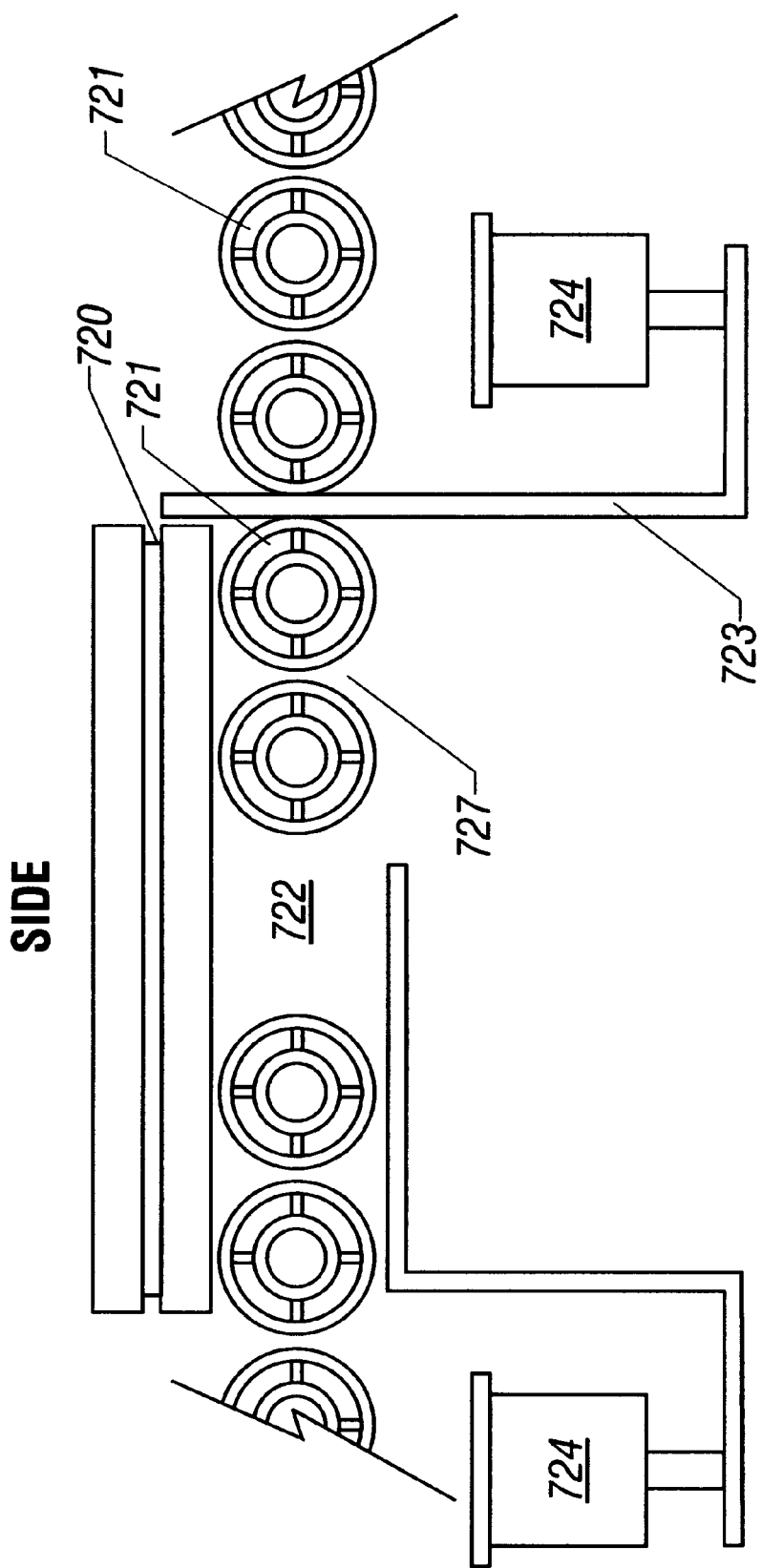
FIG. 16A and 16B shows one embodiment of transport system elements.
Figure 16B:
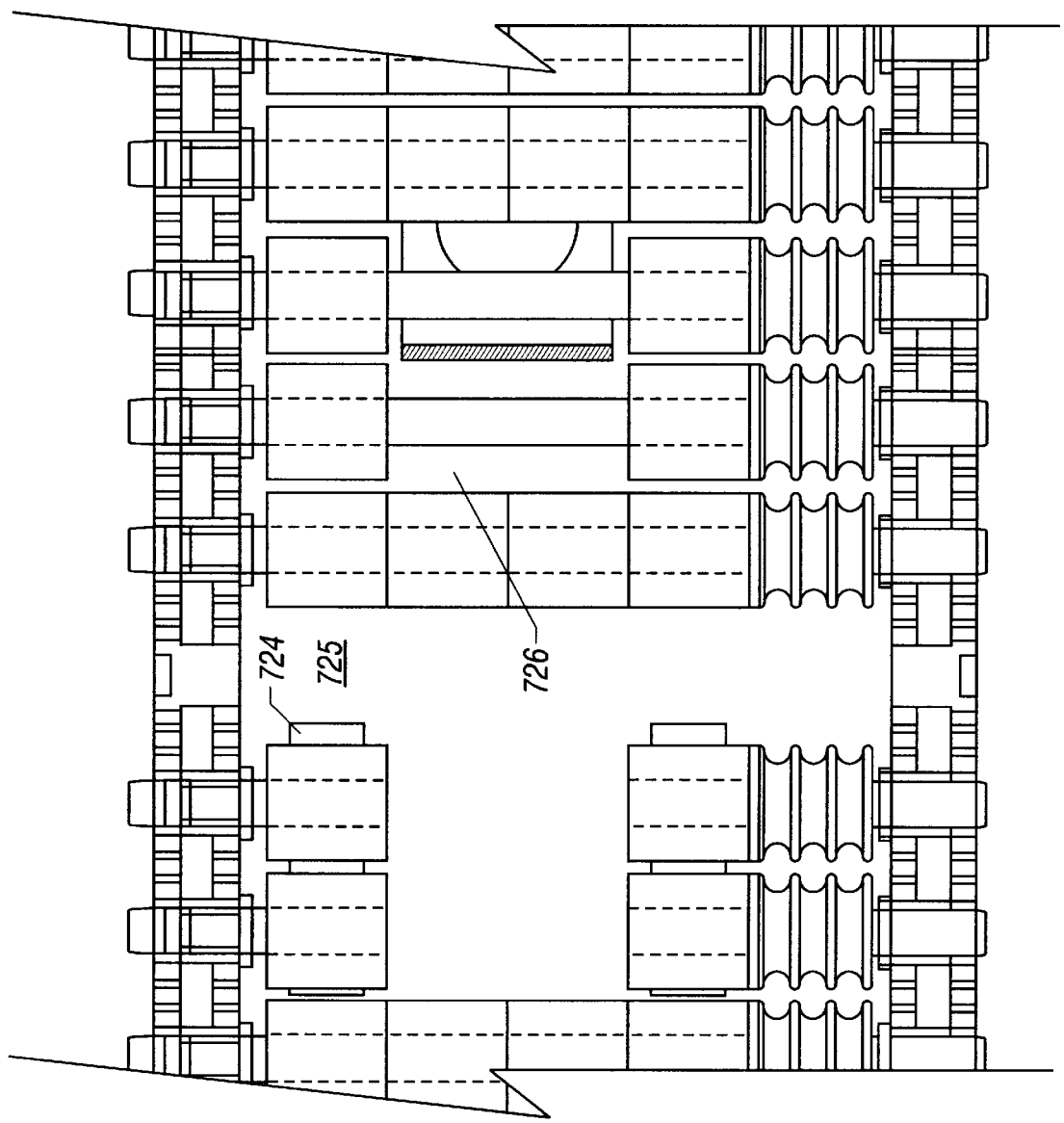

FIG. 16A (side view) and FIG. 16B (plan view) shows the transport system elements 721 in a section of track that can be used in a sample transporter. Transport system elements contact and operate on the bottom of work units 720. Work units are transported on a series of powered transport system elements (e.g., rollers) 721. Typically, at least five rollers are in contact with the work unit 720 during normal transfer. Spaces 722 can exist between the rollers to permit sensing devices or physical actuators to permit sensing or actuation while minimizing disruption of the transfer of work units. Devices can include mechanically actuated stops 723 to stop or direct plates. Brakes 724 can also be provided to stop the rotation of some rollers 721 by engaging the rollers from below. Entire rollers 725 can be eliminated to provide access for a larger sensory apparatus, without reducing the transport efficiency, since the unit can be conveyed on its edges, a flat bed of rollers is not required. Rollers can be eliminated in the center 726 so that the entire bottom surface of the unit, other than its edges, can be acted upon. This can accommodate identification and detector devices. The elimination of rollers (e.g., rollers that do not span the track) or spaces between rollers in a location can be used to dispose a Z-positioner that engages a work unit from its side or bottom. The Z-positioner lifts the work unit off the roller for further positioning (e.g., positioning in a workstation) or lowers the unit onto the rollers (e.g., from a work station).

Rollers are preferably made of a material that minimizes friction with a work unit bottom to minimize the force required to transport a work unit while providing sufficient friction to prevent interfering slippage and to provide accurate stopping at desired locations. Typically, rollers will be made of a polymer relatively inert to solvents, preferably a Telfon™ or Delrin™ is used. Roller friction can be adjusted for certain plates by scoring the surface of the roller with tiny striations. As the number of striations, or the thickness of striations increases, the friction between a roller and work unit increases. Striations should be so large as to not significantly disturb the contents of an addressable well, unless agitation of the wells is desired. Rollers can be used as described in the electronics manufacture arts and as developed in the future for the electronics and other industries. The application of such rollers from the electronics industry to screening and laboratory automation applications, however, is unique.

Example 3 —Hit Profiler

A screening system can include a hit profiling robot (HPR) to prepare test chemicals that show activity in a screen, i.e. hits. The primary function of the hit profiling robot is to reformat "hits" from source plates (e.g., a master or daughter plate) into secondary (or destination) plates for confirmation of activity and profiling the hit, such as an EC50. Typically, the hit profiling robot is capable of handling 96 and 384-well plates, and preferably 3,456-well plates, and it has liquid handling heads that can aspirate from standard height and deep well plates. A delidder/relidder can be included to remove and replace lids on plates with lids prior to, and after, aspiration. As shown in FIG. 2 the hit profiling robot can be integrated to other workstations using a data processing and integration module and operably linked to other workstations with the sample transporter.

The hit profiling robot can be controlled by either a computer that allows for selection of pre-defined methods by end users, or end users may create an entirely new method. Typically, a plurality of addressable wells containing the desired chemical are selected, at least one liquid handling head is directed to aspirate a solution from an addressable well and dispense the solution into at least one other addressable well, such as a well of a secondary plate. For most applications the number of source plates used to produce a secondary plate will vary and the hit profiling robot can be designed to hold multiple source plates in a stacker. Typically, source and destination plates will have different heights and densities. To aspirate and dispense into plates of varying heights the hit profiling robot has liquid handling heads mounted on a Z-positioner or, alternatively, the plates can be securely retained on a Z-positioner and the liquid handling heads held in place. The computer that controls the hit profiling robot can also report of success, failure and errors related to the hit profiling robots function.

Figure 17:
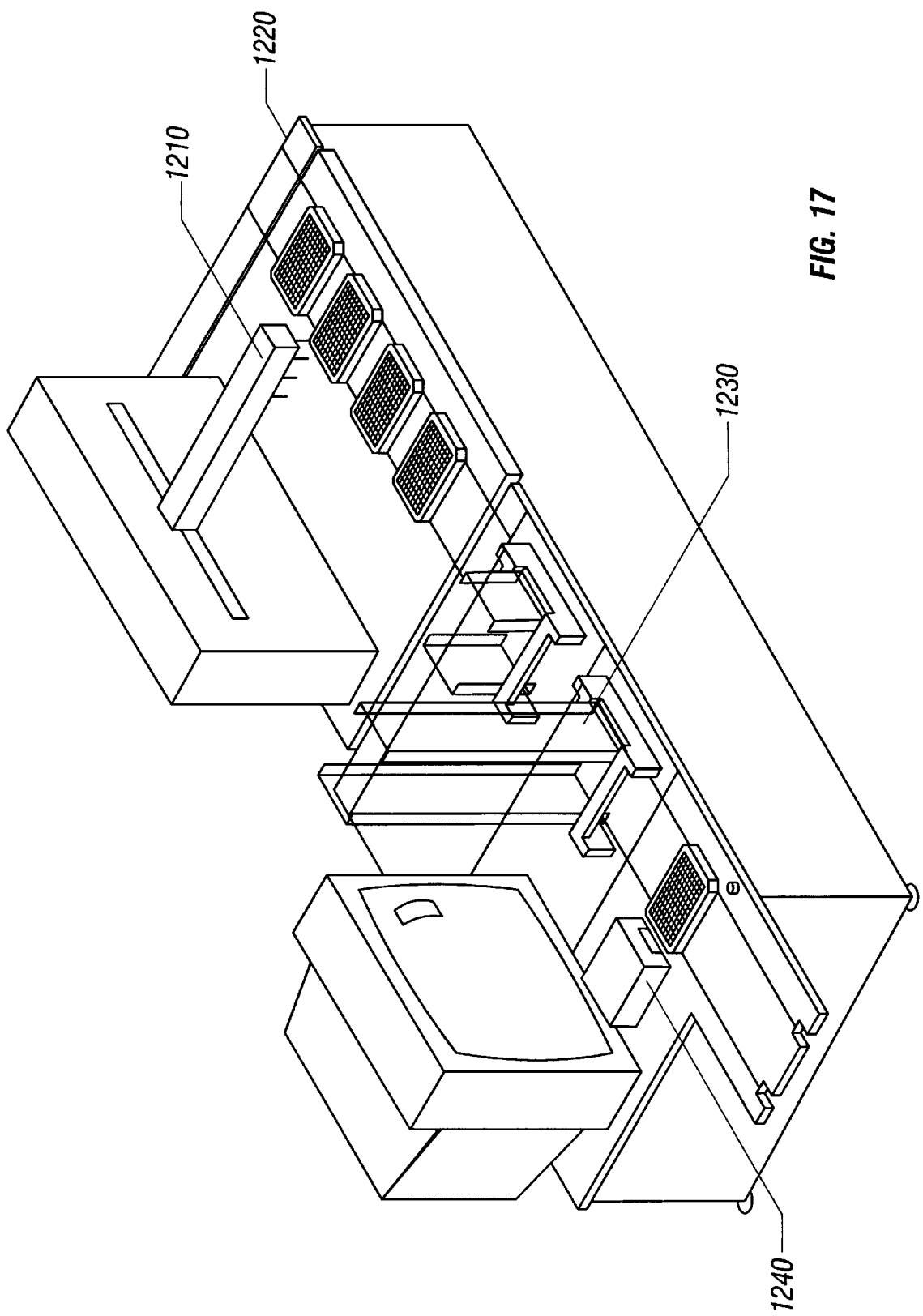
FIG. 17 shows one embodiment of a hit profiling workstation.

FIG. 17 shows an HPR with articulated 4-particular dispensers 1210 that can use positive displacement dispensers. The dispense axis is comprised of at least 3,000 steps over the full pipetting volume using a servo motor. The resolution of the X-axis is at least 100 microns and is achieved by an X,Y positioner. Positional feedback is used for all axes and achieved with computer-controlled X,Y positioner and Z positioner. This type of control allows for single wells to be accessed, by moving unused heads out of position. Pipetting speeds are electronically controlled. The liquid handling heads can be suitable liquid handling devices described herein, including solenoid and piezo based devices, as well as an other low volume liquid handling devices known in the art or developed in the future. Pipetting volumes typically range from 1 to 2,000 nanoliters, and picoliters volumes can be achieved with piezo heads (e.g., 10 to 500 picoliters). The liquid handling head can optionally sense the liquid level for both aspirating and dispensing using either capacitance or resistivity sensors. Such sensors can provide minimum tip exposure to liquids. Tips are optionally replaceable. Single undiluted samples from one or more wells of the source plates are transferred to the destination plate. Dilution series could be generated from the source plates into the destination plate. Stackers 1230 can be included and accessed with a conveyor 1220.

A flowing wash station and refilling reagent trough can also be included. This will reduce carryover, which is usually no greater than 100 ppm. The volume, duration and flow for probe washing are computer-controlled.

The hit profiling robot can include an identification code system, such as a bar code reader to scan incoming plates. The bar code reader 1240 is located to read plates before any other manipulation is performed and bar code identification is confirmed upon plate arrival.

Plates are transported to the hit profiling robot using a bidirectional conveyor, which can operably link the hit profiling robot to other modules (see FIG. 2). The conveyor can operate at a speed that provides for a transit time between modules of 2.5 seconds or less. Gates can arrest plates at predetermined module positions. Gates arrest plates on the conveyor with minimal vibration and movement to prevent the plate from being transferred improperly to a module. A movement function will allow a destination plate to be "parked." The hit profiling robot will integrate into a conveyor transport system using a means for transferring a plate to the hit profiling robot. Alternatively, the hit profiling robot can work in a stand alone fashion.

In operation the hit profiling robot can perform simple reformatting of plates (i.e. transferring solutions from one plate density to another), reformatting with dilution, and reformatting with pooling. For example, the hit profiling robot can transfer solutions from multiple source pates to a single destination plate. Alternatively, the hit profiling robot can perform pooling (or compression) of multiple master plates to a single daughter plate. Multiple master plates are positioned under separate liquid handling heads and a single daughter plate is made by each liquid handling head. This may be in the same wells or separate wells of a 384-well plate. For instance, pooling could consist of more than four master plates being combined into a single daughter plate. This requires the daughter plate to be sequestered while the master plates are being aspirated.

Example 4 —High Capacity Stacking System (HCSS)

The screening system preferably includes a high capacity stacking system (HCSS) that can act as a plate buffer (buffer). The HCSS comprises a two-dimensional array of plate stacks. Plates are accessed from the bottom. The lowermost plate can be randomly accessible by positioning multiple stacks over a plate transport conveyor and upstacking or downstacking from a first stack to a second stack (e.g., shuffling plates between stacks to retrieve a desired plate). The high capacity stacking system provides a 500 plate capacity when implemented with a 2 (plate transport conveyors)×5 (stacks) array of 50 plate stacks. The high capacity stacking system in a preferred embodiment is used as an input source and output buffer, for a liquid processing system (see FIG. 11). Alternatively, the high capacity stacking system can be used as a plate conversion device for a screening sample distribution module or a hit profiling robot.

The high capacity stacking system can be operated to perform many different plate sorting functions for screening to improve adaptive routing or flexibility in screening protocols. For instance, a technician loads 500 empty plates into the ten stacks of a high capacity stacking system attached at a lift and transport station along the sample transporter (see FIG. 11). The storage and retrieval module retrieves master plates from the storage and retrieval module and the high capacity stacking system provides empty plates for replication at the screening sample distribution module at another lift and transport station on the sample transporter. The resulting daughters are directed back into the high capacity stacking system to be removed by the technician. The removable stacks allow a family of workstations to share input and output fornmats, i.e. the stacks are interchangeable between workstations to allow workstations to be linked.

Example 5 —Random Access High Density Plate Presentation Module

The random access high density plate presentation module presents high density plates to the sample transporter (see FIG. 11). The random access high density plate presentation module can be mechanically linked to a sample transporter using a platen that positions the plate on the sample transporter by moving the platen partially over the sample transporter and sliding the plate onto the sample transporter with a member on the platen that slides the plate off the platen and onto the sample transporter. To avoid the plate from being slid onto the sample transporter, the random access high density plate presentation module can include a lifting platen that can be disposed on the sample transporter to engage the platen or the plate and lift the plate from the platen. At which point the platen is withdrawn and the lifting platen is positioned to allow the plate to rest on the sample transporter. The random access high density plate presentation module can also be mechanically linked to a sample transporter with a conveyor means. The random access high density plate presentation module comprises a plurality of stacks, preferably removable stacks, that hold plates. Each stack is connected to either a platen or a conveyor system that has a lifting platen that either stacks or destacks plates by engaging the plate bottom. Alternatively, stacking systems in the prior art can be used, such as those available from Carl Creative Systems (Carson City, Calif., USA) and Packard Instrument Company (Meriden, Conn., USA), or stacking systems developed in the future.

Example 6 —Screening Reagent Dispensing Robot

The screening reagent dispensing robot can dispense reagents necessary for performing a screen. A screening reagent dispensing robot can rapidly, accurately and reproducibly dispense solutions in an addressable well in predetermined volumes. In most embodiments the screening reagent dispensing robot is an array or plurality of dispensers that are in fluid communication with a reagent reservoir. Aspiration by the dispensers is usually not required. A screening reagent dispensing robot can be adapted to dispense a particular type of reagent or, depending on the reagents, different reagents. Usually, washing steps will be required when reagents are switched to minimize cross contamination. Reagents for a screen can include reagent buffers, dyes, agonists, antagonists, and cells. Multiple screening reagent dispensing robots can be integrated and operably linked as part of a screening system, such the one shown in FIG. 11.

In one embodiment the screening reagent dispensing robot comprises computer-controlled electronic valve drivers for precise control of voltage pulse width, voltage amplitude and back EMF dissipation. In applications where fast delivery speed (e.g., at least about 50 to 1,000 microseconds) is important, fast operating valves should be chosen to control fluid flow. This is especially advantageous at the lower end of dispensed volume range, which often necessitates high resolution, accurate and reproducible control of the valves. Preferably electronically controlled (e.g., solenoid) valves are used instead of pneumatic valves. In such cases, the software in the programmable logic controller or computer has a microsecond resolution and accuracy. In one embodiment the inventors utilized a hardware timed driver that was capable of simultaneously delivering up to 200 volts to up to 96 valves with microsecond accuracy and programmable time control.

Measured and calculated dispense times are shown in Table 4 for a linear array of 48 dispensers.

distal tip end to be disposed along the axis at the desired spacing. Preferably, the tips must allow dispensation within a 1 mm internal diameter well and to produce a stream significantly less than 1 mm in diameter in order to not form bubbles as the reagent is delivered into the well. In addition, the dispenser tip typically permits repeated, individual dispenses of 100 nanoliters.

Tips can be engaged to fluid connections and angled using a variety of configurations. For example, the outlet end of the valve is a stainless steel tube 0.2" (5.08 mm) in length with an O.D. of 0.020" (0.51 mm) and I.D. of 0.010" (0.25 mm). This will mate with a 1.25" (31.75 mm) long, type 304 stainless steel tube (gauge 33, O.D. of 0.008" (0.20 mm) and I.D. of 004" (0.10 mm)). The gauge 33 tube fits inside the valve inlet tube and the two tubes are bonded together using

TABLE 4

| Per Dispenser Volume (nanoliter) | Per Dispenser Dispense Time (msec) | Per 48-Array Positioner Move time (msec) | Pause Time (msec) | Total (msec) | Per Plate Total Time (sec) |
| --- | --- | --- | --- | --- | --- |
| 20 nanoliters | 1 | 500 | 100 | 601 | 43 |
| 2 microliters | 100 | 500 | 100 | 700 | 50 |
| 5 microliters | 250 | 500 | 100 | 850 | 61 |

The dispenser was a solenoid dispenser with a dynamic range of about 5 nanoliters to 10 microliters. The fluid pressure was about 7 psi. At one minute per plate, a linear array dispenser can fill approximately thirty 3,456 plates per hour. This assumes a worst-case time of about 1 minute to change plates. Thirty such plates is equivalent to over 90,000 samples per hour. Assuming 10% of the plates are used for controls, 720,000 samples can be processed in an 8 hour work period (1,080,000 samples can be processed in a 12 hour work period).

Preferably, solenoid valves are used for a screening reagent dispensing robot. These valves are capable of delivering as little as 5 nanoliters with the proper tip configuration. With the caliber tips described herein, the minimum dispensed volume is in the range of about 25 nanoliters. The maximum dispensed volume is mainly limited by the size of the reagent reservoir. Comparable valves can be used for preferred embodiments, such as those known in the art or developed in the future. Alternatively, piezo based dispensers can be used to dispense picoliter volumes (e.g., about 5 to 500 picoliters and preferably about 100 picoliters). Such piezo devices are available from sources described herein.

The screening reagent dispensing robot can also include dispenser tips specifically designed to accommodate manifolds that permit close spacing of tips. Typically, tips are spaced less than about 5 mm apart and preferably about less than 1 mm apart. Since fluid connections (e.g., channels) to the tips are preferably larger than the spacing between tips, so as to increase fluid flow, minimize hydraulic resistance, and reduce clogging. Fluid connections are disposed in a pattern that allows a properly angled tip to have a distal tip end disposed with the desired spacing. Typically, the fluid connections will be staggered along an axis and the tips will engage the fluid connections at an angle that permits the Teflon heat shrink/melt tubing (Small Parts, Inc. cat #: E-SMDT-036). A 25° bend exists 0.5" from the dispensing end of the tip. This 0.5" inch segment is placed in a tip block which aligns each tip into a linear array. The remaining 0.75" segment is bent 10°, either up or down, to align it with a valve in one of two valve blocks.

A stainless steel block can be used to hold and position the dispenser tips into a linear array with a 1.5 mm pitch. Each tip fits into a slot within the block. The block has a U-shaped groove that intersects each slot. Once all the tips are in place and aligned, a holder bar is screwed into the groove that presses against each tip and holds them in place.

A stainless steel block can also hold and position valves into a linear array with a desired pitch. For example, a 6.0 mm pitch would be compatible for a 48 head array using 12 lee valves. Each valve slides into a cylindrical groove within the block and is held in place by the tip block's hold on the tip. Four of these valve blocks, placed side by side at an angle and offset 1.5 mm in relation to each other, can yield a linear arrangement of 48 valves tips. If fast flush solenoid valves are used, it is desirable have fluid connection with the tip via Teflon tubing.

The screening reagent dispensing robot has a fluid path to each tip and valve with minimal volume and dead spaces. Preferably, the fluid path to each tip is identical (but not necessarily shared) as to other dispensers. The tip has the most resistance to fluid flow so its design is preferably identical as possible for each dispenser site in order to minimize variation in volume dispensed between valve/dispenser tips. The valving system allows residual reagent to be washed prior to delivery of a new reagent. All fluid lines are preferably Teflon™ (e.g., FEP) or silicone, or a chemically inert material. The only exception to this is the tip, which is typically high quality polished stainless steel. Fluid manifolds are usually constructed in Teflon and mate with the valve inlets via friction fittings. A fluid manifold is usually shared among a plurality of valves, e.g., it connects to 12 valves. The manifold has ports on both ends that allow it to be a flow through or dead end system. All the valves can be connected to a single reagent reservoir by connecting manifolds together in parallel or in series.

The fluid reservoir can vary depending on the application and the required volumes and solvents. A variety of volume ranges are possible depending on the type of reservoir that is used. A pressure chamber, like the one from EFD (Model 615DTH), that will allow a variety of reagent bottles to be used is advantageous, since the whole bottle is placed inside a pressurized chamber. An alternative is to pressurize just the bottle and place the bottle within a shielded safety chamber. A third alternative is to use a fluid reservoir designed to hold low pressure.

If live cell cultures are being dispensed, the recommended reservoir is a stirred container. An example is the stirred filtration container (Amicon, MA, USA) which has the further advantage of having a built-in stirring mechanism to keep cells suspended. This container is available in 3, 10, 50, 200 and 400 ml sizes. If the dispense routine requires any significant amount of time (more than a few minutes), it will be necessary to provide re-circulation of the cell culture through the fluid system in order to prevent adhesion or pooling of the cells. This can be done via peristaltic pumps, though rotary piston pumps may be preferable since they potentially cause less damage to cells.

Fluid is delivered to the valves by pressurizing the reagent reservoir with a fluid, such as a gas. The Model 8310 (0–10 psi) pressure regulator from Porter Instrument Co. can be used and the like. Honeywell Microswitch pressure sensors will monitor pressure and a pressure relief valve, rated for 10 psi, and the like can be included. For superior pressure control and dispensing valves can be arranged in series and electronically controlled to coordinate dispensing and to provide desired pressures. This can allow pressures to be changed in the fluid system if so desired.

The dispenser arrays are typically positioned over the desired wells with an X,Y positioner. A suitable X,Y positioner preferably, permits the array to be positioned over wells having a density greater or less than the distance between tips. This allows the screening reagent dispensing robot to be used for plates of different well densities.

Figure 18:
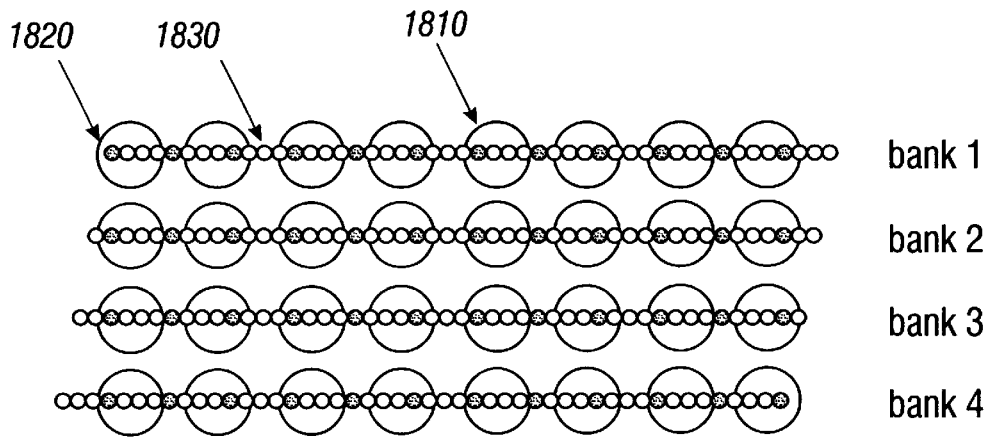
FIG. 18 shows different dispensing positions.
Figure 18:
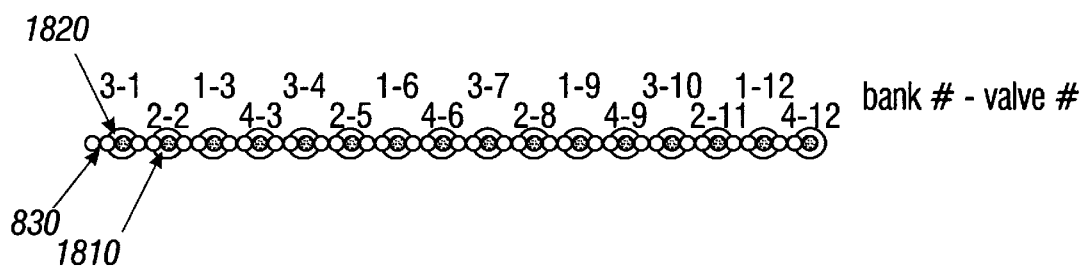
Figure 18:
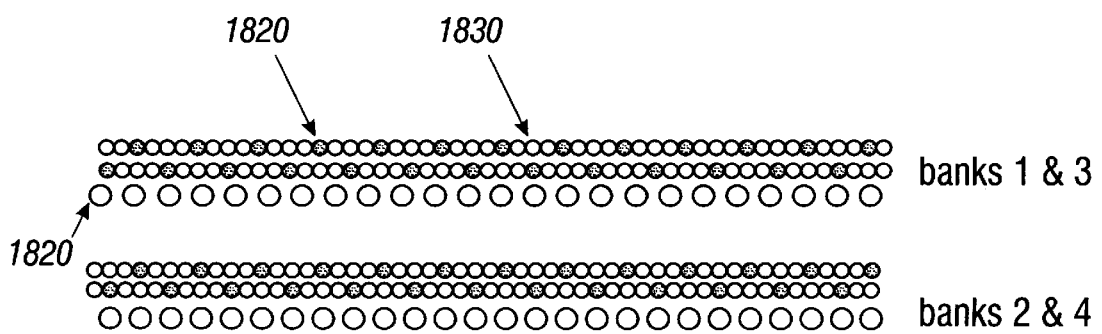

FIG. 18 shows different well densities in relation to different tip positions of a dispenser array. A well 1810 is addressed by a possible tip 1820 (filled circles). Also shown are tip positions 1830 (open circles) that may or may not address a well depending on the well density. Each bank shown is an array. The increased spatial density of the dispenser and the increased two dimensional density of the target plate require substantial positioning accuracy. The positioning accuracy tolerance is typically about 200 microns or less, and preferably about 50 microns or less in order to ensure that the proper position in the wells for dispensation can be achieved. Alternatively, such positioning paradigms can be used for detectors.

A reagent dispensing robot can include integrated computer control for managing and directing the entire dispense operation. The linear array dispenser and its integrated positioning requirements can use sophisticated computer control for effective operation. The computer not only monitors the status of key sensors (e.g., reagent bottle pressure, liquid level, plate position, and positioning limit switches) but also provides the interface for generating specific liquid dispensation patterns and volumes to the high density plate. Timing of dispensation can be accomplished by a variety of means known in the art and developed in the future, so long as such timing means are suitable for the time frame and control desired. For example, the National Instruments AT-MIO-16XE-50 board can be used as timing means to send timing signals to two of their AT-DIO-32F boards. The 64 ports on these 32F boards are kept normally high and send out timed low signals. An inverter board is used to make the timed portion high and these high signals are used to close high voltage relays (Opto ODC5A) which run the valves. An OV'R driver (Lee Company cat #DRVA0000010A) is used to protect the valves from overheating during prolonged open periods.

The software controlling the valves (or dispensers) can be written to integrate into a screening system or for a standalone use. Software for laboratory instrumentation is known in the art and can be used. For example, software can be written in LabVIEW (National Instruments, TX, USA). The user selects a valve opening time and the valves to be opened. This program can be embedded within a larger program that controls other features (such as the X,Y positioner) to obtain an automatic dispenser.

All materials must be substantially compatible with the required reagents over the time frames that the materials are used. The reagents should be relatively inert to components and the materials used in the construction of this dispenser must relatively inert to the reagents. This is especially critical for whole viable cells which may be used in screening assays. Materials are preferably non cytotoxic, non hemolytic, non-aggregating surfaces, and non sticky to biological materials.

The motive force for the liquid can be supplied by pressurized bottles ( in a preferred embodiment) or via positive displacement means including syringes, pistons, peristaltic and rotary pumping mechanisms. In-line filtration or inlet filtration can be introduced to the system for reducing contaminating particles.

A preferred embodiment of a screening reagent dispensing robot is a set of at least two linear arrays (banks) of dispensers on a X,Y positioner in fluid communication with a plurality of electronically controlled valves (e.g., solenoid or piezo) that are in fluid communication with at least one reagent reservoirs. Dispenser tips are spaced to accommodate the density of the addressable wells on a plate. For example, for a high density plate, tips are about 1.5 mm apart. The X,Y positioner permits each tip in a bank to be position over the desired well, preferably independently of the other banks. The valves are individually and electronically controlled and can be opened simultaneously or in any pattern with microsecond resolution. Typically, the dispensers can rapidly dispense about 50 to 10,000 nanoliters (or lower ranges about 25 picoliters to 1,000 nanoliters) of a single reagent into predetermined combination of wells of a high density plate, preferably without physical contact.

Preferably, the screening reagent dispensing robot is compatible with different dispensing solutions, including aqueous, alcohol and DMSO based reagents.

Figure 19A:
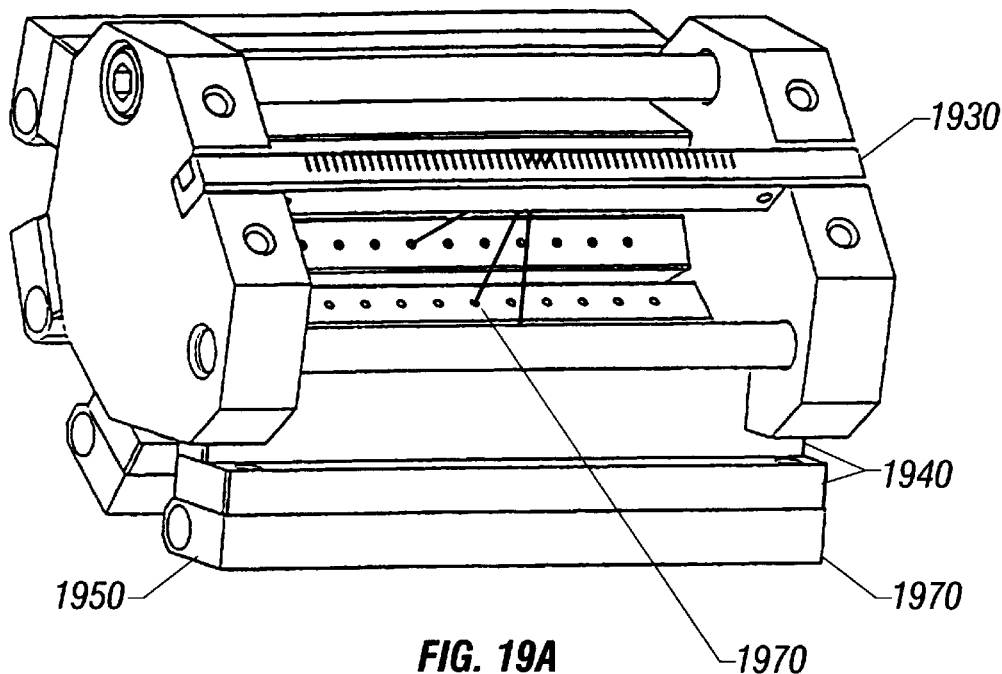
FIG. 19A and 19B shows one embodiment of a screening reagent dispensing robot.
Figure 19B:
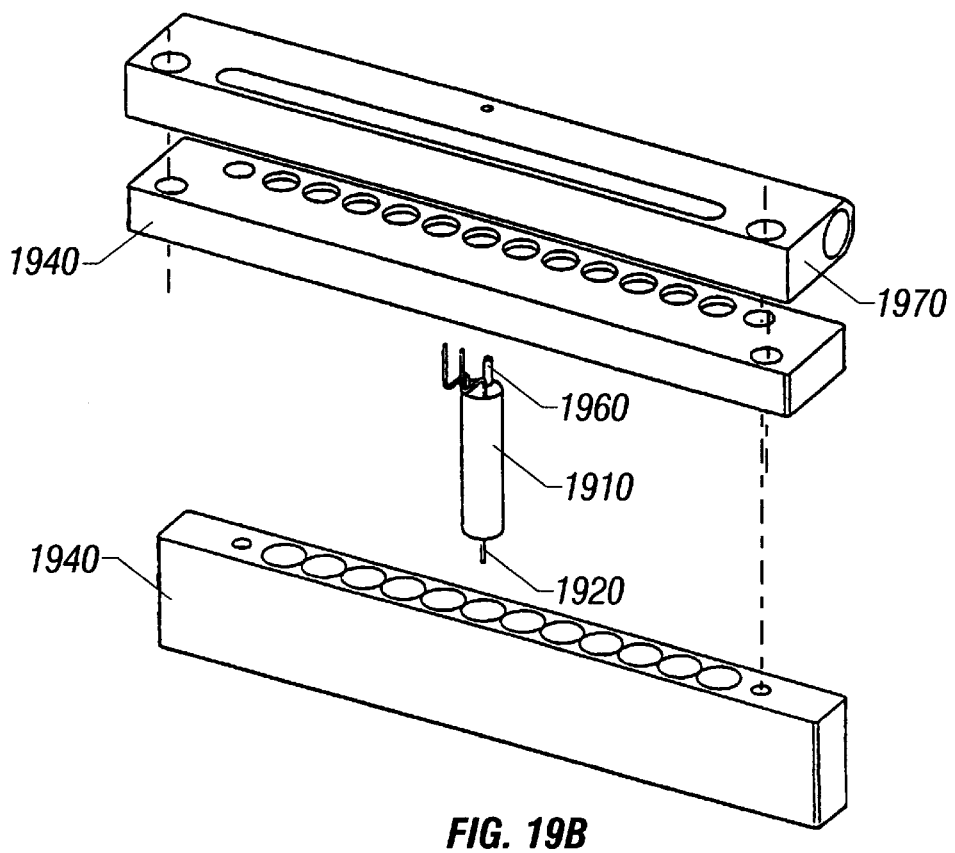

FIG. 19A (cut-away view of assembled unit) and B (exposed view of one bank) shows components of one embodiment of a screening reagent dispensing robot that includes valves 1910, valve tips 1920 (straight tip in FIG. 19B, bent tip in FIG. 19A, tip block 1930, valve block 1940, valve block assembly 1950, fluid lines 1960, and fluid manifold 1970, fluid reservoir 1980, and pressure system are not shown.

In a preferred embodiment, four linear arrays of 12 valves (banks) each are placed side by side. The valves and dispenser tips in each of these arrays are spaced 6 mm apart and each array is staggered 1.5 mm in relation to each other. The tips of the valves are configured to share the same fluid path configuration and align together into a linear array of 48 tips spaced 1.5 mm apart. The tips from a single bank of valves are spaced 6 mm apart and are arranged as every fourth tip in the 48 tip array Another embodiment uses larger valves that would require larger spacing between each valve. The tips in this embodiment would use flexible tubing to connect the valve and tips.

Each valve can be individually controlled to allow different patterns of dispensing. Though designed to dispense into a 48 well per coluin plate, this array could also dispense into other plate configurations. For example, 864-well plates (24 by 36 wells), 384-well plates (16 by 24 wells) or 96-well plates (8 by 12 wells) are compatible by using every second, third or sixth valve, respectively. If the plate can be moved in the Y as well as the X direction, then each 48 valve linear array can dispense up to four different reagents by plumbing a different reagent into each of the four banks of 12 valves. Moving the plate in both the X and Y directions allows each well to align with a valve tip from each bank. If the plate can only be moved in the X direction, then the following dispensing arrangements are possible with a 48-dispenser array (see FIG. 19). 96-Well Plate (6.5 mm diameter wells) Multiple Reagent Mode A single 48 valve linear array can deliver up to four different reagents into a 96-well plate since a single bank can deliver into each well. Each bank is plumbed to receive a different reagent. Plate can be secured properly in the Y direction for each reagent and the plate does not need to move in the Y direction during the dispensing of that one reagent.

384 Well Plate (3.4 mm diameter wells) Single Reagent Mode

Valves from each bank must be used in order to dispense into each well of a 384-well plate; therefore only one reagent can be dispensed from the 48 tip array.

864-Well Plate (2.0 mm diameter wells)

Each well can be accessed by using either banks 1 and 3 or banks 2 and 4. This allows two different reagents to be delivered if the plate is aligned properly in the Y direction for each reagent.

In operation, the linear array of dispensers can be positioned over a high density plate, e.g., 48 by 72-well plate. The wells in this plate are spaced identically to the dispensers (1.5 mm apart). The dispensers are activated and a reagent is dispensed simultaneously into each well in one column. The plate is then moved over one column and the dispensers are again activated. This is repeated over the entire plate. The amount dispensed is controlled by the valve opening time and the pressure feeding the reagent to the valves (other factors also control dispensed volumes, particularly restrictions to flow). Variable amounts can be dispensed into each well by controlling the timing of valve opening and the dispensation pattern across the linear array of valves. Each dispenser of the linear array can be individually controlled via software The entire fluid path can be flushed clean by first purging the four fluid manifolds, followed by each of the 48 valves. Three 3-way valves (two on the input side and one on the output side of the fluid manifolds) will allow flushing with a wash liquid and with air. The device can be cleaned between reagent changes and for long-term inactive periods. The valve assembly can be designed in a modular form in order to facilitate replacement and repair of single valve/tip components and/or whole banks of valves. The fluid path dead space is preferably designed to minimize flush out volumes.

In another embodiment, the dispenser tip pitch can be modulated via a cam shaft mechanism which enables on-the-fly control of dispenser tip spacing.

In another embodiment, each valve array can contain a different reagent and address the dispensation requirements of the assay by additional positioning movements under the linear array dispenser.

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. A device for identifying useful chemicals, comprising:
    a) a storage and retrieval module comprising storage locations for storing a plurality of chemicals in solution in addressable chemical wells, a chemical well retriever, and having programmable selection and retrieval of said addressable chemical wells,
    b) a sample distribution module comprising a liquid handler to aspirate or dispense solutions from selected said addressable chemical wells, said sample distribution module having programmable selection of, and aspiration from, said selected addressable chemical wells and programmable dispensation into selected addressable sample wells,
    c) at least one multi-lane sample transporter to transport said selected addressable chemical wells to said sample distribution module and optionally having programmable control of transport of said selected addressable chemical wells, wherein at least one lane of said multi-lane sample transporter functions to provide bidirectional transport of said selected addressable chemical wells to or from said storaRe and retrieval module,
    d) a reaction module comprising either a reagent dispenser to dispense reagents into said selected addressable sample wells or a fluorescent detector to detect chemical reactions in said selected addressable sample wells, and e) a data processing and integration module; wherein said storage and retrieval module, said sample distribution module, and said reaction module are integrated and programmably controlled by said data processing and integration module; and said storage and retrieval module, said sample distribution module, said multi-lane sample transporter, said reaction module and said data processing and integration module are operably linked to facilitate rapid processing of said addressable sample wells.

2. The device of claim 1, wherein said storage and retrieval module has storage locations for at least 200,000 said addressable chemical wells in a plurality of addressable chemical plates, said addressable chemical plates are operably linked to at least one plate buffer that loads and unloads said addressable chemical plates in a predetermnined order that is either dependent or independent of the order of selection of said addressable chemical plates, said chemical well retriever is adapted to retrieve and replace selected said addressable chemical plates and is controlled by a program to reduce retrieval and replacement time of said chemical well retriever during retrieval and replacement.

3. The device of claim 1, wherein an addressable chemical plate of said plurality of addressable chemical plates has a standard footprint and said liquid handler can dispense into arrays of addressable wells with different densities of addressable wells per centimeter squared.

4. The device of claim 3, wherein said addressable chemical plates have a well-to-well distance of about 4 mm or less.

5. The device of claim 1, wherein said storage and retrieval module further comprises storage locations for at least 20,000 addressable sample wells in a plurality of sample plates each having said standard footprint and said chemical well retriever is adapted to store and retrieve selected said addressable sample plates, and said chemical well retriever is adapted to retrieve addressable sample plates of a different height than said addressable chemical plates.

6. The device of claim 2, wherein said storage and retrieval module further comprises an environmental control unit to modulate temperature and humidity of said storage and retrieval module.

7. The device of claim 1, wherein said multi-lane sample transporter is a reduced friction, ortho-multilane conduit that operably connects a plate buffer to said sample distribution module to facilitate transport of said addressable chemical plates or said addressable sample plates.

8. The device of claim 5, wherein said chemical well retriever is adapted to store and retrieve selected of said addressable chemical plates having lids.

9. The device of claim 8, wherein said chemical well retriever has a universal plate handler.

10. The device of claim 1, wherein said liquid handler comprises a plurality of dispensers that can individually dispense a predetermined minimum volume of less than approximately 2,000 nanoliters of liquid aspirated from a predetermined selection of said addressable chemical wells into a predetermined selection of said addressable sample wells.

11. The device of claim 10, wherein said dispensers comprise solenoid valves fluidly connected to a reservoir for liquid aspirated from an addressable chemical well and said solenoid valves control release of hydraulic pressure in said reservoir.

12. The device of claim 10, wherein said dispenser comprises a fluid channel to aspirate liquid from a predetermined selection of said addressable chemical wells.

13. The device of claim 10, wherein said dispenser comprises an electrically sensitive volume displacement unit in fluid communication with a dispensing nozzle.

14. The device of claim 1, wherein said reaction module comprises a detector to detect signals in said addressable sample wells, wherein said detector is optically connected to illuminate selected said addressable sample wells.

15. The device of claim 14, wherein said detector illuminates a predetermined selection of said addressable sample wells and detects fluorescence from said addressable sample wells.

16. The device of claim 14, further comprising a positioner that positions said addressable sample wells to permit interrogation of a predeterrnined selection of addressable sample wells and said detector is disposed to illuminate without substantial interference from said positioner.

17. The device of claim 16, wherein said positioner can position said addressable sample wells with a minimal ccnter-to-center distance between approximately 0.5 mm to 1.0 mm.

18. The device of claim 1, wherein said data processing and integration module controls the retrieval of selected said addressable chemical wells, aspiration of selected reagents from said addressable chemical wells, transport of said sample wells to said sample distribution module, dispensing into selected sample wells, routing said sample wells to said detector and collecting and storing data output from said detector.

19. The device of claim 1, wherein said data processing and integration module comprises an adaptive processing program to route said addressable sample wells to workstations.

20. The device of claim 1, wherein said storage and retrieval module, said sample distribution module, said multi-lane sample transporter, said reaction module and said data processing and integration module process said addressable samples at a rate of about 100,000 per day and said sample distribution module, said multi-lane sample transporter, and said reaction module are adapted to process miniaturized addressable sample wells having sample volumes of less than about 5 microliters.

21. The device of claim 1, wherein said device can process at least 100,000 addressable sample wells in 24 hours.

22. The device of claim 1, wherein storage and retrieval module can store at least about 1,000,000 addressable chemical wells and said device can process at least 250,000 addressable sample wells in 24 hours.

23. A device for rapidly identifying or processing liquid chemical samples, comprising:

a storage and retrieval module comprising storage locations for storing a plurality of reagents in solution in addressable chemical wells, and having programmable selection and retrieval of said addressable chemical wells and having a storage capacity for said addressable chemical wells, a sample distribution module comprising a liquid handler to aspirate or dispense solutions from selected said addressable chemical wells, said sample distribution module havin, programmable selection said selected addressable chemical wells, at least one multi-lane sample transporter to transport of said selected addressable chemical wells to said sample distribution module and optionally having programmable control of transport of said selected addressable chemical wells, wherein said multi-lane sample transporter comprises at least four tracks and at least two tracks of said four tracks transport in one direction, a reaction module comprising either a reagent dispenser to dispense reagents into said selected addressable sample wells for reaction or a detector to detect chemical reactions in said selected addressable sample wells, and a data processing and integration module; wherein said storage and retrieval module, said sample distribution module, and said reaction module are integrated and programmably controlled by said data processing and integration module; and said storage and retrieval module, said sample distribution module, said multi-lane sample transporter, said reaction module and said data processing and integration module are operably linked to facilitate rapid processing of said addressable sample wells;

further wherein said device can process at least 25,000 addressable sample wells in 24 hours.

24. The device of claim 23, wherein said device can process at least 100,000 addressable sample wells in 24 hours.

25. The device of claim 23, wherein storage and retrieval module can store at least about 1,000,000 addressable chemical wells and said device can process at least 250,000 addressable sample wells in 24 hours.

26. The device of claim 23, wherein further said multi-lane sample transporter comprises a conveyor means.

27. The device of claim 24, wherein said storage and retrieval module has storage locations for at least 200,000 said addressable chemical wells in a plurality of addressable chemical plates, said addressable chemical plates are operably linked to at least one plate buffer that loads and unloads said addressable chemical plates in a predetermined order that is either dependent or independent of the order of selection of said addressable chemical plates.

28. A device for rapidly screening samples containing a molecular target, comprising:

a) a storage and retrieval module comprising a plurality of putative modulator solutions, said plurality disposed of putative modulator solutions in addressable storage modulator plates, and having programmable selection and retrieval of said addressable modulator plates, wherein said storage and retrieval module has storage locations for said addressable modulator plates, b) a sample distribution module comprising a liquid handler to aspirate or dispense solutions from selected said addressable modulator plates, said sample distribution module having programmable selection of said selected addressable modulator plates, c) at least one multi-lane transporter for transporting modulators and to parallel transport and facilitate parallel processing of modulator plates said selected addressable modulator plates to said sample distribution module and optionally having programmable control of transport of said selected addressable modulator plates, wherein at least one lane of said multi-lane sample transporter functions to provide bidirectional transport said selected addressable chemical wells to or from said storage and retrieval module, d) a reagent dispenser to dispense reagents into said addressable sample wells for reaction, e) a detector to detect activity of a modulator with respect to molecular targets in said addressable sample wells, and a data processing and integration module; wherein said storage and retrieval module, said sample distribution module, and said reagent dispenser are integrated and programmably controlled by said data processing and integration module; and said storage and retrieval module, said sample distrbution module, and said multi-lane transporter are optionally not mechanically linked to said reagent dispenser and said detector by said multi-lane transporter; and said reagent dispenser, said detector and said data processing and integration module are operably linked to facilitate screening of molecular targets in said addressable sample wells, wherein said detector and said data processing and integration module can process said addressable sample wells at rate of at least 50,000 per day.

29. The device of claim 28, wherein said data processing and integration module comprises an adaptive processing program to route said addressable modulator plates to workstations.

30. The device of claim 29, wherein said multi-lane sample transporter is a reduced friction, ortho-multilane conduit that operably connects a plate buffer to said sample distribution module to facilitate transport of said addressable chemical plates or said addressable sample plates.

* * * * *